(12) United States Patent
Kain et al.

(10) Patent No.: US 11,939,638 B2
(45) Date of Patent: *Mar. 26, 2024

(54) SYSTEMS AND METHODS FOR IDENTIFYING AND DISTINGUISHING GENETIC SAMPLES

(71) Applicant: REVERE BIOSENSORS, LLC, Birmingham, MI (US)

(72) Inventors: Robert Charles Kain, San Diego, CA (US); Theofilos Kotseroglou, Hillsborough, CA (US); Vladimir Bashkirov, Davis, CA (US); Richard Shen, Rancho Santa Fe, CA (US)

(73) Assignee: REVERE BIOSENSORS, LLC, Worcester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/612,339

(22) PCT Filed: May 8, 2018

(86) PCT No.: PCT/US2018/031636
§ 371 (c)(1),
(2) Date: Nov. 8, 2019

(87) PCT Pub. No.: WO2018/208804
PCT Pub. Date: Nov. 15, 2018

(65) Prior Publication Data
US 2020/0172985 A1    Jun. 4, 2020

Related U.S. Application Data

(60) Provisional application No. 62/503,502, filed on May 9, 2017, provisional application No. 62/546,929, filed on Aug. 17, 2017, provisional application No. 62/586,760, filed on Nov. 15, 2017.

(51) Int. Cl.
*C12Q 1/6888* (2018.01)
*C12Q 1/6825* (2018.01)
*C12Q 1/70* (2006.01)
*G01N 27/447* (2006.01)

(52) U.S. Cl.
CPC ......... *C12Q 1/6888* (2013.01); *C12Q 1/6825* (2013.01); *C12Q 1/701* (2013.01); *G01N 27/44791* (2013.01)

(58) Field of Classification Search
CPC .... C12Q 1/6888; C12Q 1/6825; C12Q 1/701; C12Q 2600/158; C12Q 1/70; C12Q 2563/107; C12Q 2563/116; C12Q 2565/125; C12Q 2565/501; C12Q 2565/607; C12Q 2565/629; C12Q 2565/631; G01N 27/44791
See application file for complete search history.

(56) References Cited

U.S. PATENT DOCUMENTS

| | | | |
|---|---|---|---|
| 5,376,252 A * | 12/1994 | Ekstrom | G01N 27/44704 204/603 |
| 5,510,270 A | 4/1996 | Fodor et al. | |
| 5,563,034 A | 10/1996 | Brink et al. | |
| 5,593,867 A | 1/1997 | Walker et al. | |
| 6,821,770 B1 * | 11/2004 | Hogan | C12Q 1/689 536/23.1 |
| 7,083,917 B2 | 8/2006 | Barany et al. | |
| 8,105,471 B1 * | 1/2012 | Han | G01N 27/44752 204/601 |
| 9,683,960 B2 * | 6/2017 | Bercovici | C12Q 1/6816 |
| 2001/0055760 A1 | 12/2001 | Chenchik | |
| 2002/0137031 A1 | 9/2002 | Wolber | |
| 2004/0202577 A1 | 10/2004 | McNeil et al. | |
| 2004/0219530 A1 | 11/2004 | Brousseau et al. | |
| 2005/0032095 A1 | 2/2005 | Wigler et al. | |
| 2005/0136395 A1 | 6/2005 | Mittmann et al. | |
| 2005/0170362 A1 * | 8/2005 | Wada | G01N 33/5306 435/7.1 |
| 2005/0255459 A1 | 11/2005 | Fofanov et al. | |
| 2006/0194223 A1 | 8/2006 | Andreoli et al. | |
| 2007/0178516 A1 * | 8/2007 | Sosnowski | B82Y 5/00 435/6.11 |
| 2008/0057513 A1 | 3/2008 | Farrell | |

(Continued)

FOREIGN PATENT DOCUMENTS

| | | |
|---|---|---|
| CN | 101157952 A | 4/2008 |
| CN | 104419764 A | 3/2015 |

(Continued)

OTHER PUBLICATIONS

Bates et al. Cooperativity of paired oligonucleotide probes for microarray hybridization assays. Anal Biochem. Jul. 1, 2005;342(1):59-68. doi: 10.1016/j.ab.2005.03.030. Epub Apr. 15, 2005.
PCT/US2018/031636 International Preliminary Report on Patentability dated Nov. 12, 2019.
PCT/US2018/031636 International Search Report and Written Opinion dated Jul. 11, 2018.
U.S. Appl. No. 15/776,244 Office Action dated Oct. 2, 2020.
EP18798644.3 Extended European Search Report dated Nov. 13, 2020.

(Continued)

*Primary Examiner* — Narayan K Bhat
(74) *Attorney, Agent, or Firm* — Wilson Sonsini Goodrich & Rosati

(57) ABSTRACT

Method and systems for identifying and distinguishing subjects using a detection system comprising pooled probes are described. The pooled probes described comprise subject specific features allowing for identification and distinction of subjects in a complex sample and can be utilized in a variety of detection platforms. The methods and systems can further comprise the use of isotachophoresis to concentrate analytes in a sample.

17 Claims, 24 Drawing Sheets

Specification includes a Sequence Listing.

(56) References Cited

U.S. PATENT DOCUMENTS

| | | |
|---|---|---|
| 2009/0181378 A1 | 7/2009 | Sanders et al. |
| 2012/0122737 A1 | 5/2012 | Sabot et al. |
| 2016/0177382 A1 | 6/2016 | Han et al. |
| 2018/0265918 A1 | 9/2018 | Shirai et al. |
| 2019/0039069 A1* | 2/2019 | Marshall .......... G01N 27/44791 |
| 2020/0087717 A1 | 3/2020 | Kain et al. |
| 2022/0136043 A1 | 5/2022 | Kotseroglou et al. |

FOREIGN PATENT DOCUMENTS

| | | | |
|---|---|---|---|
| CN | 104677972 A | 6/2015 | |
| JP | 2001514906 A | 9/2001 | |
| JP | 2005509127 A | 4/2005 | |
| JP | 2006524319 A | 10/2006 | |
| WO | WO-0242775 A2 | 5/2002 | |
| WO | WO-02101094 A1 | 12/2002 | |
| WO | WO-2007027495 A1 | 3/2007 | |
| WO | WO-2014185803 A2 | 11/2014 | |
| WO | WO-2015079446 A1 * | 6/2015 | .......... B01L 3/50273 |
| WO | WO-2016187234 A1 | 11/2016 | |
| WO | WO-2017087416 A1 | 5/2017 | |
| WO | WO-2018208804 A1 | 11/2018 | |

OTHER PUBLICATIONS

Vilensky et al. Oxidized Porous Silicon Nanostructures Enabling Electrokinetic Transport for Enhanced DNA Detection. Advanced Functional Materials, vol. 25, Issue 43, pp. 6725-6732 (Nov. 18, 2015). First published Oct. 6, 2015. DOI: https://doi.org/10.1002/adfm.201502859.

Deyholos et al., High-density microarrays for gene expression analysis. Cytometry. 43(4):229-238 (2001).

European Patent Application No. 16866968.7 Supplementary Search Report dated Jun. 7, 2019.

International Application No. PCT/US16/62090 International Preliminary Report on Patentability dated May 31, 2018, pp. 1-14.

International Application No. PCT/US2016/062090 International Search Report and Written Opinion dated Mar. 17, 2017, pp. 1-15.

Miller et al., Basic concepts of microarrays and potential applications in clinical microbiology. Clinical Microbiology Review. 22(4):611-633 (2009).

Molecular Devices: "Genepix 4000B Microarray Scanner: User Guide". Retrieved from the Internet URL: http://mdc.custhelp.comjeufjassetsjcontentjGenePix_4000B_UserGuide.pdf (2010).

PCT/US2018/034636 International Preliminary Report on Patentability dated Nov. 12, 2019.

Woo et al., A comparison of cDNA, oligonucleotide, and Affymetrix GeneChip gene expression microarray platforms. Journal of Biomolecular Techniques. 15(4):276-284 (2004).

Co-pending U.S. Appl. No. 15/776,244, filed May 15, 2018.

U.S. Appl. No. 15/776,244 Final Office Action dated Jun. 4, 2021.

Divne et al. A DNA microarray system for forensic SNP analysis. Forensic Science International 154 (2005) 111-121. Available online Dec. 2, 2004.

Huang et al. Efficient SNP Discovery by Combining Microarray and Lab-on-a-Chip Data for Animal Breeding and Selection. Microarrays 2015, 4, 570-595.

Komura, et al. Genome-wide detection of human copy number variations using high-density DNA oligonucleotide arrays. Genome Res. 2006; 16(12): 1575-84.

Li et al. Multiplexed analysis of polymorphisms in the HLA gene complex using bead array chips. Tissue Antigens 2004: 63:518-528 (2004).

U.S. Appl. No. 15/776,244 Office Action dated Jun. 13, 2022.

U.S. Appl. No. 15/776,244 Notice of Allowance dated Mar. 21, 2023.

* cited by examiner

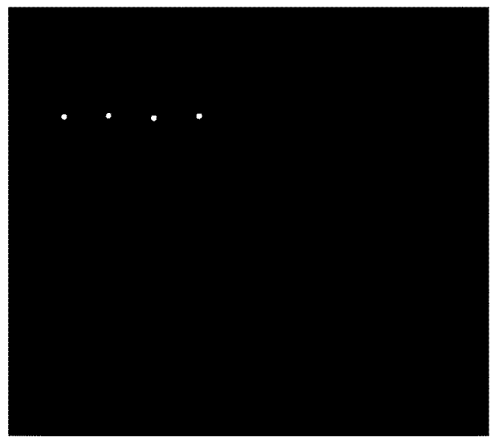
Relative brightness = 1 flourophores/feature
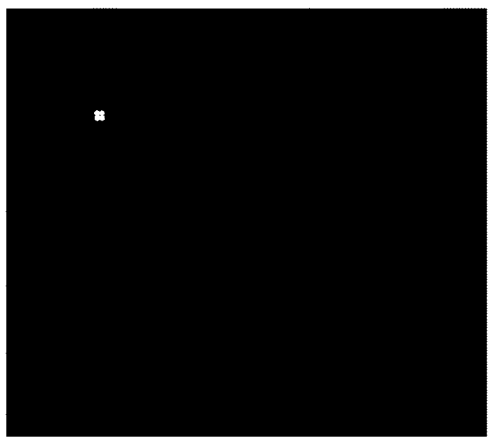
Relative brightness = 10 flourophores/feature
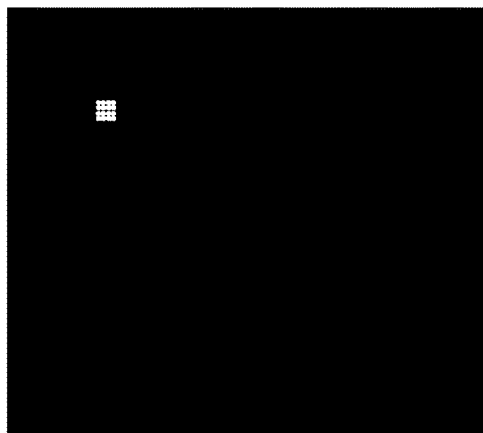
Relative brightness = 50 flourophores/feature
FIG. 2

| Probe Name | Sequence | GC Content | Tm | Hairpin Tm | Start | Scale | Purification | 5' modification | 3' modification |
|---|---|---|---|---|---|---|---|---|---|
| M13P296 | 5'-CGACCTCGGTACCCGGGATCCTCTAGAGTCGACC | 65.7 | 69.8 | 43 | 6235 | 250 nmole | PAGE | | |
| M13P296A | NH2-AL21A-5'-CGACCTCGGTACCCGGGATCCTCTAGAGTCGACC | 65.7 | 69.8 | 43 | 6235 | 1 umole | HPLC/PAGE | 5'-Amino modifier AL21A | |
| M13P296AC5 | NH2-AL21A-5'-CGACCTCGGTACCCGGGATCCTCTAGAGTCGACC-Cy5-N | 65.7 | 69.8 | 43 | 6235 | 1 umole | HPLC/PAGE | 5'-Amino modifier AL21A | 3'-Cy5-N |
| M13P296c | 5'-GGTCGACTCTAGAGGATCCCGGGTACCGAGGTCG | 65.7 | 69.8 | 43 | 6235 | 250 nmole | PAGE | | |
| M13P296cC3 | Cy3-5'-GGTCGACTCTAGAGGATCCCGGGTACCGAGGTCG | 65.7 | 69.8 | 43 | 6235 | 1 umole | HPLC/PAGE | 5'-Cy3 | |
| M13P141A | NH2-AL21A-5'-GTCGCCCTTTGTCTTCGCCCTCGTAAACATAT | 48.6 | 65.7 | 48.2 | 2692 | 1 umole | HPLC/PAGE | 5'-Amino modifier AL21A | |
| M13P257A | NH2-AL21A-5'-AGCTCCGCTCGATCTAACGAGGAAAGCACGTT | 51.4 | 67 | 39.8 | 5425 | 1 umole | HPLC/PAGE | 5'-Amino modifier AL21A | |
| M13P373 | 5'-CTACCCTCTCCGGCATTAATTATCAGCTAGAACG | 45.7 | 61.9 | 25.1 | 6951 | 250 nmole | PAGE | | |
| M13P373A | NH2-AL21A-5'-CTACCCTCTCCGGCATTAATTATCAGCTAGAACG | 45.7 | 61.9 | 25.1 | 6951 | 1 umole | HPLC/PAGE | 5'-Amino modifier AL21A | |
| M13P373AC5 | NH2-AL21A-5'-CTACCCTCTCCGGCATTAATTATCAGCTAGAACG-Cy5-N | 45.7 | 61.9 | 25.1 | 6951 | 1 umole | HPLC/PAGE | 5'-Amino modifier AL21A | 3'-Cy5-N |
| M13P357c | 5'-CGTTCTAGCTGATAAATTAATGCCGGAGAGGGTAG | 45.7 | 61.9 | 25.1 | 6951 | 250 nmole | PAGE | | |
| M13P373cC3 | Cy3-5'-CGTTCTAGCTGATAAATTAATGCCGGAGAGGGTAG | 45.7 | 61.9 | 25.1 | 6951 | 1 umole | HPLC/PAGE | 5'-Cy3 | |
| M13P104A | NH2-AL21A-5'-TACGCTAACTACTGAGGGCCGTGTGTGGAATGCTAC | 48.6 | 64.1 | 25.1 | 1719 | 1 umole | HPLC/PAGE | 5'-Amino modifier AL21A | |
| M13P225A | NH2-AL21A-5'-GTTCCTCAATTCTTTCAACTGTTGATTGCCAAC | 40 | 61.3 | 37 | 4768 | 1 umole | HPLC/PAGE | 5'-Amino modifier AL21A | |
| M13P123 | 5'-GCTTAATGACGATTATTGTTGTGAATATCAA | 25.7 | 55.6 | 16.1 | 2209 | 250 nmole | PAGE | | |
| M13P123A | NH2-AL21A-5'-GCTTTAATGACGATTATTGTTGTGAATATCAA | 25.7 | 55.6 | 16.1 | 2209 | 1 umole | HPLC/PAGE | 5'-Amino modifier AL21A | |
| M13P123AC5 | NH2-AL21A-5'-GCTTTAATGACGATTATTGTTGTGAATATCAA-Cy5-N | 25.7 | 55.6 | 16.1 | 2209 | 1 umole | HPLC/PAGE | 5'-Amino modifier AL21A | 3'-Cy5-N |
| M13P123c | 5'-TTGATATTCACAACAAATAATCCTCATTAAAGC | 25.7 | 55.6 | 16.1 | 2208 | 250 nmole | PAGE | | |
| M13P123cC3 | Cy3-5'-TTGATATTCACAACAAATAATCCTCATTAAAGC | 25.7 | 55.6 | 16.1 | 2209 | 1 umole | HPLC/PAGE | 5'-Cy3 | |
| M13P8A | NH2-AL21A-5'-TTGGGAATCAACTGTTATATGGAATGAAACTTCCA | 34.3 | 59.7 | 44.1 | 132 | 1 umole | HPLC/PAGE | 5'-Amino modifier AL21A | |
| M13P43A | NH2-AL21A-5'-GTTTAGTGTATTCTTTGCCTCTTGTTTAGG | 37.1 | 59.2 | 26.7 | 1212 | 1 umole | HPLC/PAGE | 5'-Amino modifier AL21A | |
| M13P172A | NH2-AL21A-5'-GCAAATAATTTGATATGGTAGGTTCTAACCGTTC | 34.3 | 57.8 | 42.5 | 4450 | 1 umole | HPLC/PAGE | 5'-Amino modifier AL21A | |

FIG. 5

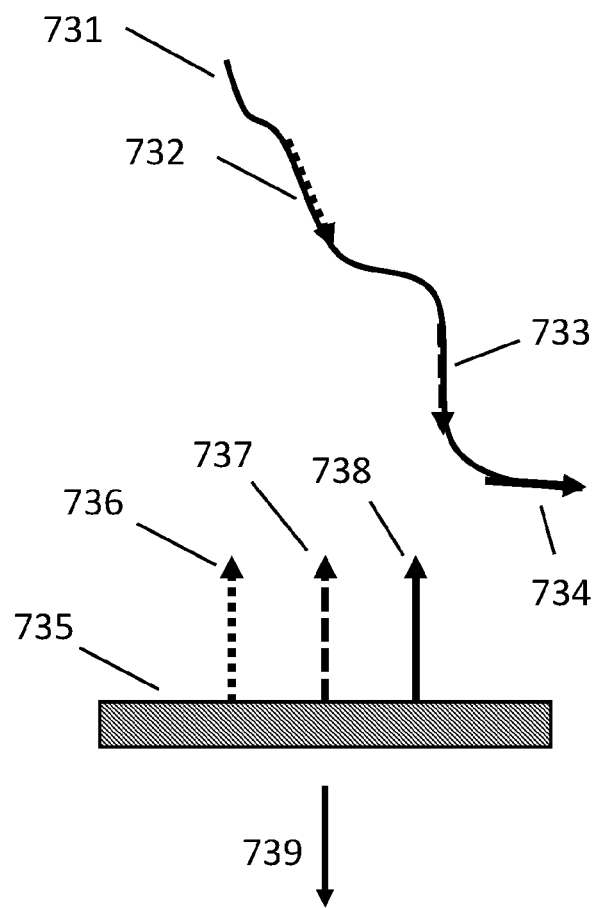
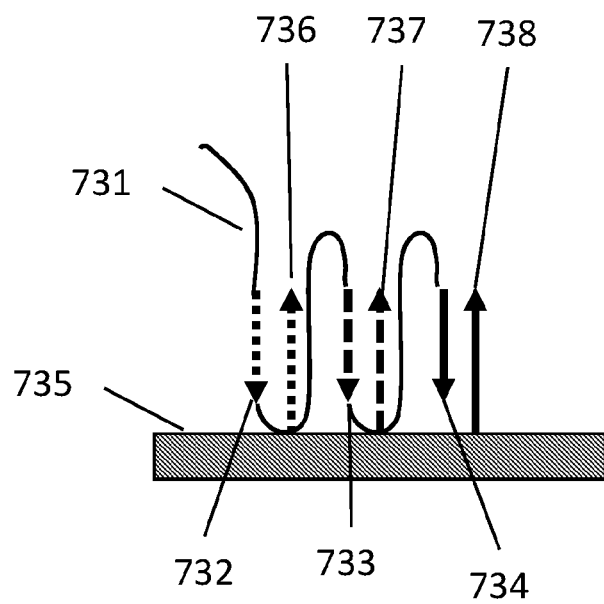
FIG. 7C

```
                          SEQUENCE LISTING

<160> NUMBER OF SEQ ID NOS: 13

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
cgagctcggt acccggggat cctctagagt cgacc                              35

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ggtcgactct agaggatccc cgggtaccga gctcg                              35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gtcgcccttt tgtctttggc gctggtaaac catat                              35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
agctcccgct ctgattctaa cgaggaaagc acgtt                              35

<210> SEQ ID NO 5
<211> LENGTH: 35
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 5
ctaccctctc cggcattaat ttatcagcta gaacg                                35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cgttctagct gataaattaa tgccggagag ggtag                                35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tacgctaact atgagggctg tctgtggaat gctac                                35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
cttcctcaat tcctttcaac tgttgatttg ccaac                                35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gctttaatga ggatttattt gtttgtgaat atcaa                                35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ttgatattca caaacaaata aatcctcatt aaagc                                35

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
```

```
        probe

<400> SEQUENCE: 11
ttgggaatca actgttatat ggaatgaaac ttcca                              35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
        probe

<400> SEQUENCE: 12
gttttagtgt attcttttgc ctctttcgtt ttagg                              35

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
        probe

<400> SEQUENCE: 13
gcaaataatt ttgatatggt aggttctaac ccttc                              35
```

SYSTEMS AND METHODS FOR IDENTIFYING AND DISTINGUISHING GENETIC SAMPLES

CROSS-REFERENCE

This application is a national stage entry of PCT/US2018/031636, filed on May 8, 2018, and claims the benefit of U.S. Provisional Application No. 62/503,502, filed May 9, 2017, U.S. Provisional Application No. 62/546,929, filed Aug. 17, 2017, and U.S. Provisional Application No. 62/586,760, filed Nov. 15, 2017, each of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Aug. 12, 2022, is named 50880_703_831_SL.txt and is 3,344 bytes in size.

BACKGROUND

DNA microarrays (or biochips) are often used to probe a sample for the presence of target nucleic acids. Microarrays involve an array of probes immobilized to a solid support. The array of probes can be organized as clusters of probes, each individually addressable. Each cluster can include multiple probes, each probe being identical to the other probes in each cluster, and each capable of binding to the same target nucleic acid sequence. After the sample is hybridized to the microarray, the presence of target nucleic acid bound to a probe can be determined. Microarrays can offer the advantages of being cost-effective, highly scalable in terms of being able to determine the presence of thousands to millions of sequences in a sample, and providing a faster time to answer than other similarly scaled approaches.

Standard microarrays must be carefully designed, requiring organization of probes in specific positions on the array in order to maximize detection potential. Detection can therefore be problematic when examining a complex sample, one that includes more than one source of genetic material, such as an environmental sample. Pooling of probes, without being confined by requirements for specific probe organization, provides flexibility in the type of detection platforms which can be used. The methods and systems herein describe novel detection systems for the identification and distinction of subjects in a complex sample using pooled probes.

SUMMARY

Disclosed herein, in certain embodiments, are methods comprising: (a) providing a sample comprising an analyte; and (b) concentrating or transporting said analyte by isotachophoresis (ITP) in a channel; wherein a surface of said channel comprises a silicon substrate. In some cases, said silicon substrate comprises an insulating layer. In some cases, said insulating layer comprises silicon oxide. In some cases, said insulating layer is at least about 250 nanometers thick. In some cases, said insulating layer is at least about 500 nanometers thick.

In some embodiments, said surface comprises at least one well. In some cases, said at least one well is a microwell. In some cases, said at least one well comprises an array of wells. In some cases, probes are coupled to said surface. In some cases, said probes are arranged in an array. In some cases, probes in a single feature of said array comprise at least two species of probe.

In some embodiments, said at least two species of probe are each specific to a same subject. In some cases, said subject comprises a species of organism. In some cases, said subject comprises a strain of organism. In some cases, said subject comprises a clade of organism. In some cases, said subject comprises a genetic variant. In some cases, said subject comprises a trait of pathogenicity. In some cases, said subject comprises a trait of resistance. In some cases, said subject comprises an individual member of a species of organism.

In some embodiments, said ITP is conducted at a voltage of equal to or less than about 800 volts. In some embodiments, said ITP is conducted at a voltage of equal to or less than about 400 volts. In some embodiments, said ITP is conducted at a voltage of equal to or less than about 200 volts. In some embodiments, said channel has a height of equal to or less than 100 micrometers. In some embodiments, said channel has a height of equal to or less than 75 micrometers. In some embodiments, said channel has a height of equal to or less than 50 micrometers. In some embodiments, said channel has a height of equal to or less than 25 micrometers. In some embodiments, said channel does not comprise a constriction or tapered section. In some embodiments, said channel has a width of equal to or less than 2000 micrometers. In some embodiments, said channel has a width of equal to or less than 1000 micrometers. In some embodiments, said channel has a width of equal to or less than 500 micrometers.

In some embodiments, said analyte comprises nucleic acid. In some cases, said analyte comprises DNA. In some cases, said analyte comprises RNA. In some cases, the method further comprises binding said analyte to a probe on said surface. In some cases, the method further comprises comprising detecting said analyte. In some cases, the method further comprises binding said analyte to a probe on said surface and detecting said analyte, wherein said method is conducted in equal to or less than about 60 minutes. In some cases, the method further comprises binding said analyte to a probe on said surface and detecting said analyte, wherein said method is conducted in equal to or less than about 45 minutes. In some cases, the method further comprises binding said analyte to a probe on said surface and detecting said analyte, wherein said method is conducted in equal to or less than about 30 minutes. In some cases, the method further comprises binding said analyte to a probe on said surface and detecting said analyte, wherein said method is conducted in equal to or less than about 15 minutes. In some cases, the method further comprises binding said analyte to a probe on said surface and detecting said analyte, wherein said method is conducted in equal to or less than about 5 minutes.

Disclosed herein, in certain embodiments, are detection devices comprising one or more sets of probes, wherein each set of said one or more sets of probes comprises a plurality of probes, wherein each of said plurality of probes comprises one or more subject-specific features, and wherein each set of said one or more sets of probes binds to a target nucleic acid from a different subject of a plurality of different subjects, wherein the one or more sets of probes are pooled.

In some embodiments, at least two of said plurality of probes within a set of probes are identical. In some embodiments, at least two of said plurality of probes within a set of probes are different. In some embodiments, each set of said plurality of probes comprises a plurality of unique probes. In some embodiments, each set of said plurality of probes comprises an average representation of said plurality of unique probes. In some embodiments, said average representation of said plurality of unique probes is controlled by limiting the total number of probes within at least one set of said one or more sets of probes, by mixing said plurality of unique probes at a predefined ratio, or a combination of both. In some embodiments, at least one of said one or more sets of probes comprises about 2-1000 unique probes. In some embodiments, said average representation comprises about 2-1000 representations of at least one of said plurality of unique probes within said set of probes.

In some embodiments, subject-specific features within at least one set of probes are identical. In some embodiments, at least one set of said one or more sets of probes comprises a different subject-specific feature. In some embodiments, at least one set of said one or more sets of probes is individually addressable. In some embodiments, at least one of said plurality of probes within a set of probes is complementary to an identical nucleic acid sequence present on said target nucleic acid. In some embodiments, at least two of said plurality of probes within a set of probes is complementary to a different nucleic acid sequence present on said target nucleic acid. In some embodiments, at least one set of said one or more sets of probes is complementary to unique regions of a genome of a subject. In some embodiments, said unique regions of a genome of a subject are not represented in a genome of a different subject. In some embodiments, said plurality of different subjects comprises a plurality of different cell-types. In some embodiments, at least one set of said one or more sets of probes binds to a target nucleic acid from a different cell-type of said plurality of different cell-types. In some embodiments, said plurality of different subjects comprises a plurality of different genes, genomic regions, organisms, individuals, or strains. In some embodiments, at least one set of said one or more sets of probes binds to a target nucleic acid from a different organism of said plurality of different organisms. In some embodiments, said plurality of probes comprises nucleic acid molecules. In some embodiments, at least one set of said one or more sets of probes is immobilized on a surface of the detection device. In some embodiments, said surface is a bead. In some embodiments, at least one set of said one or more sets of probes is not immobilized on a surface of the detection device. In some embodiments, said subject-specific feature comprises one or more genetic features. In some embodiments, said one or more genetic features are selected from the group consisting of: a genome, chromatin, a chromosome, a chromosome locus, a chromosomal material, an allele, a gene, a gene cluster, a gene locus, a genetic polymorphism, a genetic mutation, a nucleotide, a single nucleotide polymorphism (SNP), a restriction fragment length polymorphism (RFLP), a variable tandem repeat (VTR), a copy number variant (CNV), a microsatellite sequence, a genetic marker, a sequence marker, a sequence tagged site (STS), a plasmid, a transcription unit, a transcription product, a genetic expression state, a conserved region, a pathogenicity island (PIA), and any combination thereof. In some embodiments, at least one set of said one or more sets of probes comprises more than 100 sets of probes. In some embodiments, at least one set of said one or more sets of probes comprises about 50-1000 probes. In some embodiments, at least one of the plurality of probes comprise a target-specific guide nucleic acid (gNA): nucleic acid-guided nuclease system complex.

In some embodiments, the one or more sets of probes are pooled in a reaction chamber. In some embodiments, the reaction chamber is a PCR well, an array spot, a droplet, an electrode, or a microfluidic channel. In some embodiments, the detection device further comprises a plurality of reaction chambers. In some embodiments, the electrode comprises gold, iridium, platinum, copper, or a combination thereof. In some embodiments, the reaction chamber comprises at least one pore. In some embodiments, at least one of the plurality of probes is labeled with a detectable label. In some embodiments, the detectable label is selected from the group consisting of an enzyme, an enzyme substrate, an antibody, an antigen binding fragment, a peptide, a chromophore, a lumiphore, a fluorophore, a chromogen, a hapten, an antigen, a radioactive isotope, a magnetic particle, a nanoparticle, quantum dots, a barcode, an active site, a binding site, a redox active marker group, an aptamer, a hydrophobic specie, a hydrophilic specie, one member of a binding pair, a donor dye (reporter), an acceptor dye (quencher), an organometallic compound, and combinations thereof.

In some embodiments, the detection device further comprises one or more sets of secondary probes, wherein each set of said one or more sets of secondary probes comprises a plurality of secondary probes, and wherein each set of said one or more sets of secondary probes binds to a region of a nucleic acid near the target nucleic acid. In some embodiments, the region of the nucleic acid near the target nucleic acid is upstream or downstream of the target nucleic acid. In some embodiments, the region of the nucleic acid near the target nucleic acid is separated from the target nucleic acid by less than 10 bp. In some embodiments, the region of the nucleic acid near the target nucleic acid is separated from the target nucleic acid by less than 10 bp, less than 20 bp, less than 30 bp, less than 40 bp, less than 50 bp, or less than 100 bp. In some embodiments, at least one of said one or more sets of secondary probes is not immobilized on a surface of the detection device. In some embodiments, at least one of said one or more sets of secondary probes is immobilized on a surface of the detection device. In some embodiments, at least one of said one or more sets of secondary probes is labeled with a detectable label. In some embodiments, the label is selected from the group consisting of an enzyme, an enzyme substrate, an antibody, an antigen binding fragment, a peptide, a chromophore, a lumiphore, a fluorophore, a chromogen, a hapten, an antigen, a radioactive isotope, a magnetic particle, a nanoparticle, quantum dots, a barcode, an active site, a binding site, a redox active marker group, an aptamer, a hydrophobic specie, a hydrophilic specie, one member of a binding pair, a donor dye (reporter), an acceptor dye (quencher), an organometallic compound, and combinations thereof. In some embodiments, at least one of the plurality of secondary probes is a target-specific guide nucleic acid (gNA): nucleic acid-guided nuclease system protein complex. In some embodiments, the one or more sets of secondary probes are one or more sets of capture probes. In some embodiments, the detection device is a single-use device.

Disclosed herein, in certain embodiments, are methods comprising (a) providing a sample comprising a plurality of nucleic acids derived from a plurality of different subjects; (b) hybridizing said plurality of nucleic acids to a detection device, wherein said detection device comprises one or more sets of probes, wherein the one or more sets of probes are pooled, wherein each set of said one or more sets of probes comprises a plurality of probes, wherein each of said plurality of probes comprises one or more subject-specific feature and wherein each set of said one or more sets of probes binds to said at least one target nucleic acid from at least two of said plurality of different subjects of said plurality of different subjects; (c) detecting a signal associated with binding of said at least one target nucleic acid to a probe of said plurality of probes; and (d) identifying said plurality of different subjects based on a presence of said at least one target nucleic acid in said sample. In some embodiments, the method further comprises, prior to step a), extracting said plurality of nucleic acids from said plurality of different subjects. In some embodiments, the method further comprises, prior to step b), fragmenting said plurality of nucleic acids. In some embodiments, the method further comprises, prior to step b), amplifying said plurality of nucleic acids. In some embodiments, said plurality of nucleic acids are not amplified. In some embodiments, the method further comprises providing one or more reports identifying said plurality of different subjects.

In some embodiments, said plurality of different subjects comprises a plurality of different cell types. In some embodiments, said plurality of different subjects comprises a plurality of different organisms. In some embodiments, at least two of said plurality of probes within a set of probes are identical. In some embodiments, at least two of said plurality of probes within a set of probes are different. In some embodiments, each set of said plurality of probes comprises a plurality of unique probes. In some embodiments, each set of said plurality of probes comprises an average representation of said plurality of unique probes. In some embodiments, said average representation of said plurality of unique probes is controlled by limiting the total number of probes within at least one set of said one or more sets of probes, by mixing said plurality of unique probes at a predefined ratio, or a combination of both. In some embodiments, at least one of said one or more sets of probes comprises about 2-1000 unique probes. In some embodiments, said average representation comprises about 2-1000 representations of at least one of said plurality of unique probes within said set of probes.

In some embodiments, subject-specific features within at least one set of probes are identical. In some embodiments, at least one set of said one or more sets of probes comprises a different subject-specific feature. In some embodiments, at least one set of said one or more sets of probes is individually addressable. In some embodiments, at least one of said plurality of probes within a set of probes is complementary to an identical nucleic acid sequence present on said target nucleic acid. In some embodiments, at least one of said plurality of probes within a set of probes is complementary to a different nucleic acid sequence present on said target nucleic acid. In some embodiments, at least one set of said one or more sets of probes is complementary to unique regions of a genome of a subject. In some embodiments, said unique regions of a genome of a subject are not represented in a genome of a different subject. In some embodiments, said plurality of probes comprise nucleic acid molecules. In some embodiments, at least one set of said one or more sets of probes is immobilized on a surface of the detection device. In some embodiments, the surface is a bead. In some embodiments, at least one set of said one or more sets of probes is not immobilized on a surface of the detection device. In some embodiments, said subject-specific feature comprises one or more genetic features. In some embodiments, said one or more genetic features are selected from the group consisting of: a genome, chromatin, a chromosome, a chromosome locus, a chromosomal material, an allele, a gene, a gene cluster, a gene locus, a genetic polymorphism, a genetic mutation, a nucleotide, a single nucleotide polymorphism (SNP), a restriction fragment length polymorphism (RFLP), a variable tandem repeat (VTR), a copy number variant (CNV), a microsatellite sequence, a genetic marker, a sequence marker, a sequence tagged site (STS), a plasmid, a transcription unit, a transcription product, a genetic expression state, a conserved region, a pathogenicity island (PIA), and any combination thereof In some embodiments, at least one set of said one or more sets of probes comprises more than 100 sets of probes. In some embodiments, least one set of said one or more sets of probes comprises about 50-1000 probes. In some embodiments, said at least one target nucleic acid is labeled with a detectable label. In some embodiments, said detectable label comprises a fluorescent dye. In some embodiments, said at least one target nucleic acid is labeled by hybridization of a detection probe comprising said detectable label to said at least one target nucleic acid. In some embodiments, a first probe of said plurality of probes comprises a first subject-specific feature and a second probe of said plurality of probes comprises a second subject-specific feature, and wherein said first probe and said second probe hybridize to said at least one target nucleic acid. In some embodiments, at least one of the plurality of probes is labeled with a detectable label. In some embodiments, the detectable label is selected from the group consisting of an enzyme, an enzyme substrate, an antibody, an antigen binding fragment, a peptide, a chromophore, a lumiphore, a fluorophore, a chromogen, a hapten, an antigen, a radioactive isotope, a magnetic particle, a nanoparticle, quantum dots, a barcode, an active site, a binding site, a redox active marker group, an aptamer, a hydrophobic specie, a hydrophilic specie, one member of a binding pair, a donor dye (reporter), an acceptor dye (quencher), an organometallic compound, and combinations thereof In some embodiments, at least one of the plurality of probes is a target-specific guide nucleic acid (gNA): nucleic acid-guided nuclease system protein complex.

In some embodiments, the one or more sets of probes are pooled in a reaction chamber. In some embodiments, the reaction chamber is a PCR well, an array spot, a droplet, an electrode, or a microfluidic channel. In some embodiments, the detection device of the method further comprises a plurality of reaction chambers. In some embodiments, the electrode comprises gold, iridium, platinum, copper, or a combination thereof. In some embodiments, the reaction chamber comprises at least one pore. In some embodiments, prior to the hybridizing, the plurality of nucleic acids is concentrated. In some embodiments, the plurality of nucleic acids is concentrated using isotachophoresis.

In some embodiments, the detection device further comprises one or more sets of secondary probes, wherein each set of said one or more sets of secondary probes comprises a plurality of secondary probes, and wherein each set of said one or more sets of secondary probes binds to a region of a nucleic acid near the target nucleic acid. In some embodiments, the region of the nucleic acid near the target nucleic acid is upstream or downstream of the target nucleic acid. In some embodiments, the region of the nucleic acid near the target nucleic acid is separated from the target nucleic acid by less than 10 bp. In some embodiments, the region of the nucleic acid near the target nucleic acid is separated from the target nucleic acid by less than 10 bp, less than 20 bp, less than 30 bp, less than 40 bp, less than 50 bp, or less than 100 bp. In some embodiments, at least one set of the one or more sets of secondary probes is not immobilized on a surface of the detection device. In some embodiments, at least one set of the one or more sets of secondary probes is immobilized on a surface of the detection device. In some embodiments, at least one of the one or more sets of secondary probes comprise a label. In some embodiments, the label is selected from the group consisting of an enzyme, an enzyme substrate, an antibody, an antigen binding fragment, a peptide, a chromophore, a lumiphore, a fluorophore, a chromogen, a hapten, an antigen, a radioactive isotope, a magnetic particle, a nanoparticle, quantum dots, a barcode, an active site, a binding site, a redox active marker group, an aptamer, a hydrophobic specie, a hydrophilic specie, one member of a binding pair, a donor dye (reporter), an acceptor dye (quencher), an organometallic compound, and combinations thereof. In some embodiments, at least one of the plurality of secondary probes is a target-specific guide nucleic acid (gNA): nucleic acid-guided nuclease system complex. In some embodiments, one or more sets of secondary probes are one or more sets of capture probes.

In some embodiments, the method further comprises exposing the detection device to a light source. In some embodiments, the method further comprises performing polymerase chain reaction (PCR) of a nucleic acid sequence comprising the target nucleic acid. In some embodiments, the method further comprises applying a voltage to the detection device. In some embodiments, the signal is a fluorescence signal, an electrochemical signal, or a measure of current impedance.

BRIEF DESCRIPTION OF THE DRAWINGS

FIG. 1A depicts four exemplary features, each feature comprising identical probes and four unbound labeled targets from a single subject in a sample. FIG. 1B depicts a subject specific feature with four probes and four unbound labeled targets from a single subject in a sample. FIG. 1C depicts the four targets bound to four different features. FIG. 1D depicts the four targets bound to a single subject specific feature. Comparing FIG. 1C to FIG. 1D demonstrates the signal amplification that can occur on a single feature when using a plurality of different probes directed at multiple subject targets. FIG. 1E depicts features with ordered pooling of unique probes within one distinct feature. FIG. 1F depicts features with random pooling of unique probes among features.

FIG. 2 depicts the relative signal that can be obtained by increasing the number of fluorophores which bind per feature.

FIG. 5 depicts examples of unique probes designed against the M13mp18 phage vector sequence using the methods described herein. Figure discloses SEQ ID NOS 1, 1, 1, 2,2-5, 5, 5, 6, 6-9, 9, 9, 10, and 10-13, respectively, in order of appearance.

FIG. 7C depicts hybridization of a target nucleic acid to an array via multiple hybridization sequences.

FIG. 12 also illustrates the ability to differentiate between the two Staph strains.

FIG. 14A shows fluorescently labeled sample DNA exiting an inlet port. FIG. 14B shows the DNA band beginning to focus in a flow cell channel. FIG. 14C shows a focused DNA band formed in the flow cell channel. FIG. 14D shows the DNA band entering a "throat" of the tapered section of the flow cell channel. FIG. 14E shows the DNA band moving through the throat. FIG. 14F shows the DNA band approaching the end of the throat. FIG. 14G shows the DNA band entering an array hybridization region of the flow cell channel. FIG. 14H shows the DNA band in the hybridization region of the flow cell channel.

DETAILED DESCRIPTION

Definitions

Figure 1A:
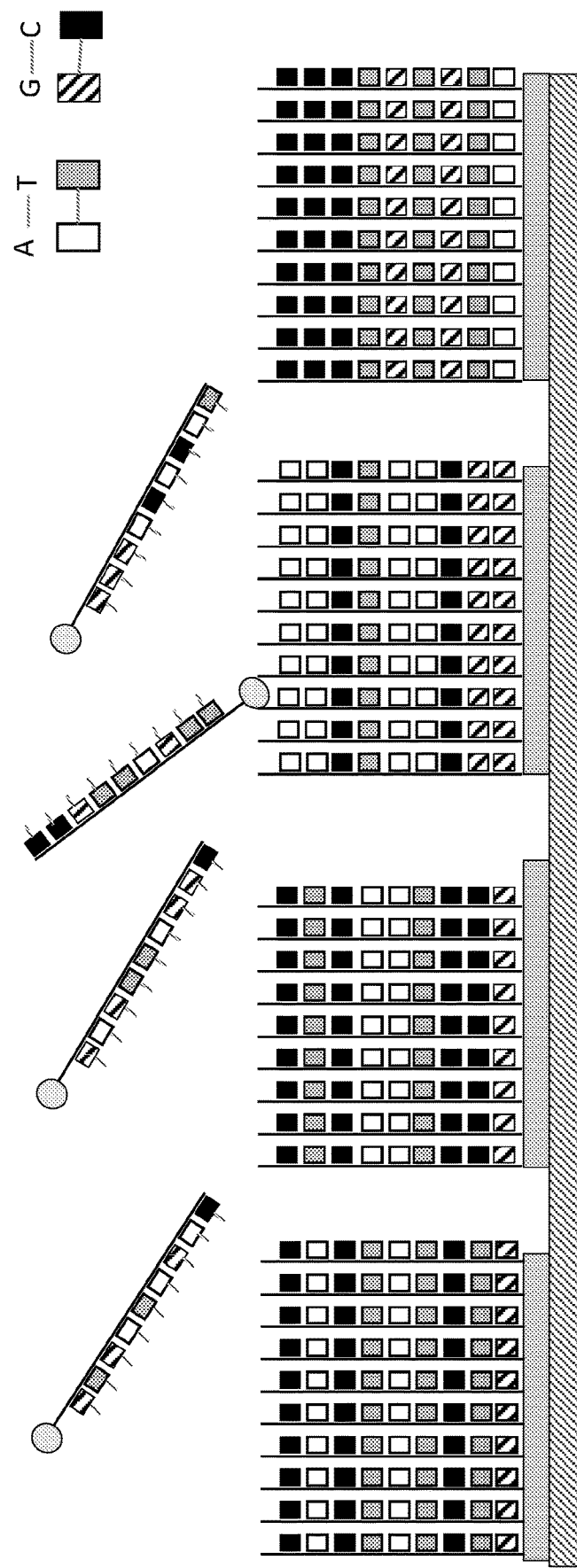
FIG. 1A-FIG. 1F illustrate an embodiment of a biochip system.

The below terms are discussed to illustrate meanings of the terms as used in this specification, in addition to the understanding of these terms by those of skill in the art. As used in the specification and claims, the singular forms "a", "an" and "the" can include plural references unless the context clearly dictates otherwise. For example, the term "a cell" can include a plurality of cells, including mixtures thereof.

As used herein, the term "epigenome" refers to changes to genetic material, or the protein expression of genetic material, that are not reflected at the sequence level such as DNA methylation and chromatin restructuring or remodeling. The "transcriptome" refers to the entirety of gene transcripts (mRNA) synthesized by an organism under certain environmental conditions. A transcriptome data set includes, without limitation, qualitative and quantitative information as to the activation or deactivation of expression of a gene of interest. Transcriptome also includes RNA transcripts that do not code for proteins (non-coding RNA or ncRNA) including microRNAs, piwiRNA, structural RNAs, RNA that binds to proteins, telomerase RNA, and transposon RNA. The "exome" refers to the part of the genome formed by exons, the sequences which, when transcribed, remain within the mature RNA. "Microbiome" refers to the entirety of the genomes within a biological sample, regardless of the species, usually microbial in origin.

As used herein, the term "genetic feature" refers to any genome, genotype, haplotype, chromatin, chromosome, chromosome locus, chromosomal material, deoxyribonucleic acid (DNA), allele, gene, gene cluster, gene locus, genetic polymorphism, genetic mutation, genetic mutation rate, nucleotide, nucleotide base pair, single nucleotide polymorphism (SNP), restriction fragment length polymorphism (RFLP), variable tandem repeat (VTR), copy number variant (CNV), microsatellite sequence, genetic marker, sequence marker, sequence tagged site (STS), plasmid, transcription unit, transcription product, gene expression level, genetic expression (e.g., transcription) state, ribonucleic acid (RNA), complementary DNA (cDNA), conserved region, and pathogenicity island, including the nucleotide sequence and encoded amino acid sequence associated with any of the above. An epigenetic feature is any feature of genetic material—all genomic, vector and plasmid DNA and chromatin—that affects gene expression in a manner that is heritable during somatic cell divisions and sometimes heritable in germline transmission, but that is non-mutational to the DNA sequence and is therefore fundamentally reversible, including but not limited to methylation of DNA nucleotides and acetylation of chromatin-associated histone proteins. As used herein, therefore, genetic sequence data can include, without limitation, nucleotide sequences, deoxyribonucleic acid (DNA) sequences, and ribonucleic acid (RNA) sequences.

The term "subject-specific feature" as used herein can refer to any feature or attribute that is capable of distinguishing one subject from another. In some cases, a subject-specific feature is a genetic feature. The genetic feature, as described above, can be present on a nucleic acid isolated from a subject. In some cases, a subject-specific feature can relate to a feature or features that distinguish a set of functions. This could be accomplished, for example, by designing probes to target a single gene, a plurality of genes, or genomic regions with known epigenomic functions such as promoter regions. A subject-specific feature can be represented as a probe on a detection device. The probes representing the subject-specific feature can be capable of binding to one or more target nucleic acid sequences obtained from a subject. In some cases, the subject-specific feature comprises a plurality of non-identical probes, each capable of distinguishing a subject from another. In some cases, at least two species of probes are each specific to a same subject. In some cases, a specific subject, such as a strain of a microbe, can be distinguished by one or multiple features on a detection device, including features that are unique to the target strain, unique to the species containing the strain, contained in conserved regions that exist in the strain, or that recognize pathogenicity islands contained within the strain. In some cases, it can be valuable to identify simply pathogenicity islands, as this can indicate that a subject requires more testing.

The term "assembly" can be any computational process in which sequence strings produced by a sequencer or mass spectrometer are merged between one another with the objective to reconstruct the original sequence string, from which the set of all sequence strings were derived. In some instances, an assembly is from an individual organism. In some instances, multiple individuals are can be used to create an assembly. In some instances, an assembly is created de novo, without the use of a reference sequence. In some instances, an assembly is created using a reference sequence. The reference sequence can be a genome from the same species. The reference genome can be a genome from a closely related species.

The term "subject", as used herein, generally refers to a specific source of genetic materials. The subject can be a biological entity. The biological entity can be a plant, animal, or microorganism, including, e.g., bacteria, viruses, fungi, and protozoa. The subject can be an organ, tissue, or cell. A subject can be obtained in vivo or cultured in vitro. The subject can be a cell line. The subject can be propagated in culture. The subject can be disease cells. The subject can be cancer cells. The subject can be a mammal. The mammal can be a human. The subject can mean an individual representation of the specific source of genetic material (e.g. the subject can be a particular individual human or a particular bacterial strain). Alternatively, the subject can be a general representation of a kind of specific source of genetic materials, e.g. the subject can be any and all members of a single species. The subject can also be a portion of a genome, for example if the sample does not contain a full genome.

The term "pooled" as used herein can refer to grouping together or mixing of non-identical probes prior to hybridization to a sample. The non-identical probes can be part of the same set of probes. Alternatively, the probes from two or more sets of probes can be pooled. Pooled probes can be mixed in equal or unequal amounts.

A "sample" or "nucleic acid sample" can refer to any substance containing or presumed to contain nucleic acid. The sample can be a biological sample obtained from a subject. The nucleic acids can be RNA, DNA, e.g., genomic DNA, mitochondrial DNA, viral DNA, synthetic DNA, or cDNA reverse transcribed from RNA. The nucleic acids in a nucleic acid sample can serve as templates for extension of a hybridized primer. In some cases, the biological sample is a liquid sample. The liquid sample can be, for example, whole blood, plasma, serum, ascites, semen, cerebrospinal fluid, sweat, urine, tears, saliva, buccal sample, cavity rinse, or organ rinse. The liquid sample can be an essentially cell-free liquid sample (e.g., plasma, serum, sweat, urine, tears, etc.). In other cases, the biological sample is a solid biological sample, e.g., feces, hair, nail, or tissue biopsy, e.g., a tumor biopsy. A sample can also comprise in vitro cell culture constituents (including but not limited to conditioned medium resulting from the growth of cells in cell culture medium, recombinant cells and cell components). A sample can comprise or be derived from cancer cells. A sample can comprise a microbiome.

A "complex sample" as used herein refers to a sample that includes two or more subjects or that includes material (e.g., nucleic acids) from two or more subjects. A complex sample can comprise genetic material from two or more subjects. A complex sample can comprise nucleic acid molecules from two or more subjects. A complex sample can comprise nucleic acids from two or more strains of bacteria, viruses, fungi and the like. A complex sample can comprise two or more resolvable subjects (i.e., two or more subjects that are distinguishable from one another). In some cases, complex samples can be obtained from the environment. For example, a complex sample can be an air sample, a soil or dirt sample or a water sample (e.g., river, lake, ocean, wastewater, etc.). Environmental samples can comprise one or more species of bacteria, viruses, protozoans, algae, fungi and the like. A complex sample can comprise cell free DNA.

"Nucleotides" can be biological molecules that can form nucleic acids. Nucleotides can have moieties that contain not only the known purine and pyrimidine bases, but also other heterocyclic bases that have been modified. Such modifications include methylated purines or pyrimidines, acylated purines or pyrimidines, alkylated riboses, or other heterocycles. In addition, the term "nucleotide" includes those moieties that contain hapten, biotin, or fluorescent labels and can contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the like.

"Nucleotides" can also include locked nucleic acids (LNA) or bridged nucleic acids (BNA). BNA and LNA generally refer to modified ribonucleotides wherein the ribose moiety is modified with a bridge connecting the 2' oxygen and 4' carbon. Generally, the bridge "locks" the ribose in the 3'-endo (North) conformation, which is often found in the A-form duplexes. The term "locked nucleic acid" (LNA) generally refers to a class of BNAs, where the ribose ring is "locked" with a methylene bridge connecting the 2'-O atom with the 4'-C atom. LNA nucleosides containing the six common nucleobases (T, C, G, A, U and mC) that appear in DNA and RNA are able to form base-pairs with their complementary nucleosides according to the standard Watson-Crick base pairing rules. Accordingly, BNA and LNA nucleotides can be mixed with DNA or RNA bases in an oligonucleotide whenever desired. The locked ribose conformation enhances base stacking and backbone pre-organization. Base stacking and backbone pre-organization can give rise to an increased thermal stability (e.g., increased Tm) and discriminative power of duplexes. LNA can discriminate single base mismatches under conditions not possible with other nucleic acids.

The terms "polynucleotides", "nucleic acid", "nucleotides" and "oligonucleotides" can be used interchangeably. They can refer to a polymeric form of nucleotides of any length, either deoxyribonucleotides or ribonucleotides, or analogs thereof. Polynucleotides can have any three-dimensional structure, and can perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component.

A "variant" can be an alteration in the normal sequence of a nucleic acid sequence (e.g., a gene). In some instances, a genotype and corresponding phenotype is associated with a variant. In other instances, there is no known function of a variant. A variant can be a SNP. A variant can be a SNV. A variant can be an insertion of a plurality of nucleotides. A variant can be a deletion of a plurality of nucleotides. A variant can be a mutation. A variant can be a copy number variation. A variant can be a structural variant. A variant can be a nucleic acid deviation between two or more individuals in a population.

The term "target polynucleotide" or "target nucleic acid" as used herein, generally refers to a polynucleotide of interest under study. In certain cases, a target polynucleotide contains one or more sequences that are of interest and under study. A target polynucleotide can comprise, for example, a genomic sequence. The target polynucleotide can comprise a target sequence whose presence, amount, and/or nucleotide sequence, or changes in these, are desired to be determined. A target polynucleotide can comprise non-coding regions of a genome.

The term "genome" can refer to the genetic complement of a biological organism, and the terms "genomic data" and "genomic data set" include sequence information of chromosomes, genes, or DNA of the biological organism.

The term "genomic data," as used herein, refers to data that can be one or more of the following: the genome or exome sequence of one or more, or any combination or mixture of one or more, mitochondria, cells, including eggs and sperm, tissues, neoplasms, tumors, organs, organisms, microorganisms, viruses, individuals, or cell free DNA, and further including, but not limited to, nucleic acid sequence information, genotype information, gene expression information, genetic data, epigenetic information including DNA methylation, acetylation or similar DNA modification data, RNA transcription, splicing, editing or processing information, or medical, health or phenotypic data, or nutritional, dietary or environmental condition or exposure information or other attribute data of any microorganism, virus, cell, tissue, neoplasm, tumor, organ, organ system, cell-free sample (e.g. serum or media), individual or group of samples or individuals. Accordingly, the term "genomic sequence," as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome. "Genomic sequence" can also be a sequence that occurs on the cytoplasm or in the mitochondria.

The terms "determining," "measuring," "evaluating," "assessing," "assaying," and "analyzing" can be used interchangeably herein to refer to any form of measurement, and can include determining if an element is present or not. These terms can include both quantitative and/or qualitative determinations. Assessing can be relative or absolute. "Assessing the presence of can include determining the amount of something present, as well as determining whether it is present or absent.

The term "genomic fragment", as used herein, can refer to a region of a genome, e.g., an animal or plant genome such as the genome of a human, monkey, rat, fish or insect or plant. A genomic fragment may or may not be adaptor ligated. A genomic fragment can be adaptor ligated (in which case it has an adaptor ligated to one or both ends of the fragment, to at least the 5' end of a molecule), or non-adaptor ligated.

The term "barcode" as used herein, generally refers to a sequence of nucleotides that can encode information about an assay. In some instances, barcodes are unique. A barcode sequence can encode information relating to the identity of an interrogated allele, identity of a target polynucleotide or genomic locus, identity of a sample, a subject, or any combination thereof. A barcode sequence can be a portion of a primer, a reporter probe, or both. A barcode sequence can be at the 5'-end or 3'-end of an oligonucleotide, or can be located in any region of the oligonucleotide. Barcode sequences can be non-naturally occurring, e.g. sequences which do not occur in the sample under study. In other instances, naturally occurring sequences can be used as barcodes or as a part of a barcode sequence. In some instances, junctions, where nucleic acids have been joined can serve as bar codes. In some instances, sequencing adaptors can serve as barcodes or as a part of barcodes. In some instances, the barcodes are in excess of a target molecule, e.g. a genomic sequence of interest. In some instances, a barcode is associated with a target molecule randomly or semi-randomly. In some instances, a barcode is associated with a target molecule by design.

The term "mutation", as used herein, generally refers to a change of the nucleotide sequence of a genome. Mutations can involve large sections of DNA (e.g., copy number variation). Mutations can involve whole chromosomes (e.g., aneuploidy). Mutations can involve small sections of DNA. Examples of mutations involving small sections of DNA include, e.g., point mutations or single nucleotide polymorphisms, multiple nucleotide polymorphisms, insertions (e.g., insertion of one or more nucleotides at a locus), multiple nucleotide changes, deletions (e.g., deletion of one or more nucleotides at a locus), and inversions (e.g., reversal of a sequence of one or more nucleotides).

The term "locus", as used herein, can refer to a location of a gene, nucleotide, or sequence on a chromosome. An "allele" of a locus, as used herein, can refer to an alternative form of a nucleotide or sequence at the locus. A "wild-type allele" generally refers to an allele that has the highest frequency in a population of subjects. A "wild-type" allele generally is not associated with a disease. A "mutant allele" generally refers to an allele that has a lower frequency that a "wild-type allele" and can be associated with a disease. A "mutant allele" may not have to be associated with a disease. The term "interrogated allele" generally refers to the allele that an assay is designed to detect.

The term "single nucleotide polymorphism", or "SNP", as used herein, generally refers to a type of genomic sequence variation resulting from a single nucleotide substitution within a sequence. "SNP alleles" or "alleles of a SNP" generally refer to alternative forms of the SNP at particular locus. The term "interrogated SNP allele" generally refers to the SNP allele that an assay is designed to detect.

Disclosed herein are methods and systems for a novel detection device that has the capability to identify one or more subjects in a sample, or to identify important characteristics about a subject, such as for example pathogenicity, virulence, or antibiotic resistance. The detection device can comprise a plurality of probes that comprise one or more subject-specific features. The term "subject-specific feature" as used herein refers to a plurality of probes that can distinguish and identify one subject from another. In some aspects of the invention, subject-specific features can be utilized to identify a subject present in a complex sample.

The subject can be a species of organism, a strain of organism, a clade of organism, a genetic variant, a trait of pathogenicity, a trait of resistance, or an individual member of a species of organism. A complex sample can be any sample, biological or otherwise, that contains material from more than one subject (i.e., two or more subjects). In some cases, the subject is an organism such as a virus, a bacterium, a protozoan, a fungus and the like. In other cases, the subject is a tissue, an organ or a cell derived therefrom. The tissue, organ or cell can be derived from an animal, such as a human. The complex sample can include a plurality of cell types. In some cases, the complex sample can include a tissue biopsy, such as a tumor biopsy. In some examples, a complex sample includes two or more strains of a microorganism (e.g., bacteria, virus, fungus and the like). In other examples, a complex sample includes two or more species of an organism. The organism can be a microorganism. In some cases, a complex sample comprises material, such as nucleic acids, from two or more subjects. The subject-specific features can be used to determine the identity of the one or more subjects present in the complex sample. The methods and systems herein are not limited to any one type of complex sample. The important aspect is that the complex sample includes more than one subject with at least one distinguishable feature.

The complex sample can include a mixture of nucleic acids. The nucleic acids can be derived from the more than one subject. Any method of generating a sample of nucleic acids is permissible by the present disclosure. In some cases, a complex sample that includes biological cells is obtained and the biological cells are subsequently lysed to release the nucleic acids from the cells. Nucleic acids can also be released from biological cells by physical methods. In other cases, cell-free nucleic acids are obtained. Cell-free nucleic acids can be obtained from a human or an animal, for example, from the blood. Cell-free nucleic acids can also be obtained from the environment, for example, nucleic acids released from an organism into the environment. The cell-free nucleic acids can be, for example, derived from the capsid of a virus or from a pathogen contained within a spore. In some embodiments, the complex sample is selected from the group consisting of a clinical sample, a forensic sample, an environmental sample, a metagenomic sample, and a food sample. In some embodiments, the complex sample is from a human.

The nucleic acids within the complex sample can comprise target nucleic acid sequences. The target nucleic acid sequences can be nucleic acid sequences that distinguish one subject from another. For example, the target nucleic acid sequences can be a plurality of genomic sequences of a subject A that are not found in a subject B. These target nucleic acid sequences can be utilized to identify the presence of subject A in a complex sample comprising subject A and subject B. Likewise, the target nucleic acid sequences can be a plurality of genomic sequences of subject B that are not found in subject A. These target nucleic acid sequences can be utilized to identify the presence of subject B in a complex sample comprising subject A and subject B. In some cases, the detection device can be capable of identifying subject A from subject B (i.e., having probes that recognize only subject A), capable of identifying subject B from subject A (i.e., having probes that recognize only subject B), or identifying both subject A and subject B (i.e., having probes that recognize subject A and probes that recognize subject B).

In some cases, the methods and systems herein are capable of distinguishing between 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10000 or more than 10000 subjects. In some cases, the detection device comprises 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10000 or more than 10000 subject-specific features. In some cases, the methods and systems herein are capable of distinguishing between at least 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10000 or more than 10000 subjects. In some cases, the detection device comprises at least 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10000 or more than 10000 subject-specific features.

The target nucleic acid sequences can be one or more nucleic acid sequences present on the nucleic acids contained within the complex sample. The target sequences can be designed to bind (e.g., chemically bind) to their genetic complements within the sample. The one or more nucleic acid sequences can be distinguishable from one other, thereby providing the ability to resolve the origin of the nucleic acid within the sample. For example, a complex sample can include two or more subjects. Each individual subject can contain nucleic acids, therefore, the complex sample can include nucleic acids from each individual subject. In some cases, the methods and systems herein are used to identify the individual subjects present in the sample. Take, for example, a sample comprising Subject A and Subject B. The sample can include nucleic acids that originate from both Subject A and Subject B. The nucleic acids can include at least one target nucleic acid sequence that distinguishes Subject A from Subject B and vice versa. The methods and systems herein can be used to identify the at least one target nucleic acid sequence. This information can then be used to determine that the complex sample included both Subject A and Subject B.

Target Nucleic Acids

A target nucleic acid sequence can be any nucleic acid sequence that identifies one subject from another, or that differentiates attributes of targets, such as antibiotic resistance or pathogenicity. In some cases, the one or more subjects present in the complex sample have genomes that are substantially identical and can be difficult to resolve using standard microarray technologies. In some cases, the one or more subjects have genomes that are 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999% identical. In some cases, the one or more subjects are one or more different strains of microorganisms, for example, one or more strains of bacteria, virus, fungus and the like.

Target nucleic acid sequences can comprise one or more genetic features. The one or more genetic features can distinguish one subject from another. A genetic feature can comprise a genome, a genotype, a haplotype, chromatin, a chromosome, a chromosome locus, chromosomal material, an allele, a gene, a gene cluster, a gene locus, a genetic polymorphism, a genetic mutation, a single nucleotide polymorphism (SNP), a restriction fragment length polymorphism (RFLP), a variable tandem repeat (VTR), a copy number variant (CNV), a microsatellite sequence, a genetic marker, a sequence marker, a sequence tagged site (STS), a plasmid, a transcription unit, a transcription product, a gene expression level, a genetic expression state. A target nucleic acid sequence can comprise essentially any known genetic feature.

Target nucleic acids can comprise deoxyribonucleic acid (DNA) or ribonucleic acid (RNA). DNA can be genomic DNA or cDNA. cDNA can be produced by reverse transcription of RNA as known to one of skill in the art. Target nucleic acids can be single-stranded or double-stranded. In some cases, target nucleic acids can be modified. Nucleic acid modifications can include those that are known in the art and target nucleic acids can comprise essentially any modification. Useful modifications include, without limitation, radioactive and fluorescent labels as well as anchor ligands such as biotin or digoxigenin. The modification(s) can be placed internally or at either the 5' or 3' end of the targets. Target modification can be carried out post-synthetically, either by chemical or enzymatic reaction such as ligation or polymerase-assisted extension.

The length of a target nucleic acid can vary. The target nucleic acids can vary in size from tens to hundreds, or thousands of base pairs, or even tens or hundreds of thousands of base pairs. In some examples, the target nucleic acids are about 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000 or more base pairs in length. In some examples, the target nucleic acids are at least about 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000 or more base pairs in length. In some examples, the target nucleic acids are at most about 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, or 10000 base pairs in length.

Prior to application to the detection device, target nucleic acids can undergo any number of sample preparation steps. These steps can include any number of fragmentation, amplification, modification or purification steps known to those of skill in the art.

Target nucleic acids can be released from a biological sample by any technique, including chemical lysis, sonication, homogenization and the like. Target nucleic acids can undergo any number of purification steps known in the art (e.g., to remove cellular debris, contaminants, or other material) prior to any further processing steps.

In some cases, target nucleic acids can be labeled prior to application to a detection device. In some cases, target nucleic acids can be labeled subsequent to application to a detection device. Target nucleic acids can be labeled with multiple labels. A nucleic acid label can be any tag that enables detection of the nucleic acid. Any number of labels can be used including radiolabels, fluorophores, dyes, biotin, enzymes (e.g., horseradish peroxidase (HRP), alkaline phosphatase (AP)), and the like. Target nucleic acids can be labeled at the 5' end, the 3' end, or both. In some cases, the target nucleic acids are body-labeled. Any method of labeling nucleic acids can be used including enzymatic techniques such as terminal deoxynucleotidyl transferase (TdT), T4 RNA ligase, T4 polynucleotide kinase (PNK), DNA polymerase, RNA polymerase; or chemical techniques such as periodate oxidation, 1-Ethyl-3-[3-dimethylaminopropyl] carbodiimide hydrochloride (EDC) activation of 5' phosphates, or chemical random-labeling (e.g., photoreactive labeling systems, Universal Linkage System available commercially from Kreatech Diagnostics). In some cases, no label is required and binding of target can be detected through release of protons, change in chemical composition on a surface, change of index of refraction in an optical path, or direct electrical detection of a hybridization event.

Target nucleic acids can be labeled with a dye or a stain. Dyes suitable for labeling nucleic acids can include those that are known in the art. The dye can be a fluorescent dye. In some cases, the dye is Cy3. In some cases, the dye is Cy5.

Target nucleic acids can be labeled at the 5' end, the 3'end, or body-labeled. The decision as to which method to use can partly depend on the degree of labeling needed and whether the label can cause steric hindrance and prevent interaction with the probes.

In some cases, the nucleic acid label is randomly incorporated throughout the nucleic acid molecule (i.e., body-labeled). A variety of methods can be used to body-label a target nucleic acid. Body-labeling protocols can involve the use of an enzyme to incorporate a labeled nucleotide into a target nucleic acid. In some cases, the body-labeled nucleic acid is generated with standard polymerase chain reaction (PCR) methods. This method can serve two purposes: 1) the random incorporation of labeled nucleotides into the growing nucleic acid strand; and 2) amplification of the template nucleic acids. This method can involve the use of target-specific primers or random primers. In some cases, the target nucleic acids are amplified by PCR prior to application to the detection device.

In some cases, the labeled nucleotides are randomly incorporated by random primer extension. In this example, a plurality of random primers (e.g., hexanucleotides) are used to prime DNA synthesis randomly on a single-stranded DNA template. DNA synthesis and random incorporation of labeled nucleotides can involve the use of DNA polymerase I or the Klenow fragment of DNA polymerase I. In some cases, the labeling can occur after hybridization of the target nucleic acid to a probe, for example, by using a double-stranded DNA labeling protocol.

In other cases, the labeled nucleotides are randomly incorporated by rolling circle amplification. This method can be particularly well suited when the target nucleic acid molecules are circular (e.g., plasmids, circular genomes of bacteriophages, circular RNA genomes of viroids, and the like). In rolling circle amplification, a nick is generated in one strand of the circular nucleic acid molecule creating a discontinuous and a continuous strand. The continuous strand of the circular vector is amplified using an isothermal amplification reaction. In some cases, rolling circle amplification uses 429 DNA polymerase which exhibits high strand displacement activity.

In some cases, target nucleic acids are not amplified prior to hybridization to the probes of the detection device.

In some cases, target nucleic acids are sheared or fragmented prior to application to the detection system. Methods of shearing can include those that are known in the art and can include sonication, needle shearing, passage through a French pressure cell, point-sink shearing, acoustic shearing, restriction digestion, fragmentase, or transposome-mediated fragmentation. In some cases, target nucleic acids are labeled prior to shearing or fragmenting. This method can be suitable if the labeling method involves, e.g., rolling circle amplification. In other cases, shearing of the target nucleic acids occurs prior to labeling.

Figure 6:
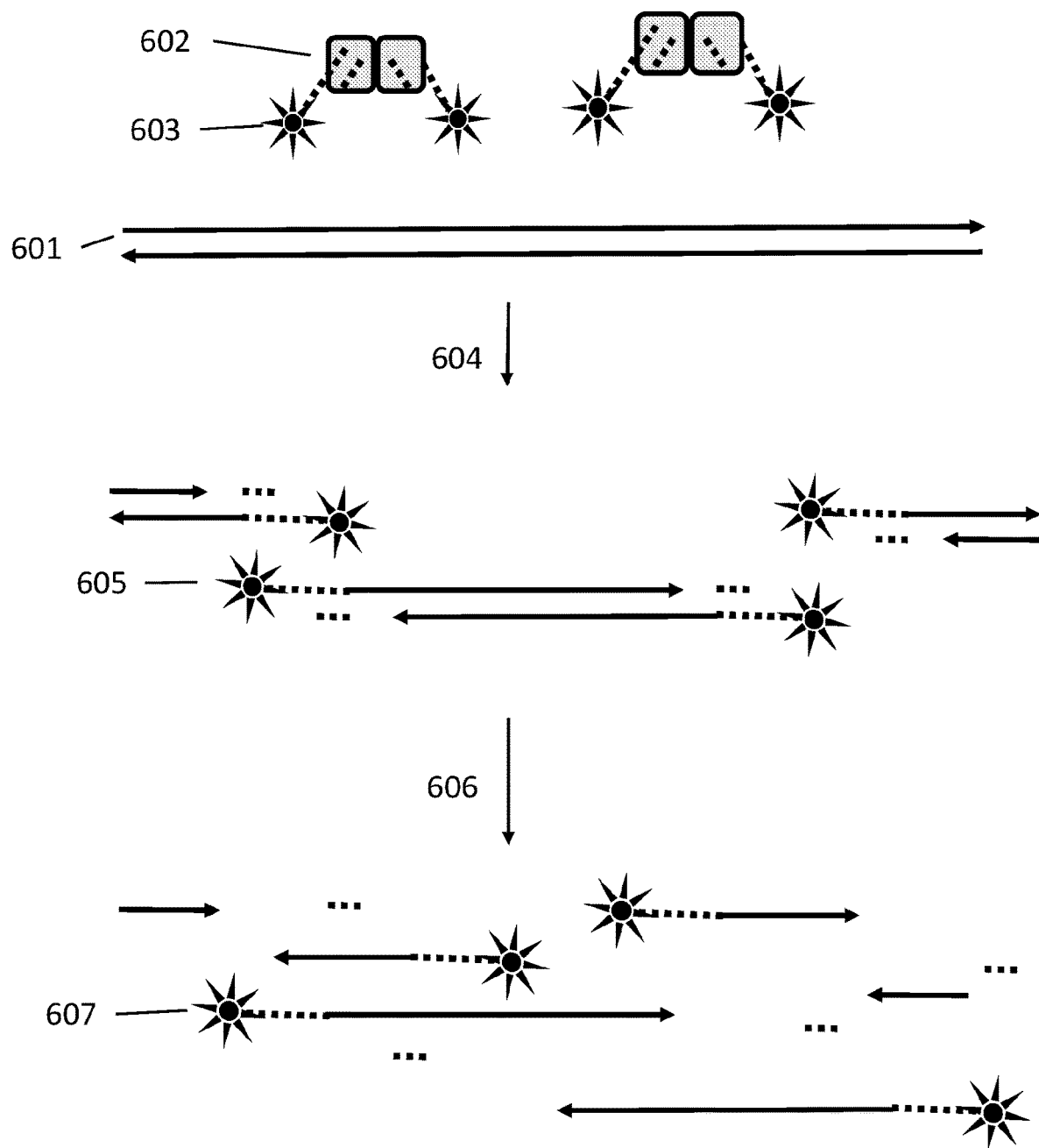
FIG. 6 depicts an exemplary schematic of one-step fragmentation and labeling of double-stranded DNA using transposome complexes.

Transposome mediated fragmentation can be used to simultaneously generate fragments and label those fragments for detection. Transposases (such as Tn5) can cleave and covalently attach synthetic DNA sequences into the 5' end of other DNA molecules. By attaching, for example, 5' labeled fluorophore to the synthetic DNA, it is possible to simultaneously fragment and label DNA. This fragmented and labeled (e.g., fluorescently labeled) DNA after denaturation can be ready for hybridization to the array. For example, FIG. 6 shows an exemplary schematic of double-stranded DNA (dsDNA) 601 interacting with transposome complexes 602 containing oligonucleotides with labels 603 (e.g., fluorescent labels). After incubation 604, fragmented dsDNA with labels 605 is produced by the transposome complexes. Denaturing 606 can then be used to produce labeled single-stranded DNA (ssDNA) 607 for hybridization. Transposome mediated fragmentation can be used to produce fragmented DNA, either double stranded or single stranded (e.g., after denaturing), that also contains labels and pieces of synthetic DNA from the transposome. Such techniques can increase yield and efficiency compared to a two-step process of fragmentation and labeling.

Figure 8:
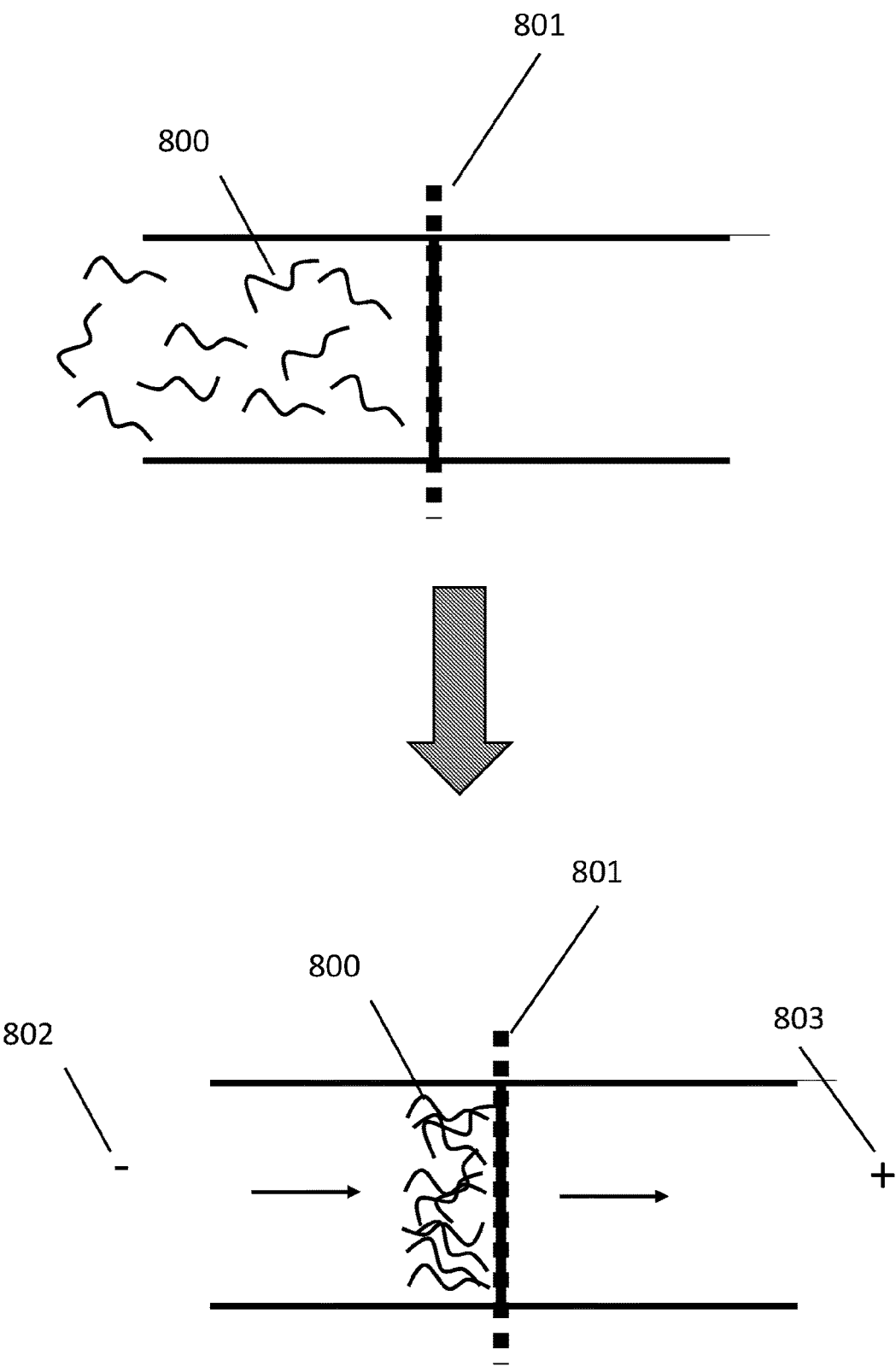
FIG. 8 depicts an exemplary schematic of nucleic acids being concentrated at an oligonucleotide array on a filter substrate.

Sample material, such as nucleic acids, can be concentrated and/or purified. This can aid in the analysis of the sample material. For example, a membrane (e.g., a molecular weight cutoff membrane such as diethylaminoethyl (DEAE) cellulose paper) that does not allow nucleic acid to pass, but does allow ions, proteins, and other cell debris to pass, can be used to concentrate nucleic acids. Spotting and immobilization of the oligonucleotide capture array on this membrane can allow accelerated hybridization to the array by increasing the concentration of the target near the capture probes and bringing the targets to the capture probes. The direction of the electric field or fluid flow can be temporarily reversed or pulsed to foster flow in a plane parallel to the surface to further improve on hybridization rates and shorten hybridization time. For example, FIG. 8 shows an example of sample DNA 800 being brought near an oligonucleotide array on a filter substrate 801; when an electric field is applied (negative 802, positive 803), the sample DNA undergoes electrophoresis and is concentrated at the array. Alternatively, if the electrical current is briefly reversed (using, for example a simple molecular weight cutoff filter membrane), the nucleic acids can be moved off the membrane and into solution, and used, for example, to hybridize to an array immobilized onto a silica, plastic, glass, or another substrate. Concentration can also be conducted by applying fluid flow to move the nucleic acids relative to the membrane, instead of or in addition to electrophoretic motion.

Electrodes (e.g., 802 and 803 in FIG. 8) can be spaced apart from each other such that the concentration of free radicals or other sources of oxidative damage to nucleic acids is reduced. This type of design can reduce the amount of oxidative damage that a nucleic acid experiences during, for example, a concentration step.

Isotachophoresis (ITP), in addition to other forms of electrophoresis, can also be used to concentrate and/or purify analytes, such as nucleic acids, in sample material. The analyte can be a nucleic acid (such as DNA or RNA) a protein, a metabolite, or a combination thereof. This can aid in the analysis of the analyte material. In ITP, a leading electrolyte (with ionic mobility higher than the analyte material) and a trailing electrolyte (with ionic mobility less than the analyte material) can be used to bracket analyte material in an electrophoresis zone. For example, isotachophoresis can be used to concentrate nucleic acids in a sample. Concentrated nucleic acids can then be passed over or otherwise contacted to a detection device such as an oligonucleotide array or other detection devices discussed herein, such as arrays employing pooled probes. This concentration step can improve the performance of the detection (e.g., sensitivity, specificity). Isotachophoresis can also be used in delivering analytes to a detection device; isotachophoresis can cause analytes to migrate to or near to the detection device. In some cases, the leading electrolyte and trailing electrolyte have common counter-ions but different co-ions. Various modes and forms of ITP can be employed, including but not limited to plateau mode, peak mode, and transient ITP (tITP). In plateau mode, the separation can be characterized by a stair-like profile, with each stair step representing an electrolyte or analyte zone with increasing electric fields and decreasing conductivities. In peak mode, analyte amounts can be below that required to reach plateau concentrations, and such analytes can be concentrated into sharp Gaussian-like peak distributions. In peak mode, spacer compounds with intermediate ionic mobilities can be used to segregate adjacent analyte zones. Transient ITP can be used to concentrate analytes, which can subsequently be separated by methods such as zone electrophoresis. Transient ITP can be achieved by mixing the sample with the trailing electrolyte and surrounding the mixture with leading electrolyte zones, or vice versa.

Sample material, including nucleic acids (e.g., DNA, RNA), can be processed at a range of input concentrations, including about 0.0001 nanomolar (nM), 0.0002 nM, 0.0005 nM, 0.001 nM, 0.002 nM, 0.005 nM, 0.01 nM, 0.02 nM, 0.05 nM, 0.1 nM, 0.2 nM, 0.5 nM, 1 nM, 2 nM, 5 nM, 10 nM, 20 nM, 50 nM, 100 nM, 200 nM, 500 nM, 1 micromolar (µM), 2 µM, 5 µM, 10 µM, 20 µM, 50 µM, 100 µM, 200 µM, 500 µM, 1000 µM, or more. In some cases, sample material can be processed at an input concentration of at least about 0.0001 nanomolar (nM), 0.0002 nM, 0.0005 nM, 0.001 nM, 0.002 nM, 0.005 nM, 0.01 nM, 0.02 nM, 0.05 nM, 0.1 nM, 0.2 nM, 0.5 nM, 1 nM, 2 nM, 5 nM, 10 nM, 20 nM, 50 nM, 100 nM, 200 nM, 500 nM, 1 micromolar (µM), 2 µM, 5 µM, 10 µM, 20 µM, 50 µM, 100 µM, 200 µM, 500 µM, 1000 µM, or more. In some cases, sample material can be processed at an input concentration of at most about 0.0001 nanomolar (nM), 0.0002 nM, 0.0005 nM, 0.001 nM, 0.002 nM, 0.005 nM, 0.01 nM, 0.02 nM, 0.05 nM, 0.1 nM, 0.2 nM, 0.5 nM, 1 nM, 2 nM, 5 nM, 10 nM, 20 nM, 50 nM, 100 nM, 200 nM, 500 nM, 1 micromolar (µM), 2 µM, 5 µM, 10 µM, 20 µM, 50 µM, 100 µM, 200 µM, 500 µM, 1000 µM.

Monitoring and Control of ITP Zone Motion

A zone of nucleic acids concentrated and/or controlled by ITP can be visualized or otherwise monitored by a variety of methods. ITP zones can be visually monitored by, for example, labelling nucleic acids with a dye (e.g., fluorescent dye). Dyes can be added to nucleic acids by labeling targets specifically (e.g., by biotin/streptavidin interaction, by fluorescent hybridization probe) or by labelling nucleic acids generally (e.g., with an intercalating dye such as YOYO-1, with other labels that broadly label nucleic acids such as DNA).

Visual signals, such as fluorescent signals, can be detected by a variety of approaches. Some or all of a device can be partially or totally translucent or transparent, allowing observation or imaging of a visual signal. A visual detector, such as a CCD, can also be coupled to the device to allow imaging. One or more individual detectors can be coupled to the device, for example to monitor the position of an ITP zone and/or to detect hybridization on an array as discussed herein. Detectors can be coupled to the device directly or indirectly, such as via one or more wave guides.

ITP zones can also be detected by non-visual means. Electric sensors (e.g., voltage sensors, current sensors) can be used to detect a band of material (e.g., DNA) in an ITP zone. For example, a change in voltage drop as an ITP band passes the sensor can be detected. Other electronic and/or surface detection methods can be used to monitor the position of an ITP band and/or to detect hybridization on an array as discussed herein. For example, surface plasmon resonance (SPR) can be used to detect the hybridization of sample nucleic acids to an array feature.

The position of an ITP zone can also be estimated or assumed based on previous calibrations. For example, the motion of an ITP zone under given conditions can be observed (e.g., visually), and then subsequent motion and control of an ITP zone can be estimated or assumed based on the calibration to the previously observed motion (e.g., in a visually sealed device).

Microfluidic Flow Cells

In addition to concentration of sample material, ITP can be used to bring sample material in contact with probes (e.g., on an array). In some examples, the width of the ITP band is wide enough to contact the entire width of an array as the ITP band progresses along the array length. In other examples, the ITP band is less wide than the array, and the ITP band can be swept across the array in a pattern that brings it in contact with most or all of the array. In some cases, the method can comprise binding an analyte in the sample material to a probe, detecting the analyte, or a combination thereof. When the method comprises binding and detecting said analyte, the method can be conducted in less than about 5 minutes (min), 10 min, 15 min, 20 min, 30 min, 45 min, or 60 min.

A variety of substrates can be used for the analysis and sample handling disclosed herein. Exemplary substrates include but are not limited to glass, silicon, polydimethylsiloxane (PDMS), polymethylmethacrylate (PMMA), and other polymers. Flow cells and other fluidic structures can have dimensions compatible with ITP.

In some cases, channel or flow cell height can be less than or equal to about 100 micrometers (µm), 90 µm, 80 µm, 70 µm, 60 µm, 50 µm, 40 µm, 30 µm, 20 µm, 10 µm, 5 µm, 2 µm, or 1 µm. In some cases, channel height can be selected to reduce diffusion distance from the bulk fluid (e.g., in an ITP band) to the probes (e.g., on an array surface). In other cases, probes and sample can be brought together in an ITP band, and sample bound to probes can subsequently be captured and/or analyzed.

In some cases, channel or flow cell width can be about 1 micrometer (µm), 2 µm, 5 µm, 10 µm, 20 µm, 50 µm, 100 µm, 200 µm, 500 µm, 1 millimeter (mm), 2 mm, 5 mm, 10 mm, 20 mm, 50 mm, 100 mm, 200 mm, 500 mm, 1000 mm, or more. In some cases, channel or flow cell width can be at most about 1 micrometer (µm), 2 µm, 5 µm, 10 µm, 20 µm, 50 µm, 100 µm, 200 µm, 500 µm, 1 millimeter (mm), 2 mm, 5 mm, 10 mm, 20 mm, 50 mm, 100 mm, 200 mm, 500 mm, or 1000 mm. In some cases, channel or flow cell width can be at least about 1 micrometer (µm), 2 µm, 5 µm, 10 µm, 20 µm, 50 µm, 100 µm, 200 µm, 500 µm, 1 millimeter (mm), 2 mm, 5 mm, 10 mm, 20 mm, 50 mm, 100 mm, 200 mm, 500 mm, 1000 mm, or more.

In some cases, channel or flow cell length can be about 1 micrometer (µm), 2 µm, 5 µm, 10 µm, 20 µm, 50 µm, 100 µm, 200 µm, 500 µm, 1 millimeter (mm), 2 mm, 5 mm, 1 centimeter (cm), 2 cm, 5 cm, 10 cm, 20 cm, 50 cm, 100 cm, or more. In some cases, channel or flow cell length can be at most about 1 micrometer (µm), 2 µm, 5 µm, 10 µm, 20 µm, 50 µm, 100 µm, 200 µm, 500 µm, 1 millimeter (mm), 2 mm, 5 mm, 1 centimeter (cm), 2 cm, 5 cm, 10 cm, 20 cm, 50 cm, 100 cm, or more. In some cases, channel or flow cell length can be at least about 1 micrometer (µm), 2 µm, 5 µm, 10 µm, 20 µm, 50 µm, 100 µm, 200 µm, 500 µm, 1 millimeter (mm), 2 mm, 5 mm, 1 centimeter (cm), 2 cm, 5 cm, 10 cm, 20 cm, 50 cm, 100 cm, or more.

Channels and flow cells can have different geometries. For example, channels or flow cells can be straight, can comprise one or more turns or bends, can comprise one or more constrictions or tapers, can comprise one or more expansions or widenings, and can comprise one or more serpentine regions. In some cases, a channel or flow cell comprises no constrictions, tapers, expansions, or widenings (except, optionally, for channel inlet and outlet regions).

ITP Control of Upstream and Downstream Operation

In addition to sample concentration and contacting with probes, ITP can be used for other upstream and/or downstream operations. Exemplary operations include but are not limited to sample collection, cell lysis, purification of sample material (e.g., nucleic acids) from input material (e.g., cell lysate), sample concentration, sample labeling (e.g., fluorescent labeling), contacting sample with probes (e.g., on an array), removal of unbound material from the probes, recovery of sample material from the probes (e.g., from an array), and other analysis and handling of sample material (e.g., additional assays, storage of material).

ITP Operating Parameters

ITP can be conducted at a variety of different operating parameters, including different voltages, field strengths, currents, sample input concentrations, and operation times.

ITP can be conducted at a voltage of about 10 volts (V), 20 V, 30 V, 40 V, 50 V, 60 V, 70 V, 80 V, 90 V, 100 V, 150 V, 200 V, 250 V, 300 V, 350 V, 400 V, 450 V, 500 V, 550 V, 600 V, 650 V, 700 V, 750 V, 800 V, 850 V, 900 V, 950 V, 1000 V, or more. In some cases, ITP can be conducted at a voltage of at most about 10 volts (V), 20 V, 30 V, 40 V, 50 V, 60 V, 70 V, 80 V, 90 V, 100 V, 150 V, 200 V, 250 V, 300 V, 350 V, 400 V, 450 V, 500 V, 550 V, 600 V, 650 V, 700 V, 750 V, 800 V, 850 V, 900 V, 950 V, 1000 V, or more. In some cases, ITP can be conducted at a voltage of at least about 10 volts (V), 20 V, 30 V, 40 V, 50 V, 60 V, 70 V, 80 V, 90 V, 100 V, 150 V, 200 V, 250 V, 300 V, 350 V, 400 V, 450 V, 500 V, 550 V, 600 V, 650 V, 700 V, 750 V, 800 V, 850 V, 900 V, 950 V, 1000 V, or more.

ITP can be conducted at a field strength of about 10 volts per centimeter (V/cm), 20 V/cm, 30 V/cm, 40 V/cm, 50 V/cm, 60 V/cm, 70 V/cm, 80 V/cm, 90 V/cm, 100 V/cm, 200 V/cm, 300 V/cm, 400 V/cm, 500 V/cm, 600 V/cm, 700 V/cm, 800 V/cm, 900 V/cm, 1000 V/cm, or more. In some cases, ITP can be conducted at a field strength of at most about 10 volts per centimeter (V/cm), 20 V/cm, 30 V/cm, 40 V/cm, 50 V/cm, 60 V/cm, 70 V/cm, 80 V/cm, 90 V/cm, 100 V/cm, 200 V/cm, 300 V/cm, 400 V/cm, 500 V/cm, 600 V/cm, 700 V/cm, 800 V/cm, 900 V/cm, 1000 V/cm, or more. ITP can be conducted at a field strength of at least about 10 volts per centimeter (V/cm), 20 V/cm, 30 V/cm, 40 V/cm, 50 V/cm, 60 V/cm, 70 V/cm, 80 V/cm, 90 V/cm, 100 V/cm, 200 V/cm, 300 V/cm, 400 V/cm, 500 V/cm, 600 V/cm, 700 V/cm, 800 V/cm, 900 V/cm, 1000 V/cm, or more.

ITP can be conducted at a current of about 1 micro-amp ($\mu A$), 2 $\mu A$, 3 $\mu A$, 4 $\mu A$, 5 $\mu A$, 6 $\mu A$, 7 $\mu A$, 8 $\mu A$, 9 $\mu A$, 10 $\mu A$, 20 $\mu A$, 30 $\mu A$, 40 $\mu A$, 50 $\mu A$, 60 $\mu A$, 70 $\mu A$, 80 $\mu A$, 90 $\mu A$, 100 $\mu A$, 110 $\mu A$, 120 $\mu A$, 130 $\mu A$, 140 $\mu A$, 150 $\mu A$, 160 $\mu A$, 170 $\mu A$, 180 $\mu A$, 190 $\mu A$, 200 $\mu A$, 250 $\mu A$, 300 $\mu A$, 350 $\mu A$, 400 $\mu A$, 450 $\mu A$, 500 $\mu A$, 550 $\mu A$, 600 $\mu A$, 650 $\mu A$, 700 $\mu A$, 750 $\mu A$, 800 $\mu A$, 850 $\mu A$, 900 $\mu A$, 950 $\mu A$, 1 amp (A), or more. In some cases, ITP can be conducted at a current of at most about 1 micro-amp ($\mu A$), 2 $\mu A$, 3 $\mu A$, 4 $\mu A$, 5 $\mu A$, 6 $\mu A$, 7 $\mu A$, 8 $\mu A$, 9 $\mu A$, 10 $\mu A$, 20 $\mu A$, 30 $\mu A$, 40 $\mu A$, 50 $\mu A$, 60 $\mu A$, 70 $\mu A$, 80 $\mu A$, 90 $\mu A$, 100 $\mu A$, 110 $\mu A$, 120 $\mu A$, 130 $\mu A$, 140 $\mu A$, 150 $\mu A$, 160 $\mu A$, 170 $\mu A$, 180 $\mu A$, 190 $\mu A$, 200 $\mu A$, 250 $\mu A$, 300 $\mu A$, 350 $\mu A$, 400 $\mu A$, 450 $\mu A$, 500 $\mu A$, 550 $\mu A$, 600 $\mu A$, 650 $\mu A$, 700 $\mu A$, 750 $\mu A$, 800 $\mu A$, 850 $\mu A$, 900 $\mu A$, 950 $\mu A$, 1 amp (A), or more. ITP can be conducted at a current of at least about 1 micro-amp ($\mu A$), 2 $\mu A$, 3 $\mu A$, 4 $\mu A$, 5 $\mu A$, 6 $\mu A$, 7 $\mu A$, 8 $\mu A$, 9 $\mu A$, 10 $\mu A$, 20 $\mu A$, 30 $\mu A$, 40 $\mu A$, 50 $\mu A$, 60 $\mu A$, 70 $\mu A$, 80 $\mu A$, 90 $\mu A$, 100 $\mu A$, 110 $\mu A$, 120 $\mu A$, 130 $\mu A$, 140 $\mu A$, 150 $\mu A$, 160 $\mu A$, 170 $\mu A$, 180 $\mu A$, 190 $\mu A$, 200 $\mu A$, 250 $\mu A$, 300 $\mu A$, 350 $\mu A$, 400 $\mu A$, 450 $\mu A$, 500 $\mu A$, 550 $\mu A$, 600 $\mu A$, 650 $\mu A$, 700 $\mu A$, 750 $\mu A$, 800 $\mu A$, 850 $\mu A$, 900 $\mu A$, 950 $\mu A$, 1 amp (A), or more. In some cases, current varies during operation at a constant voltage. In other cases, voltage varies during operation at a constant current.

ITP can be conducted for a time duration of about 1 second (s), 2 s, 5 s, 10 s, 20 s, 30 s, 40 s, 50 s, 1 minute (min), 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 60 min, 70 min, 80 min, 90 min, 100 min, 110 min, 120 min, or longer. In some cases, ITP can be conducted for a time duration of at most about 1 second (s), 2 s, 5 s, 10 s, 20 s, 30 s, 40 s, 50 s, 1 minute (min), 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 60 min, 70 min, 80 min, 90 min, 100 min, 110 min, 120 min, or longer. In some cases, ITP can be conducted for a time duration of at least about 1 second (s), 2 s, 5 s, 10 s, 20 s, 30 s, 40 s, 50 s, 1 minute (min), 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 60 min, 70 min, 80 min, 90 min, 100 min, 110 min, 120 min, or longer.

Substrates and Coatings

A variety of substrates can be used for the analysis and sample handling disclosed herein. Exemplary substrates include but are not limited to glass, silicon, polydimethylsiloxane (PDMS), polymethylmethacrylate (PMMA), and other polymers. Substrates can be modified (e.g., lithographically) to include channels, flow cells, valves, wells, traps, other fluidic structures, waveguides, electric and electronic circuits, metal structures, patterned doping (e.g., semiconductor doping), and other structures.

Substrates can include tethered molecules (e.g., nucleotides), for example in arrays as discussed herein. Molecules can be bound to a substrate directly or indirectly (e.g., by being bound to second substrate which is then deposited on or associated with the first substrate, such as by beads deposited into an array of wells).

Such substrates can be compatible with processes like ITP. In some cases, substrates are innately conducive to conducting processes such as ITP. In other cases, coatings or other treatments can be provided to enable or improve the process. For example, coatings can be deposited on substrates to reduce electrical breakdown and/or improve ITP. Insulators can be used to insulate substrates (e.g., conductive or semi-conductive substrates) from an electric field, enabling or improving ITP on those substrates. Insulators include but are not limited to silicon dioxide, sapphire, indium tin oxide (ITO), other oxides, polymers, plastics, ceramics, cellulose, paper, and Teflon. In an example, an insulator layer can be deposited over the wells of a bead array prior to loading beads, thereby preventing or reducing dielectric breakdown or electrical short-circuiting. Coatings (e.g., insulators) can be deposited on substrates to a variety of thicknesses, such as about 1 nanometer (nm), 2 nm, 5 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 micrometer ($\mu m$), 2 $\mu m$, 5 $\mu m$, 10 $\mu m$, 20 $\mu m$, 50 $\mu m$, 100 $\mu m$, or more. Coating (e.g., insulator) thickness can be less than about 1 nanometer (nm), 2 nm, 5 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 micrometer (µm), 2 µm, 5 µm, 10 µm, 20 µm, 50 µm, or 100 µm. Coating (e.g., insulator) thickness can be more than about 1 nanometer (nm), 2 nm, 5 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 micrometer (µm), 2 µm, 5 µm, 10 µm, 20 µm, 50 µm, 100 µm, or more.

In an example, ITP is conducted on a bead microwell array (e.g., Illumina BeadArray). Chemical vapor deposition is used to create a silicon oxide layer on the bead array surface, with a thickness of about 500 nanometers (nm). A flow cell is fabricated in PDMS with dimensions of about 4 cm in length, 800 µm in width, and 75 µm in height, with a tapered section in the middle of the flow cell length narrowing to about 200 µm width before expanding again. The lower surface of the PDMS flow cell is activated using an electric discharge wand, to enable bonding of the PDMS to the silicon oxide surface. Platinum wires at two ports at the inlet and outlet ends of the flow cell are set to a voltage of 200 V. Total time for loading, concentration, hybridization, and detection of DNA is about 25 minutes. In other examples, flow cell dimensions can range from about 0.5 to 8 cm in length, from about 200 to 2000 µm in width, silicon oxide thickness can be >250 nm, operating voltage can be from about 50 to 400 volts, and turn-around time (TAT) is from about 5 to 45 minutes. Current can vary, for example in the range of 10-200 µA. Length of nucleic acid sample (e.g., genomic DNA) from sample prep can be in the range of about 10 bases to 10 kb at an input concentration of from about 0.0001 nM to about 100 µM. In other cases, nucleic acid length is about 100 bp to 500 bp (e.g., average of 300 bp +/−200 bp).

ITP can be employed on a variety of substrates that comprise probes, such as microarrays with DNA oligonucleotides printed or otherwise bound on the surface (e.g., Affymetrix, Agilent) or attached to beads (e.g., Illumina), as discussed herein. Many commercially available microarrays are designed for applications with very high throughput; accordingly, these arrays can comprise many distinct features (e.g., probe spots, beads) and can be fairly large in area, such as at least a few millimeters by a few millimeters, often with multiple such arrays on a given microarray chip. Flow cells traditionally employed with for such arrays commonly have large volumes of the order of 10 microliters and large surface areas. Conducting ITP in such of flow cells can require voltages of 1 kV or higher. Operation at such voltages may give rise issues such as dielectric breakdown, even with very thick insulation (e.g., $SiO_2$) on silicon wafers. Furthermore, for large flow cells, a larger genomic DNA sample can be required as input, such as a few micrograms. Accordingly, ITP is generally not employed with such silicon-based arrays, or their applications with respect to input amount of DNA. On the other hand, devices employing pooled probe approaches described herein can be well-adapted to use with ITP. Techniques enabling identifying a small amount of sample, such as pooled probe approaches described herein, can benefit from concentration by some process over the surface of the array. Furthermore, such approaches can employ smaller numbers of probes (e.g., ~1000 different probes for ~100 targets) compared to >100,000 probes for commercially available microarrays described above. This smaller number of probes can adequately fit in a smaller flow cell (e.g., <1 mm wide and 1 mm long, height <75 µm). These design parameters can enable use of ITP without encountering problems such as dielectric breakdown (e.g., through an insulator over a silicon surface), since the operating voltage can be lower (e.g., 200 V).

In a specific example, ITP was performed on a commercially available array (Illumina, 24-sample BeadArray chip) with a new flow cell design substituted for the existing Illumina flow cell. The new flow cell design served to reduce the volume of the flow cell, and specifically to reduce the width and height of the flow cell, enabling ITP conditions at lower voltage. Restricting the area of the flow cell reduces the number of beads accessible and so reduces the number of probes/detectors that can be accessed on the array surface. Nevertheless, sufficient probes remained accessible for the probe sets described herein (e.g., <1,000 targets and <100,000 total beads), providing adequate information to interrogate the sample.

Nucleic acids can be brought into proximity with a detection device by a variety of means in addition to diffusion. As discussed above, electrophoresis and/or fluid flow can be used to concentrate nucleic acids at or near a detection device surface. Other techniques can also be employed. For example, a detection device surface can have hydrophobic surface chemistry over all or some of its surface (e.g., at probe features), and target nucleic acids can be tagged with a hydrophobic moiety, leading the nucleic acids to have an energetic preference for the hydrophobic regions of the surface. In another example, target nucleic acids can be tagged with a magnetic particle, and magnetic fields can be used to bring the target nucleic acids toward an array surface.

Volume-excluding compounds can also be used to effectively concentrate sample material, such as sample DNA. A volume excluder can be used to exclude sample material from the liquid volume occupied by the volume excluder, thereby concentrating the sample material in the remaining liquid volume. This mechanism can help accelerate capture or binding of sample material, such as hybridization of sample nucleic acids to a substrate. For example, volume excluders can be included in a hybridization buffer to improve hybridization kinetics. Volume excluders can be, for example, beads or polymers, including but not limited to dextran sulfate, ficoll, and polyethylene glycol. Volume excluders can be high molecular weight polymers. Volume excluders can be negatively charged, for example to reduce binding of nucleic acids to the volume excluders.

Probes

The detection devices disclosed herein can comprise a plurality of pooled probes. In some cases, the detection device comprises a reaction chamber. In some cases, the plurality of probes are pooled in the reaction chamber. In some cases, the reaction chamber is a PCR well, an array spot, a droplet, an electrode, or a microfluidic channel. In some cases, the electrode comprises gold, iridium, platinum, copper, or a combination thereof. In some cases, the reaction chamber comprises at least one pore. In other cases, the detection devices disclosed herein comprise a plurality of reaction chambers. In some cases, the plurality of reaction chambers are a plurality of PCR wells, a plurality of array spots, a plurality of droplets, a plurality of electrodes, or a plurality of microfluidic channels. In some cases, the detection device is a single-use device.

In some instances, each of the plurality of reaction chambers comprises one of the one or more sets of probes. In some cases each set of the one or more sets of probes comprises a plurality of probes. In some instances, each of said plurality of probes within a set of probes are identical. In some instances, at least two of said plurality of probes within a set of probes are identical. In some instances, at least two of said plurality of probes within a set of probes are different. In some instances, each of said plurality of probes within a set of probes are different.

In some cases, at least one set of the said one or more sets of probes is immobilized on the surface of the detection device. In some cases, at least one set of the said one or more sets of probes is not immobilized on a surface of the detection device. In some cases, the at least one set of probes not immobilized to the surface is in a solution. For example, the solution can be a PCR solution. In some cases, the PCR solution is in the form of a plurality of droplets. In some cases, the surface is a solid. In other cases, the surface is a semisolid. In some cases, the surface is glass or silicon. The plurality of probes can be immobilized to the surface using surface chemistry.

In one non-limiting example, the plurality of probes is immobilized to the surface of the detection device using 1-Ethyl-3-[3-dimethylaminopropyl]carbodiimide hydrochloride (EDC) chemistry. In this method, carboxyl groups on the detection device are activated with EDC. The activated carboxyl groups can react with a primary amine group to form a stable amide bond. In this example, the surface of the detection device can be a bead, in some cases, a silica or glass bead. The plurality of probes is amino-modified at the 5' or the 3' ends. Non-limiting examples of amino modifications include one or more amino-modified nucleotides including 5'-Aminoallyl-dUTP, 5-Propargylamino-dCTP, $N^6$-6-Aminohexyl-dATP, and 7-Deaza-7-Propargylamino-dATP. Probes can be immobilized to the detection device at either the 5' or the 3' ends using this method. In some cases, a two-step method is utilized: 1) activation with EDC followed by 2) treatment with N-Hydroxysuccimide (NHS) to improve efficiency or to create dry-stable (amine-reactive) intermediates. In some instances, a two-step EDC treatment is employed to improve the immobilization efficiency. In this example, a first concentration of EDC can be applied to the detection device followed by a subsequent second concentration of EDC. In some cases, the first concentration of EDC is lower than the second concentration of EDC. In some cases, this two-step EDC treatment improves the efficiency of probe immobilization.

The detection device can comprise a plurality of probes. The plurality of probes can be distributed on a surface of the detection device. The detection device can comprise a plurality of surfaces which need not be physically connected as a single solid. The surface comprising probes can be, for example, a bead or a series of beads. The beads can be identical. The beads can be microbeads. The beads can be individually resolvable. A bead can comprise a bead specific bar code. A bead can comprise a bead specific label. A bead can comprise a bead specific binding site.

The economics of a microarray, and the hybridization time required, can be improved by reducing the active or hybridization area of the microarray. In this case, the fabrication of a small microarray would save costs and the smaller active area would allow more concentrated sample to be used accelerating hybridization activity.

A probe can be an oligonucleotide that is capable of Watson-Crick base pairing with a target sequence present in a nucleic acid sample. The length of a probe can vary. In some instances, the probes within a genetic feature vary in length by less than 20%, 10%, 5%, or 1%. In some instances, the probes are the same length. The probes can vary in size from tens to hundreds, or thousands of base pairs, or even tens or hundreds of thousands of base pairs. In some cases, probes are about 20 bases long, about 25 bases long, about 30 bases long, about 35 bases long, about 40 bases long, about 45 bases long, about 50 bases long, about 55 bases long, about 60 bases long, about 65 bases long, about 70 bases long, about 75 bases long, about 80 bases long, about 85 bases long, about 90 bases long, about 95 bases long, about 100 bases long, about 110 bases long, about 120 bases long, about 130 long, about 140 bases long, about 150 bases long, about 200 bases long, about 250 bases long, about 300 bases long, about 350 bases long, about 400 bases long, about 450 bases long, about 500 bases long, about 600 bases long, about 700 bases long, about 800 bases long, about 900 bases long, about 1000 bases long, or more than 1000 bases long.

The probes can be distributed onto or into a plurality of reaction chambers into subject-specific features. A subject-specific feature can comprise a plurality of probes. In some instances, a subject-specific feature comprises 10, 100, 1000, 10,000, or over 100,000 individual probes. A subject-specific feature can comprise a plurality of identical probes. In other instances, a subject-specific feature can comprise a plurality of pooled non-identical probes. Non-identical probes can bind to target nucleic acids at different regions. Probes can bind to targets at non-overlapping regions. In some cases, non-identical probes have overlapping sequences. A subject-specific feature can comprise at least 10, 100, 1000, 10,000, 100,000 or more non-identical probes. In some instances, the detection device comprises more than 10, 100, 1000, 10,000, 100,000, 1,000,000, 10,000,000, 100,000,000, or 1,000,000,000 individual subject-specific features.

Subject-specific features can be distributed in a detection device in such a way as to be individually addressable (e.g., individually addressable for detection), such as in discrete reaction chambers. The plurality of probes corresponding to a subject-specific feature can be arranged into one or more sets of probes. Within each set of probes, the plurality of probes can be identical or they can be different from one another. Within each set, the plurality of probes can each comprise a subject-specific feature. The plurality of probes within each set can comprise one or more subject-specific features that distinguish one subject from another. In some cases, a subject-specific feature can be a spot or an area on an array, such as a circular, square, or rectangular area. In some cases, a subject-specific feature can be a bead. In other cases, a subject-specific feature can be a well in a micro-well plate. In other cases, a subject-specific feature can be an electrode. In some cases, a subject-specific feature can be a series of probes labeled with a feature specific tag. The feature specific tag can be, for example, a feature specific barcode or a binding site for a feature specific label. In some instances, features have replicate features. In some instances, the replicate features are identical. In some instances, the replicate features are designed to identify the same target polynucleotides. In some instances, the replicate features are designed to identify the same genome. In some instances, the replicate features are designed to identify any strain within a species. In some cases, the replicate features are designed to identify an individual.

In some instances, at least one of the plurality of probes comprises a guide nucleic acid (gNA), a nucleic acid-guided nuclease system protein, or a complex thereof. In some cases, the gNA binds to the target nucleic acid. In some cases, the guide nucleic acid (gNA): nucleic acid-guided nuclease system protein complex binds to the target nucleic acid. In some embodiments, the nucleic acid-guided nuclease system protein is a CRISPR/Cas system protein. In some embodiments, the CRISPR/Cas system protein is selected from the group consisting of Cas9, CasX, CasY, Cpf1, Cas3, Cas8a-c, Cas10, Cse1, Csy1, Csn2, Cas4, Csm2, and Cm5. In some embodiments, the nucleic acid-guided nuclease system protein is a dead nucleic acid-guided nuclease system protein. In some embodiments, the CRISPR/Cas system protein is a dead CRISPR/Cas system protein. In some embodiments, the CRISPR/Cas system protein is dCas9. In some embodiments, the nucleic acid-guided nuclease system protein is a nucleic acid-guided nuclease system nickase protein. In some embodiments, the CRISPR/Cas system protein is a CRISPR/Cas system nickase protein. In some embodiments, the nucleic acid-guided nuclease system protein exhibits reduced off-target binding. In some cases, the CRISPR/Cas system protein opens a double stranded DNA (dsDNA), allowing binding of the DNA comprising the target nucleic acid to gNA. In some embodiments, the CRISPR/Cas system protein opens the dsRNA at room temperature.

In some embodiments, the gNA comprises a label. In some embodiments, the nucleic-guided nuclease system protein comprises a label. In some embodiments, the gNA and the nucleic-guided nuclease system protein comprises the same label. In some embodiments, the gNA and the nucleic-guided nuclease system protein comprise different labels.

In some cases, at least one of the plurality of probes is labeled with a detectable label. In some cases, the label is selected from the group consisting of an enzyme, an enzyme substrate, an antibody, an antigen binding fragment, a peptide, a chromophore, a lumiphore, a fluorophore, a chromogen, a hapten, an antigen, a radioactive isotope, a magnetic particle, a nanoparticle (e.g., gold nanoparticles), a quantum dot, a barcode (e.g., nucleic acid barcode), an active site, a binding site, a redox active marker group, an aptamer, hydrophobic species, hydrophilic species, one member of a binding pair, a donor dye (reporter), an acceptor dye (quencher), an organometallic compound, and combinations thereof.

In some cases, the detectable label is a reporter, a quencher, or a combination thereof. Examples of reporters include, but are not limited to, the reporters shown in Table 1. In some embodiments, any suitable reporter is used. In some instances, the reporter is a xanthene, cyanine, squaraine, naphthalene, coumarin, oxadiazole, anthracene, pyrene, oxazine, acridine, acrylmethine, tetrapyrrole, or a derivative thereof. In some instances, the xanthene is a rhodamine, a fluorescein, or a derivative thereof In some instances, a plurality of reporters are used. In some instances, when a plurality of reporters are used, the emission maxima of each of the plurality of reporters are separated by at least 15 nm.

Examples of quenchers include, but are not limited to, the quenchers in Table 2. In some embodiments, any suitable quencher is used.

In some instances, the absorption spectrum of the quencher overlaps with the fluorescence spectrum of the reporter.

TABLE 1

Common reporters.

| Dye Name | | | |
| --- | --- | --- | --- |
| BODIPY FL | TAMRA | Pacific Blue | HEX |
| FAM | Rhodamine Red-X | Marina Blue | R6G |
| Oregon Green 488 | Redmond Red | Acridine | Alexa 555 |
| Rhodamine Green | BODIPY 581/591 | Edans | Alexa 568 |
| Oregon Green 514 | Cy3.5 | Coumarin | Alexa 594 |
| TET | ROX | BODIPY 493/503 | LC Red 640 |
| Cal Gold | Cal Red | Cy2 | Alexa 633 |
| BODIPY R6G | Texas Red | BODIPY FL-X | BODIPY 650/665-X |
| Yakima Yellow | BODIPY TR-X | DANSYL | |
| JOE | BODIPY 630/665-X | Alex 488 | Alexa 647 |
| HEX | Pulsar-650 | NBD-X | Cy5 |
| Cal Orange | Qusar-670/Cy5 | Alexa 430 | Alexa 680 |
| BODIPY TMR-X | Cy5.5 | Alexa 532 | Alexa 700 |
| Quasar-570/Cy3 | Alexa 350 | VIC | Alexa 750 |

TABLE 2

Common quenchers.

| Dye name | |
| --- | --- |
| Dabcyl | BHQ-2 |
| QSY 35 | ElleQuencher |
| BHQ-0 | Iowa Black |
| Eclipse | QSY 21 |
| BHQ-1 | BHQ-3 |
| QSY 7 | BHQ-10 |
| QSY 9 | |

In some cases, the detectable label is an organometallic compound. In some cases, the organometallic compound is a ferrocene or an analogue thereof.

Labels can be detectable themselves, or can allow binding of another detectable species. Labels that are not detectable by themselves can be subsequently contacted with a detectable species. For example, target nucleic acids can be labeled with biotin, and subsequently bound to a streptavidin-conjugated fluorophore for detection. In another example, target nucleic acids can be labeled with nucleic acid barcodes; subsequently, the nucleic acid barcode sequences can be amplified and detected. Detection modalities can include, but are not limited to, optical detection (including FRET, fluorescence lifetime, and other optical properties), electrical detection, magnetic detection, radiolabel detection, sequencing, size detection (e.g., via electrophoretic separation), surface plasmon resonance (SPR), Raman spectroscopy, and mass spectrometry.

Relative signal between features can be determined by the number of labels that bind per feature. For example, as shown in FIG. 2, different numbers of fluorophores can bind per feature, resulting in different relative brightness. FIG. 2 shows the relative brightness of 1 fluorophore per feature (top), 10 fluorophores per feature (middle), and 50 fluorophores per feature (bottom).

Figure 1B:
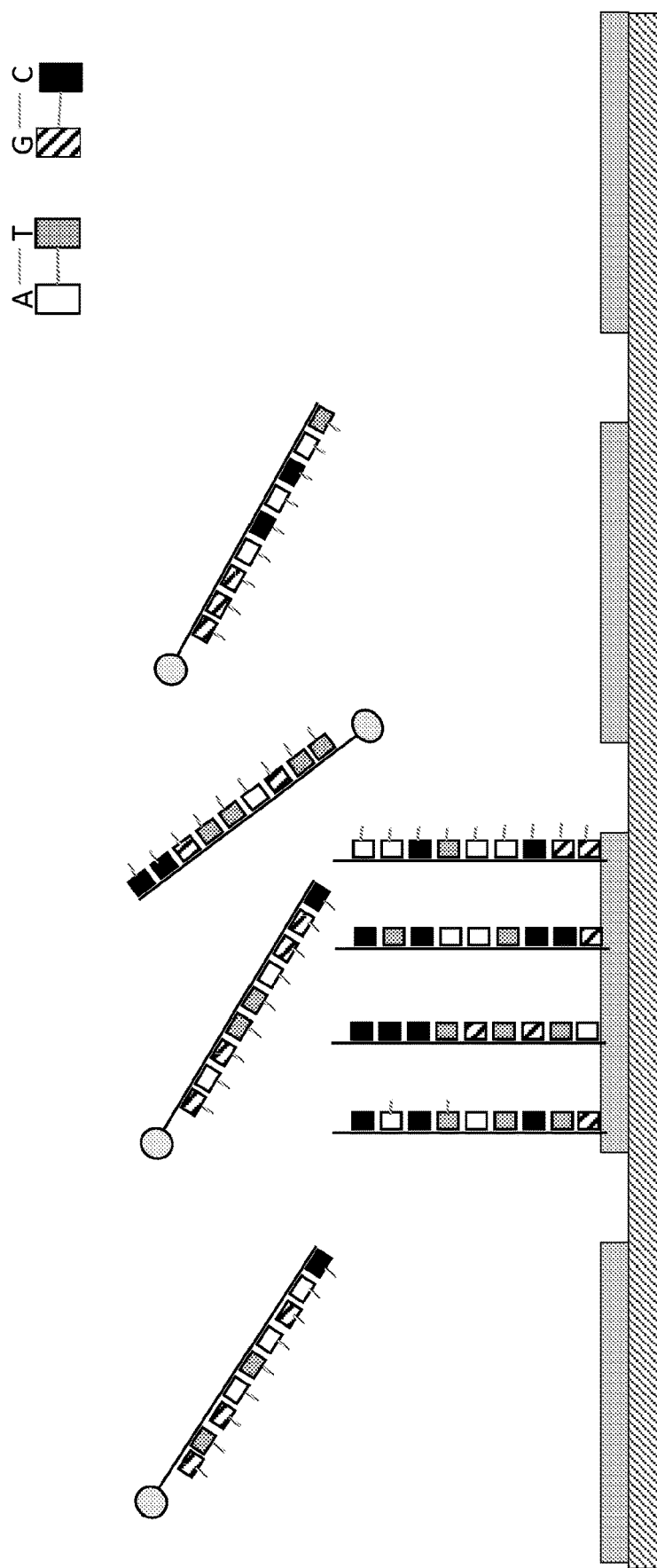
Figure 1C:
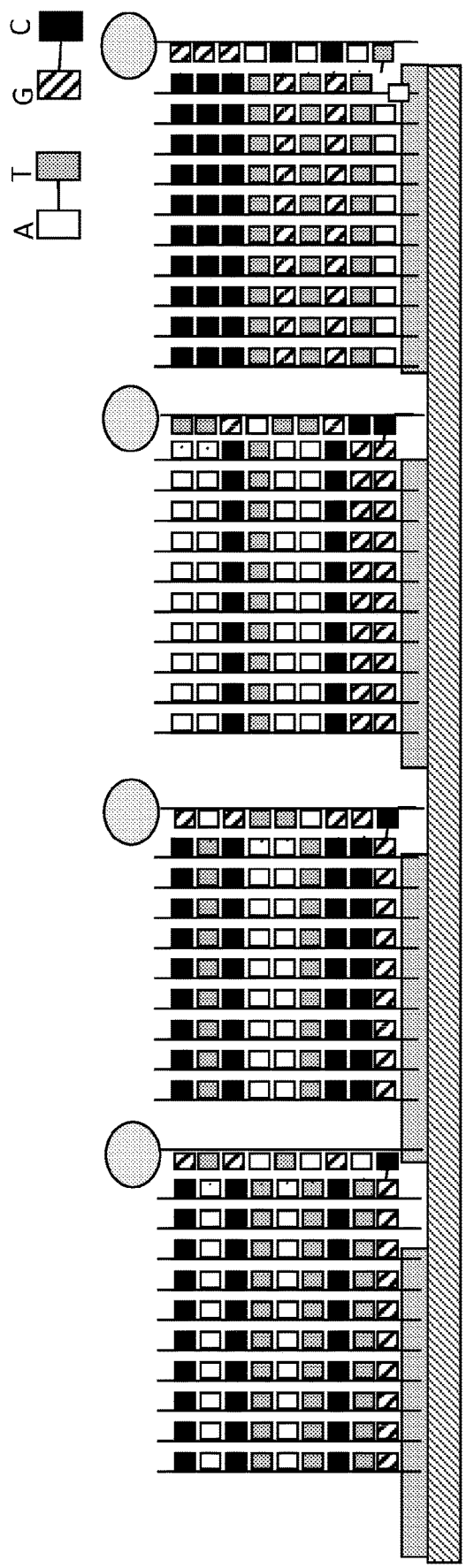

FIG. 1A-FIG. 1F illustrate exemplary biochip systems. FIG. 1A depicts four exemplary features, with each feature comprising identical probes, and four unbound labeled targets from a single subject in a sample. Binding of the targets to the probes would thus result in one unit of signal from each feature. FIG. 1B depicts a subject specific feature with four probes and four unbound labeled targets from a single subject in a sample. Binding of the targets to the probes would thus result in four units of signal from the one feature. FIG. 1C depicts the four targets bound to four different features, resulting in one unit of signal from each feature.

Figure 1D:
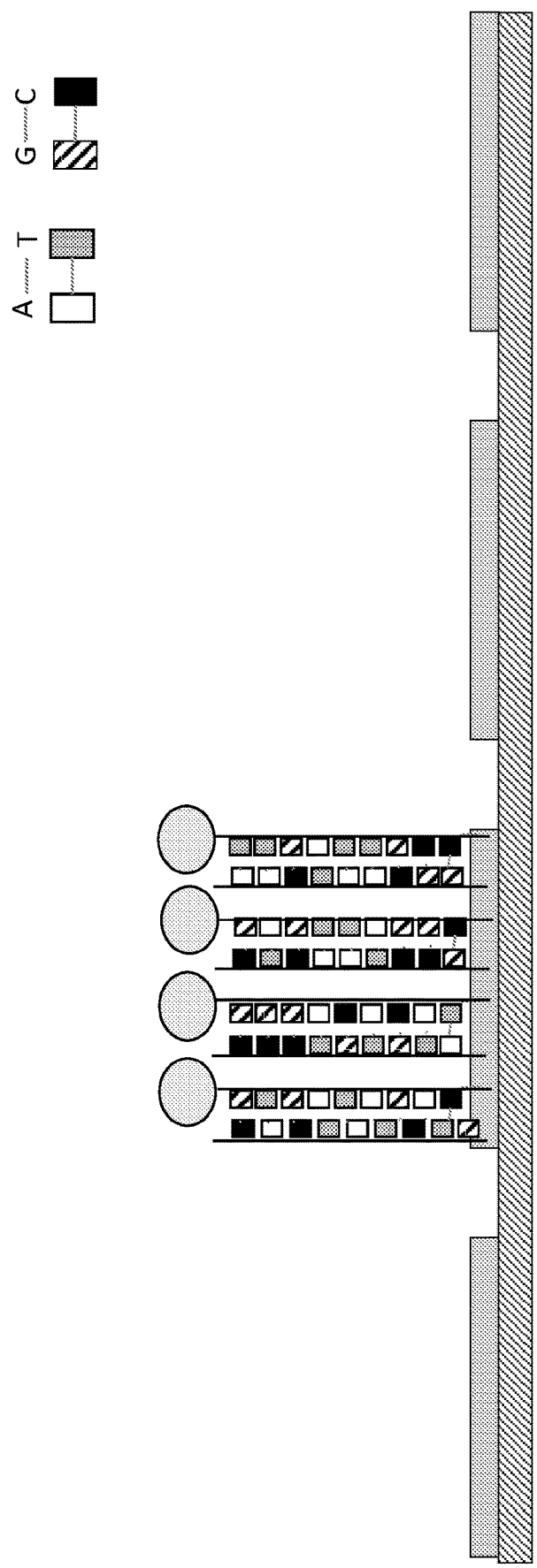
Figure 1E:
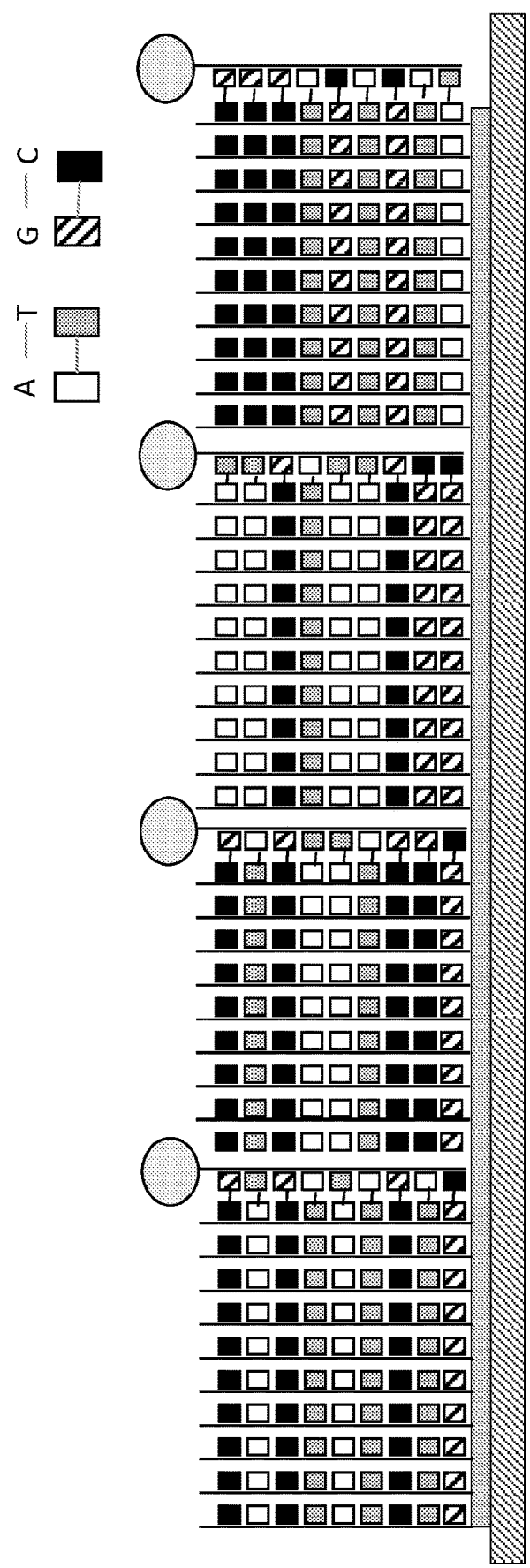
Figure 1F:
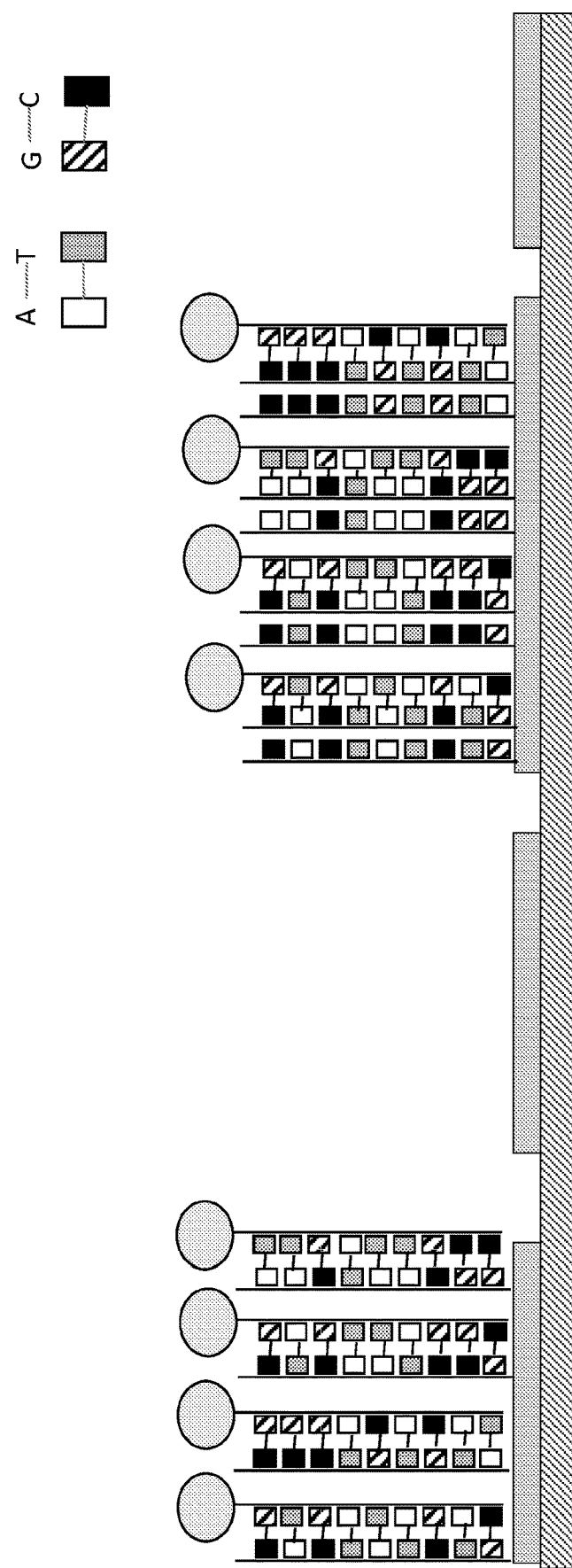

FIG. 1D depicts the four targets bound to a single subject specific feature, resulting in four units of signal from one feature. A comparison between FIG. 1C and FIG. 1D demonstrates the signal amplification that can occur on a single feature when using a plurality of different probes directed at multiple subject targets. FIG. 1E depicts features with ordered pooling of unique probes in distinct features, resulting in array performance like that shown in FIG. 1A and FIG. 1C. FIG. 1F depicts features with random pooling of unique probes among features, resulting in an arrangement like that shown in FIG. 1B and FIG. 1D.

Figure 11:
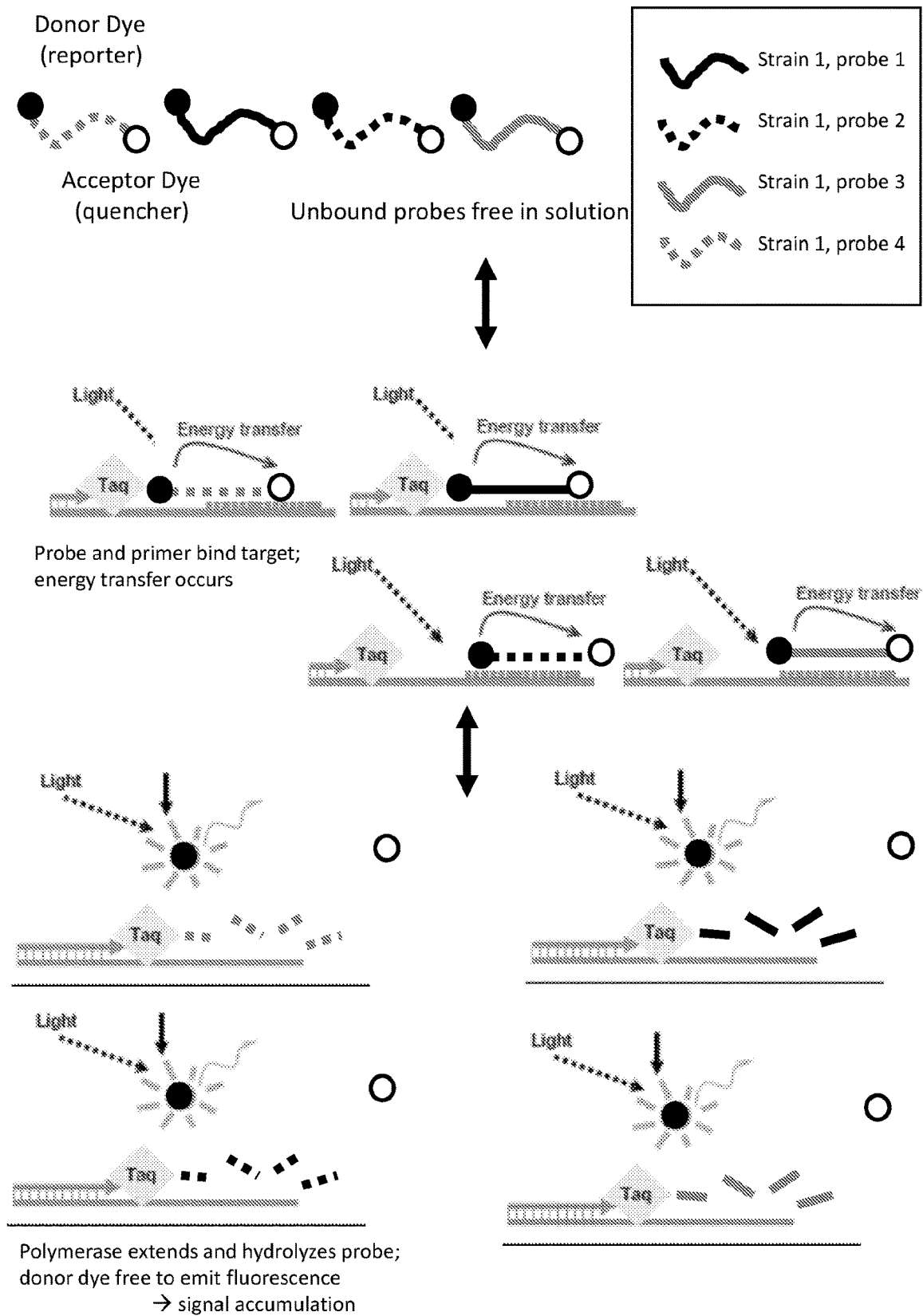
FIG. 11 depicts a reaction chamber containing four probes, each probe comprising a reporter and a quencher. Upon exposure to a light source, subsequent PCR hydrolyzes the probes, allowing the reporter to emit a fluorescence signal.

FIG. 11 illustrates another exemplary detection device. FIG. 11 depicts a reaction chamber containing four probes free in a solution, each probe comprising a reporter and a quencher. Upon exposure to a light source, subsequent PCR hydrolyzes the probes, allowing the reporter to emit fluorescence.

Multiple unique probes within a probe set or subject-specific feature can be located in an area that is smaller than or is comparable in size to the resolution of the detection system. The area encompassed by multiple unique and ordered probes could be less than the resolution of the detection system, equal to the resolution of the detection system, or the area encompassed by all the unique probes could be larger as long as the area encompassed by at least 2 of the randomly ordered unique probes in the set is roughly equivalent to, or less than, the resolution of the detection system. In such cases, signal from multiple unique probes or features can be collected or integrated in one or few pixels, or other resolution elements. Such an approach can achieve similar results as pooling non-identical probes into a single feature.

For reference, an imaging system used in microarray optical detection can have a resolution between 1 micrometer ($\mu m$) and 5 $\mu m$ per pixel or resolution element. Typically, an optically detected microarray feature that is 5 $\mu m$ in diameter or in length would be imaged with an optical system capable of between 1 $\mu m$ and 5 $\mu m$ optical resolution. Another example would be a microarray comprised of 1 $\mu m$ diameter beads space 2 $\mu m$ distant center to center. This array may be imaged with a 0.5 $\mu m$ to 1 $\mu m$ resolution optical system.

In one example, individual unique probes (e.g., DNA fragments) are pooled before being deposited on the substrate as a probe set, individual unique probes can attach to the substrate with average distances between unique probes, for example, on the order of 10 nanometers (nm) to 10's of nm from probe center to probe center. The size of a single feature comprising this probe set can be, for example, about 1 $\mu m$, 2 $\mu m$, 3 $\mu m$, 4 $\mu m$ or 5 $\mu m$ in diameter. An imaging system with a resolving power of, for example, around 1 $\mu m$ can then collect or integrate the signal from multiple individual probes within the feature into one pixel, or up to 25 pixels, or other resolution elements.

In some designs, the features can be placed with space between them containing no information, or the features can be ordered with touching boundaries, such as a checkerboard pattern of features without any area between features with no signal. For example, in the case of a 5 $\mu m$ square feature placed directly adjacent to other features, 1 $\mu m$ or 2 $\mu m$ of resolution may be required to differentiate features. If a 5 $\mu m$ bead is on the other hand spaced 15 $\mu m$ center to center with other 5 $\mu m$ beads, then a 5 $\mu m$, or possibly 10 $\mu m$ resolution imaging system could be adequate to differentiate the signals from different features on the microarray.

In another example, multiple identical probes are grouped together in a first feature smaller in size than the resolution of the imaging system, and this feature is positioned adjacent to other features targeting the same subject, where probes within a feature are identical, but are different than those in the first feature. If all the probes are encompassed within an area roughly equal to or less than the area defined by the resolving power of the detection system, then the detector can integrate the signal from all the probes into a single pixel or resolution element. This pooling of groups of identical probe types in an area of size close to or less than the resolution of imaging system can accomplish the same benefits as a random pooled set of probes.

The detection device can comprise multiple subject specific features. In some instances, the detection device comprises over 10, 100, 1000, 10,000, or over 100,000 subject specific features. In some cases, the multiple subject specific features are arranged into one or more sets of probes, wherein each set of probes identifies a different subject.

A probe can be capable of binding a target. A probe can be complementary to a target. A probe can have an affinity for a target. A probe can be combination of all three. Features directed at different subjects can comprise different probes. In some instances, non-replicate features do not share any probes with another feature. In some instances, non-replicate features do share less than 0.1%, 1%, 5%, or less than 10% of its probes with another feature.

In some cases, each set of probes has an average representation of unique probe types. In some cases, the average representation of unique probe types is about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000 or greater.

The total number of probe fragments within a set and the average representation of a single, unique probe type within a set can be controlled in order to control the specificity of a probe set and the dynamic range of the probe set. In one example, if the total number of probes is limited to approximately 1000 and the number of unique probe types in the set is 250, then the average representation of an individual probe type would be about 4. In a first example, if the DNA of four subject cells exists in the sample and about 90% of the genomic DNA from the four subject cells remains in the sample after the sample preparation process and substantially binds to the array, the signal intensity would be about 95% of the maximum intensity. Likewise, if the DNA from two subject cells was present and processed and hybridized at 95% efficiency, the signal intensity can be about 50% of the maximum intensity. In a second example, if no subject cells are present in a sample, however a non-subject organism is highly abundant in the sample at greater than 1000 cells and the DNA from the non-subject organism contains a single region that matches a single probe type, the signal generated from the single matched probe type can on average be less than about 1% of the maximum signal.

In contrast, given the same two examples above, if the number of unique individual probe types is set at 10 and the total number of probe fragments is 10,000, the average probe representation would be about 1000. In this scenario, given example A above, the signal intensity would be less than 1% of the maximum signal, possibly resulting in a false negative determination. In the same scenario, but given example B from above, the signal intensity would be about 10% of the maximum signal resulting in a possible false positive determination. The lower limit of detection, in terms of target cells that can be detected, could then be compromised in order to increase the specificity of the system, that is, the ability to reject false positive calls due to binding errors in one of more of the probes within the set.

In some aspects, the total number of probes in a subject-specific feature is controlled. Methods of controlling the total number of probes in a subject-specific feature include, without limitation, controlling the total feature size and controlling individual probe spacing within a subject-specific feature.

In some aspects, probes can be designed to detect false positives. For example, probes can be designed by designing probe sets wherein the individual probes within the probe set are designed with one or more bases that are mismatched to individual probes in other probe sets. In some cases, the probe sets are complementary. In other cases, the probe sets are not complementary. In another example, a probe set can be designed to search for a subject organism that has multiple similar strains. In this example, a probe set could be added to detect individual sequences contained in strains that are not target but have genomes that are very close to that of the target with one or more individual unique characteristics.

Design of probe sets can also include empirical screening steps in order to learn more about possible false positive behavior. This could be based on adding controls for various types of genomic DNA that could be found in nature and that can be part of the non-subject material included in the hybridization activity. These probe sets can be screened individually or as a set.

The features (e.g., array spots, electrodes, wells) of the detection device can each be different including, without limitation, containing a different number of probes, different types of probes, different subject-specific features, different average representations of unique probes, and the like. In one non-limiting example, a detection device can include a plurality of reaction chambers to detect multiple subject-specific features. Each subject-specific feature can include a set of probes, with each set including a plurality of unique probes. In some features, the set of probes can include a low average representation of unique probes for a target subject that could be used to measure the sensitivity of the detection device. In other features on the same detection device, the set of probes can include a high average representation of unique probes for the same target subject that could be used to measure the abundance of the target nucleic acids in the sample. Any number of sensitivity and/or abundance features can be designed into a detection device.

The detection devices can be subjected to multiple probing experiments for serial comparisons of the hybridization strengths of different sources (e.g., from two different microbiome samples). For example, the detection device can be subjected to multiple serial hybridization reactions, and optionally multiple read reactions, each reaction optimized for the characteristics of different probe sets.

The probes can be designed to hybridize to target polynucleotides (target nucleic acids, or targets). The target polynucleotides can be a genomic sequence. The target polynucleotides can be a non-coding region of a genome. The target can be a genomic feature. The target can be mitochondrial DNA. The target can be DNA from a plasmid. The target can be a variant. The target can be a conserved region of a genome or a region linked to pathogenicity.

The target can be a region of a genome which is distinguishable from another genome. A target can be a polynucleotide which is unique to a subject within a population of subjects. A target can be a polynucleotide within a microbiome which is distinct to a particular species represented in that microbiome.

An exemplary protocol for probe design is as follows. First, a length criterion (e.g., 35 bases) is chosen for the probe set. Second, a set of k-mers of the selected length is created from the target genome by sequentially marching through the subject genome. Third, the k-mers are compared against other genomes of the same species (e.g., via blasting). Fourth, the k-mers are compared against all other genomes (i.e., not the same species) publicly available, such as human, bacterial, viral, and others (e.g., via blasting). In some cases, the third and fourth steps can be conducted together, although this can result in a very small set for some species (e.g., *E. coli*). Fifth, a short list of candidate k-mers that are unique is created. Additionally, the middle base of these unique probes can be changed to each orthogonal base (1 k-mer results in 3 mismatch k-mers), and the mismatch k-mers can also be compared against all other genomes publicly available (e.g., via blasting) and/or against other genomes of the same species. Sixth, candidates are tested for self complementarity (i.e., whether the probe will bind to itself). Seventh, melt temperature is evaluated based on the free energy of the single strand. Eighth, k-mers are ranked based on level of uniqueness (e.g., percent of sequence that is unique). Additionally, k-mers can be filtered for other traits, such as GC content. For example, in some cases, only k-mers with GC content <60% are included. Ninth, candidates are tested empirically by hybridizing to selected genomes of the same species. Tenth, based on these results, a final candidate pool is chosen.

Probes can be designed to be complementary to a known nucleic acid sequence. In some cases, subject polynucleotides can be sequenced prior to probe design in order to determine the sequence of the polynucleotides. Once the polynucleotides have been sequenced, probes can be designed to target the subject polynucleotides. In some cases, the subject polynucleotides comprise sequences that are found in a subject genome. In this example, the subject genome can be sequenced and probes can be designed to target polynucleotides within the genome. In some instances, a list of targets can be generated by determining non-overlapping genomic regions between two or more subjects. In some cases, targets are identified by comparing assemblies. Sequencing methods can comprise capillary sequencing, next generation sequencing, Sanger sequencing, sequencing by synthesis, single molecule nanopore sequencing, sequencing by ligation, sequencing by hybridization, sequencing by nanopore current restriction, or a combination thereof. Sequencing by synthesis can comprise reversible terminator sequencing, processive single molecule sequencing, sequential nucleotide flow sequencing, or a combination thereof. Sequential nucleotide flow sequencing can comprise pyrosequencing, pH-mediated sequencing, semiconductor sequencing or a combination thereof. Conducting one or more sequencing reactions comprises untargeted sequencing (e.g., whole genome sequencing) or targeted sequencing (e.g., exome sequencing).

The sequencing methods can comprise Maxim-Gilbert, chain-termination or high-throughput systems. Alternatively, or additionally, the sequencing methods can comprise Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT(TM) sequencing, Polony sequencing, DNA nanoball sequencing, VisiGen Biotechnologies approach, or a combination thereof. Alternatively, or additionally, the sequencing methods can comprise one or more sequencing platforms, including, but not limited to, Genome Analyzer IIx, HiSeq, Next- Seq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, MA), nanopore-based sequencing platforms developed by Genia Technologies, Inc., and the Oxford Nanopore MinION.

In some cases, sequence or gene expression databases are queried to identify a known nucleic acid sequence of a target subject. Non-limiting examples of sequence or gene expression databases include GenBank at NCBI, the European Molecular Biology Laboratory (EMBL), the DNA DataBank of Japan (DDBJ), ENSEMBL, the Ashbya Genome Database (AGD), BioCyc, CleanEx, CYGD, Dictybase, EchoBase, EcoGene, euHCVdb, EvoTrace, FlyBase, GeneCards, GeneDB, GeneFarm, GenoList, Gramene, HGNC, Hlnv-DB, HOGENOM, KEGG, MaizeGDB, MEROPS, MGD, NMPDR, NCBI Nucleotide db, NCBI RefSeq, PANTHER, PCCDB, PeroxiBase, Pfam, PhosphoSitePlus, PlasmoDB, PptaseDB, PseudoCap, RGD, SGD, TAIR, TIGR/SCVI, UniGene, VectorBase, WormBase, and Z-FIN.

In some cases, at least one of the plurality of probes comprises a payload molecule. In other cases, at least one of the plurality of probes comprises at least two payload molecules. In some cases, the payload molecule is polyethylene glycol (PEG) or a derivative thereof. In some embodiments, at least two of the plurality of probes comprises a different payload molecule. In some embodiments, the different payload molecules are different sizes. In some embodiments, at least two of the plurality of probes comprises a different number of payload molecules. In some embodiments, a probe can comprise one, two, three, four, five, six, seven, eight, nine, ten, or more than ten payload molecules. For example, two PEG molecules could be attached to each probe in one set of probes, and three PEG molecules could be attached to each probe in a second set of probes.

In some cases, a probe is bound to a synthetic nucleic acid scaffold. In some cases, the payload molecule is bound to the synthetic nucleic acid scaffold.

In some embodiments, the detection devices described herein further comprise one or more sets of secondary probes, wherein each set of said one or more sets of secondary probes comprise a plurality of secondary probes, and wherein each set of said one or more sets of secondary probes binds to a region of a nucleic acid near the target nucleic acid.

The region of the nucleic acid near the target nucleic acid can be upstream or downstream of the target nucleic acid. The region of the nucleic acid near the target nucleic acid can be separated from the target nucleic acid by less than 10 bp. The region of the nucleic acid near the target nucleic acid can be separated from the target nucleic acid by less than 10 bp, less than 20 bp, less than 30 bp, less than 40 bp, less than 50 bp, or less than 100 bp.

In some cases, the secondary probes are immobilized to a surface of the detection device. In some embodiments, the surface of the detection device is an electrode. In some instances, the electrode comprises gold, iridium, platinum, copper or a combination thereof In some instances, the detection device further comprises a plurality of electrodes. In some cases, the surface of the detection device is an array.

In other cases, the secondary probes are not immobilized to a surface of the detection device.

In some instances, at least one of the plurality of secondary probes comprises a guide nucleic acid (gNA), a nucleic-guided nuclease system protein, or a complex thereof. In some cases, the gNA binds to the target nucleic acid. In some cases, the guide nucleic acid (gNA): nucleic acid-guided nuclease system protein complex binds to the target nucleic acid. In some embodiments, the nucleic acid-guided nuclease system protein is a CRISPR/Cas system protein. In some embodiments, the CRISPR/Cas system protein is selected from the group consisting of Cas9, CasX, CasY, Cpf1, Cas3, Cas8a-c, Cas10, Cse1, Csy1, Csn2, Cas4, Csm2, and Cm5. In some embodiments, the nucleic acid-guided nuclease system protein is a dead nucleic acid-guided nuclease system protein. In some embodiments, the CRISPR/Cas system protein is a dead CRISPR/Cas system protein. In some embodiments, the CRISPR/Cas system protein is dCas9. In some embodiments, the nucleic acid-guided nuclease system protein is a nucleic acid-guided nuclease system nickase protein. In some embodiments, the CRISPR/Cas system protein is a CRISPR/Cas system nickase protein. In some embodiments, the nucleic acid-guided nuclease system protein exhibits reduced off-target binding. In some cases, the CRISPR/Cas system protein opens a double stranded DNA (dsDNA), allowing binding of the DNA comprising the target nucleic acid to gNA. In some embodiments, the CRISPR/Cas system protein opens the dsRNA at room temperature.

In some embodiments, the gNA comprises a label. In some embodiments, the nucleic-guided nuclease system protein comprises a label. In some embodiments, the gNA and the nucleic-guided nuclease system protein comprises the same label. In some embodiments, the gNA and the nucleic-guided nuclease system protein comprise different labels.

In some cases, at least one of the plurality of secondary probes is labeled with at least one detectable label. In some cases, the label is selected from the group consisting of an enzyme, an enzyme substrate, an antibody, an antigen binding fragment, a peptide, a chromophore, a lumiphore, a fluorophore, a chromogen, a hapten, an antigen, a radioactive isotope, a magnetic particle, a nanoparticle (e.g., gold nanoparticles), a quantum dot, a barcode (e.g., nucleic acid barcode), an active site, a binding site, a redox active marker group, an aptamer, hydrophobic species, hydrophilic species, one member of a binding pair, a donor dye (reporter), an acceptor dye (quencher), an organometallic compound, and combinations thereof.

Methods

In some embodiments, the methods described herein are methods for identifying a target subject in a sample comprising a plurality of different subjects. In some embodiments, the methods described herein are methods for identifying a plurality of target subjects in a sample comprising a plurality of different subjects. In some embodiments, the target subject comprises at least one target nucleic acid. In some embodiments, the plurality of target subjects comprise a plurality of target nucleic acids, wherein each of the plurality of target subjects comprise at least one target nucleic acid.

In some aspects, the methods described herein include providing a sample comprising a plurality of different subjects. In some cases, the sample includes a plurality of nucleic acids derived from the plurality of different subjects. In some cases, the plurality of nucleic acids includes at least one target nucleic acid from at least two or more of the plurality of different subjects.

In some aspects, the methods further include extracting nucleic acids from the plurality of subjects. In some aspects, the methods also include fragmenting the nucleic acids extracted from the plurality of subjects. Any additional processing steps can be performed on the nucleic acids prior to application to the detection device. In some cases, the nucleic acids can be modified prior to hybridization to the detection device. For example, the nucleic acids can be labeled as described herein. Additionally, or alternatively, target nucleic acids can be enriched, for example, by the use of capture probes or an amplification step. In other examples, non-target nucleic acids can be depleted from the sample prior to hybridization.

In further aspects, the methods include hybridizing the plurality of nucleic acids to a detection device. The detection device can be designed as described herein. After hybridization, the methods can further include any number of wash steps. For example, after hybridizing the nucleic acids to the probes of the detection device, the detection device can be washed one or more times with e.g., a buffer or wash solution, to remove any non-hybridized nucleic acids. Non-hybridized nucleic acids can be discarded or collected for further processing.

In some aspects, the hybridized nucleic acids can be detected, for example through changes in electrical conductance, capacitance, or resistance. In some cases, the detection device is imaged. In some examples, a read buffer is added to the detection device prior to the detecting. The read buffer can include a reagent that generates a detectable signal upon application to the hybridized nucleic acids. In other examples, the nucleic acid molecules are detectably labeled.

Figure 7A:
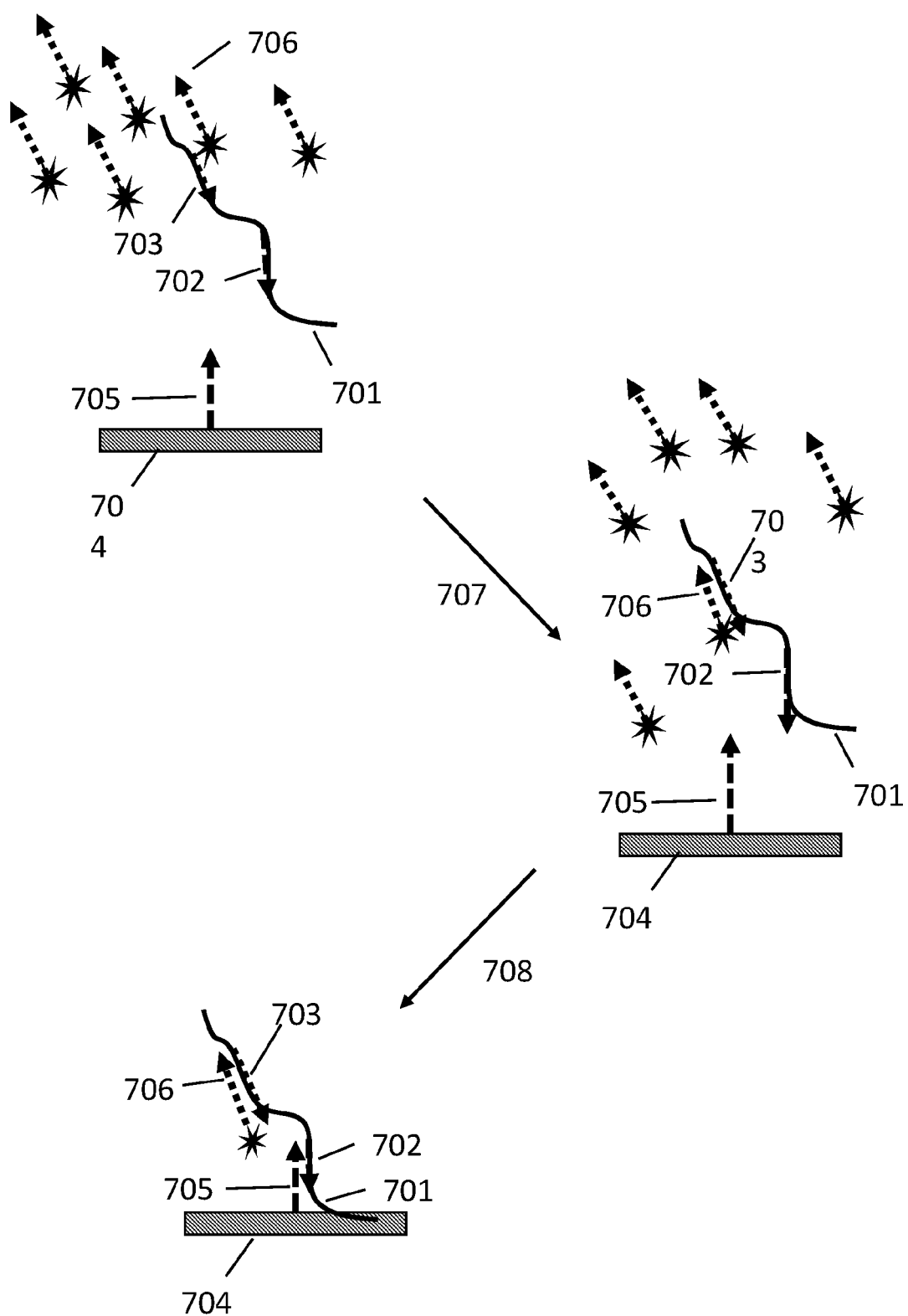
FIG. 7A depicts hybridization and detection of a target nucleic acid via hybridization at separate capture and detection sequences.

In some aspects, an additional specificity step can be added. In one example, a ligation step after hybridization can distinguish single base mismatches. Specificity can also be increased by adding additional hybridization steps for capture, detection, or both. For example, FIG. 7A shows a target nucleic acid 701 comprising a capture sequence 702 and an adjacent or nearby detection sequence 703. An array substrate 704 with a capture oligonucleotide 705 (e.g., with sequence complementary to the capture sequence) can be used to hybridize to and capture 707 the target nucleic acid. A detection oligonucleotide 706 (e.g., fluorescently labeled) can be used to hybridize 708 to the detection sequence of the target nucleic acid enable detection of the target nucleic acid. The detection oligonucleotide can be in free solution with the unlabeled target nucleic acid. Hybridization of the detection oligonucleotide to the target nucleic acid can occur prior to, during, or subsequent to capture of the target nucleic acid on the array. The detection oligonucleotide can hybridize to any perfectly (or almost perfectly) complementary sequence. The detection can be present at a relatively high concentration, such that it can hybridize quickly. Because the capture sequence and the detected sequence are nearby, the likelihood that these two sequences are coincident on any small fragment of DNA will be low, therefore lowering the possibility that a detected signal is nonspecific.

In some cases, the capture sequence and detection sequences are positioned closely enough together to reduce the chance that they will be located on separate fragments of the target nucleic acid.

Figure 7B:
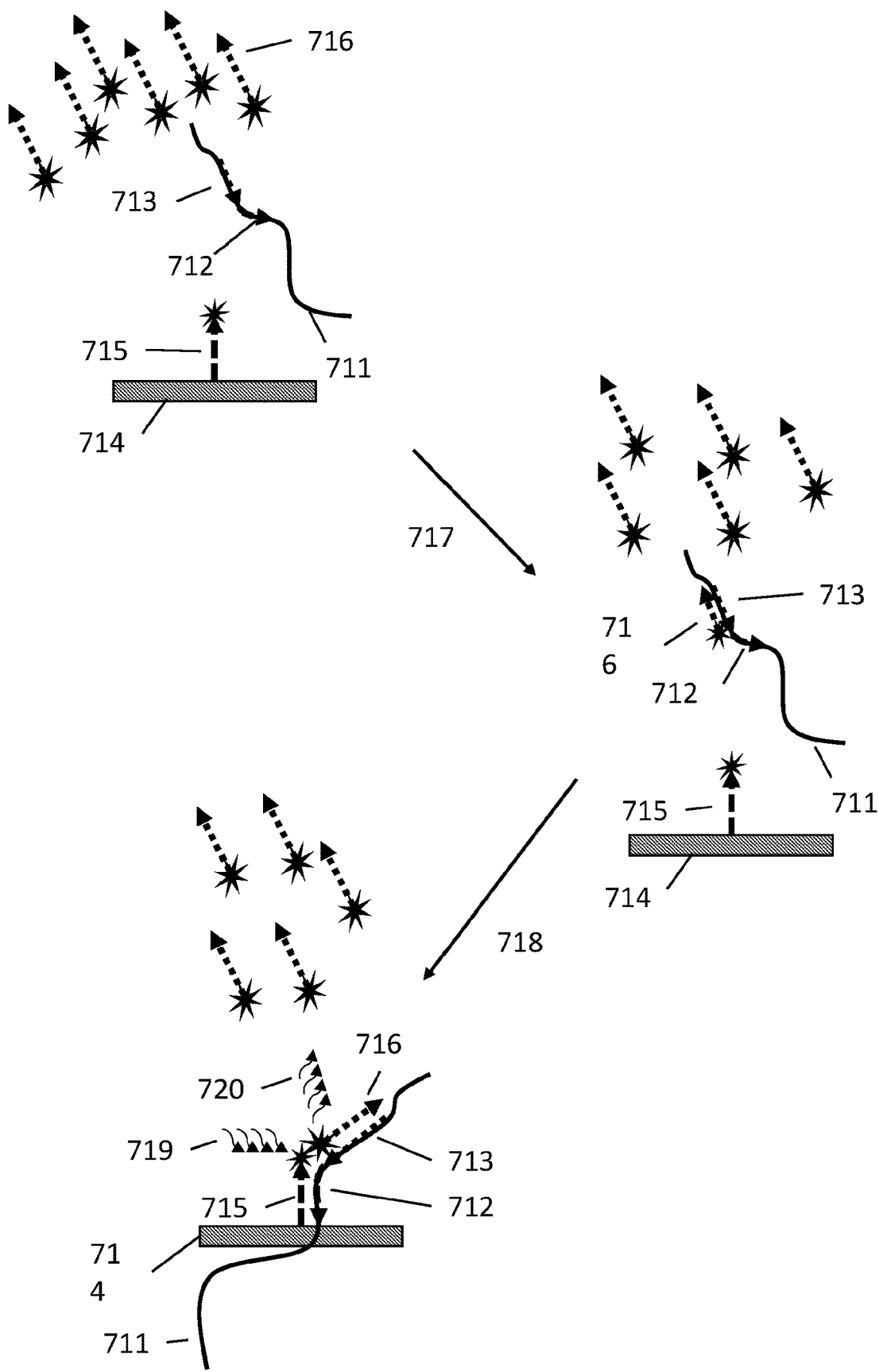
FIG. 7B depicts FRET signal detection of a target nucleic acid via hybridization at separate capture and detection sequences.

If the capture and detected sequence are adjacent, use of energy transfer dye combinations (e.g., FRET) can reduce background. In one example, shown in FIG. 7B, the donor dye is on the capture oligo 715 3' end and the acceptor dye is on the detection oligonucleotide 716 at the 5' end. A target nucleic acid 711 comprising a capture sequence 712 and a detection sequence 713 can be captured on an array substrate 714. Hybridization of both the capture oligonucleotide 717 and of the detection oligonucleotide 718 to the target nucleic acid can bring the donor and acceptor dyes into FRET distance of each other. Once within FRET distance, excitation light 719 can excite the FRET donor, which in turn can excite the FRET acceptor via resonance energy transfer, allowing production of a FRET signal 720. The location and positioning of the donor and acceptor dyes can be varied. For example, the donor dye can be on the detection oligonucleotide and the acceptor dye can be on the capture oligonucleotide. Dyes can be bound to the array surface at locations other than the capture oligonucleotide. These ideas are scalable to multiple capture loci in the same feature.

Multiple capture and/or detection sequences can be employed for a single target nucleic acid. For example, FIG. 7C shows an exemplary schematic of a target nucleic acid 731 comprising three capture sequences 732 733 734. The array substrate 735 similarly comprises three capture oligonucleotides 736 737 738 within one feature. After hybridization 739, each of the capture sequences is hybridized to its corresponding capture oligonucleotide. Local conditions (e.g., buffer composition, temperature, pH) can be configured such that hybridization of fewer than all of the capture sequences is insufficient to keep the target nucleic acid bound to the array, increasing the specificity of the analysis. The multiple capture sequences can operate cooperatively if the correct target sequences are present, but independently if interaction is nonspecific. Once a region is captured, the other adjacent regions can be captured quickly and be relatively difficult to remove (e.g., due to local high concentration of the capture sequences).

Similarly, multiple detection sequences and corresponding detection oligonucleotides can be employed such that the presence of all detection oligonucleotides is needed for a positive signal. In one example, each detection oligonucleotide has a different emission wavelength, and a signal is detected for each different emission wavelength in order to register a positive signal. In another example, a FRET pair of detection oligonucleotides can be used, and hybridization to detection sequences on a target nucleic acid can bring them within FRET distance of each other. Different detection oligonucleotides can be used to recognize different traits. For example, one detection oligonucleotide can be used to indicate the identity (e.g., species, strain, or individual) of the subject, while another detection oligonucleotide can be used to indicate a gene, mutation, or other characteristic of the subject (e.g., antibiotic resistance, virulence).

In some aspects, the identity of the subjects present in the original sample can be determined based on detecting the presence of the nucleic acids in the sample. In some cases, targets for a specific subject can be designed to detect a specific strain. In some cases, targets can include probes for the subject species, or other regions contained within the subject that are unique in other ways, such as representing conserved regions or regions that are linked to pathogenicity. In some cases, targets can include probes capable of differentiating a specific individual, such as a specific person. Individual probe sets can uniquely identify a specific individual. In other cases, the identification of an individual may not be unique, but can provide a valuable call confidence level based on level of uniqueness. In some cases, the confidence level of an individual call can be about 50%, 55%, 60%, 65%, 70%, 75%, 80%, 85%, 90%, 95%, 96%, 96%, 98%, 99%, 99.9%, 99.99%, or 99.999%. In some cases, the confidence level of an individual call can be at least about 50%, 55%, 60%, 65%, 70%, 75%, 80%, 85%, 90%, 95%, 96%, 96%, 98%, 99%, 99.9%, 99.99%, or 99.999%. In some cases, the confidence level of an individual call can be at most about 50%, 55%, 60%, 65%, 70%, 75%, 80%, 85%, 90%, 95%, 96%, 96%, 98%, 99%, 99.9%, 99.99%, or 99.999%.

In some cases, the results are provided on a report. The report can list the subjects identified from the plurality of subjects in the original sample. In cases where a subject is represented by multiple features such as a strain specific feature, a species specific feature, and a feature comprised of conserved regions that exist within the subject, the report can list whether these other features were also detected. The ultimate positive call can then be based on confidence levels calculated based on whether all, none, of some of the features linked to the subject were detected.

In some aspects, the methods include the ability to store the full sample after detection. This can be accomplished, for example, by separating the sample at a time point in the sample preparation process into an A sample and a B sample. The A sample could proceed through the full sample preparation process whereas the B sample could be diverted to a reservoir for later processing. In another example, a non-hybridized portion of the sample could be diverted to a reservoir after the hybridization process by, for example, washing the detection device to remove non-hybridized nucleic acids. In yet another example, the hybridized nucleic acids could be de-hybridized and diverted into a reservoir for later querying.

Techniques of the present disclosure can be conducted using automated operation for some or all of the steps. For example, in some cases, the only user-conducted step is sample loading, with all other steps such as sample preparation, fluid handling, assaying, detection, and reporting of results occurring automatically. In other cases, even sample loading can be conducted automatically. For example, laboratory automation equipment or environmental sampling equipment can be used to provide a sample to a device for analysis.

Detection

In some aspects of the disclosure, binding of a target nucleic acid to a probe of the detection device is detected. Detection can encompass any method known to one of skill in the art. In some cases, detection involves detecting a detectable label present on the target nucleic acid molecule, the probe, or both. In other cases, detection involves detecting a signal that is generated based on an interaction of the target nucleic acid molecule and the probe. In some embodiments, the signal is a fluorescence signal, an electrochemical signal, or a measure of current impedance.

Labels can be detectable themselves, or can allow binding of another detectable species. Labels that are not detectable by themselves can be subsequently contacted with a detectable species. For example, target nucleic acids can be labeled with biotin, and subsequently bound to a streptavidin-conjugated fluorophore for detection. In another example, target nucleic acids can be labeled with nucleic acid barcodes; subsequently, the nucleic acid barcode sequences can be amplified and detected. Detection modalities can include, but are not limited to, optical detection (including FRET, fluorescence lifetime, and other optical properties), electrical detection, magnetic detection, radio-label detection, sequencing, size detection (e.g., via electrophoretic separation), surface plasmon resonance (SPR), Raman spectroscopy, and mass spectrometry.

In some cases, the signal is a fluorescence-resonance energy transfer (FRET)-based signal. In this example, both target nucleic acid molecules and probes are labeled with one or more fluorescent labels. The one or more fluorescent labels can be one or more FRET pairs. The one or more FRET pairs can comprise at least one FRET donor (reporter) and at least one FRET acceptor (quencher). In some cases, the FRET donor is attached to the target nucleic acid molecule and the FRET acceptor is attached to the probe. In other cases, the FRET acceptor is attached to the target nucleic acid molecule and the FRET acceptor is attached to the probe. In other cases, the FRET acceptor and the FRET donor are attached to the probe. The FRET donor and acceptor can be attached to either end (3' or 5') of the target nucleic acid molecule and the probe. In some cases the FRET donor (reporter) is any suitable reporter, such as those shown in Table 1. In some cases the FRET acceptor (quencher) is any suitable quencher, such as those shown in Table 2. In some cases, the FRET donor is Cy3 and the FRET acceptor is Cy5. Other non-limiting examples of FRET pairs include: FITC/TRITC, EGFP/Cy3, CFP/YFP, and EGFP/YFP.

In some cases, the method further comprises exposing the detection device to a light source. In some cases, the light source is a fluorescent light source. Exposure to a light source results in energy transfer from the reporter to the quencher. In some cases, detection further comprises performing polymerase chain reaction (PCR) of a nucleic acid sequence comprising the target nucleic acid. In some instances, the PCR is digital PCR (dPCR). In some instances, the digital PCR is digital droplet PCR (ddPCR). In some cases, performing PCR results in the hydrolysis of the one or more sets of probes when the one or more sets of probes are bound to the target nucleic acid. Hydrolysis of the one or more sets of probes results in the separation of the reporter and the quencher, further resulting in the emittance of a fluorescence signal by the reporter. In some cases, the fluorescence signal is optically detected using a CCD, CMOS, or SPAD camera.

In some cases, the method further comprises applying a voltage to the detection device. In some cases the signal is an electrochemical signal. In this example, a secondary (capture) probe is bound to an electrode, which binds to a region of a nucleic acid near the target nucleic acid. When a target nucleic acid binds to an unbound probe comprising a detectable label, such as a ferrocene label, and this complex subsequently binds to the secondary probe bound to the electrode, application of a voltage to the electrode can result in a detectable electrochemical signal.

In some cases, the reaction chamber comprises at least one pore. In some cases, the reaction chamber comprises at least two pores. In some cases, the reaction chamber comprises a first pore and a second pore. In this example, the first pore comprises a first electrode emitting a first voltage and the second pore comprises a second electrode emitting a second voltage. When a target nucleic acid binds to a probe or a label, application of a first voltage of the first pore and a second voltage of the second pore to a sample can result in a detectable current impedance signature.

In other cases, detection involves detecting a detectable label present on the target nucleic acid. In this example, a signal can be detected only when a detectably-labeled target nucleic acid molecule is bound to a probe. In some cases, the target nucleic acid molecule is 5'-labeled with Cy5. In some cases, non-labeled hybridization binding can be detected by, for example, detecting the difference in surface conditions over an interferometric oscillator, index of refraction differences in an optical path, or direct detection using scanning electron microscopy (SEM) techniques.

If optical detection is utilized, the detection device can be the surface of an optical detector such as a CMOS camera or the detection device can be within a flow cell that is probed by an external optical system. In the case of optical fluorescence detection, conventional fluorescent optical detection architectures can be used, including fluorescent confocal microscopy. If the probe is immobilized directly on a CMOS detector, the CMOS detector can have a layer between the probe and the CMOS detector that blocks the excitation light of the system and allows the light from the chosen dye to pass.

Computer Systems

Figure 3:
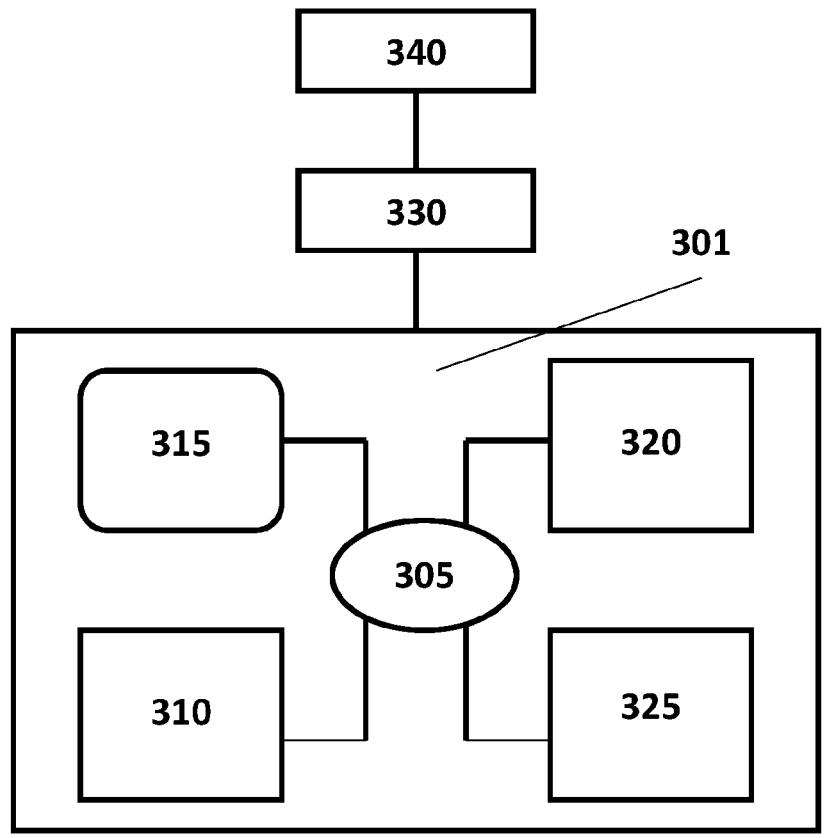
FIG. 3 depicts an exemplary computer system suitable for performing the methods disclosed herein.

The systems of the disclosure can comprise one or more computer systems. Techniques and devices of the present disclosure can employ computer systems for operation, automation, sample processing, data processing, transmission of data, analysis, presentation of results, and other functions. FIG. 3 shows a computer system 301 programmed or otherwise configured to implement the methods of the disclosure, such as receiving data and identifying the presence or absence of subjects in a sample. The computer system 301 includes a central processing unit (CPU, also "processor" and "computer processor" herein) 305, which can be a single core or multi core processor, or a plurality of processors for parallel processing. The computer system 301 also includes memory 310 (e.g., random-access memory, read-only memory, flash memory), electronic storage unit 315 (e.g., hard disk), communications interface 320 (e.g., network adapter) for communicating with one or more other computer systems, and peripheral devices 125, such as cache, other memory, data storage and/or electronic display adapters. The memory 310, storage unit 315, interface 320 and peripheral devices 325 are in communication with the CPU 305 through a communications bus (solid lines), such as a motherboard. The storage unit 315 can be a data storage unit (or data repository) for storing data. The computer system 301 is operatively coupled to a computer network ("network") 330 with the aid of the communications interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330 in some cases, with the aid of the computer system 301, can implement a peer-to-peer network, which can enable devices coupled to the computer system 301 to behave as a client or a server. The computer system does not have to be physically proximate to the device; it can be in communication with the device through wired or non-wired modalities.

The computer system 301 can be in communication with a processing system 335. The processing system 335 can be configured to implement the methods disclosed herein, such as identifying the presence of one or more target nucleic acid sequences or classifying a plurality of subjects on a report. The processing system 335 can be in communication with the computer system 301 through the network 330, or by direct (e.g., wired, wireless) connection. The processing system 335 can be configured for analysis, such as nucleic acid sequence analysis.

Methods and systems as described herein can be implemented by way of machine (or computer processor) executable code (or software) stored on an electronic storage location of the computer system 301, such as, for example, on the memory 310 or electronic storage unit 315. During use, the code can be executed by the processor 305. In some examples, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code, can be compiled during runtime or can be interpreted during runtime. The code can be supplied in a programming language that can be selected to enable the code to execute in a pre-compiled, as-compiled or interpreted fashion.

Aspects of the systems and methods provided herein can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, can take many forms, including but not limited to, a tangible storage medium, a carrier wave medium or physical transmission medium. Non-volatile storage media include, for example, optical or magnetic disks, such as any of the storage devices in any computer(s) or the like, such as can be used to implement the databases, etc. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

The computer system 301 can include or be in communication with an electronic display that comprises a user interface (UI) for providing, for example, a customizable menu of genetic variants that can be analyzed by the methods of the disclosure. Examples of UI's include, without limitation, a graphical user interface (GUI) and web-based user interface.

In some cases, the computer system 301 includes a display to provide visual information to a user. In some cases, the display is a cathode ray tube (CRT). In some cases, the display is a liquid crystal display (LCD). In further examples, the display is a thin film transistor liquid crystal display (TFT-LCD). In some cases, the display is an organic light emitting diode (OLED) display. In various further examples, on OLED display is a passive-matrix OLED (PMOLED) or active-matrix OLED (AMOLED) display. In some cases, the display is a plasma display. In other cases, the display is a video projector. In still further cases, the display is a combination of devices such as those disclosed herein. The display can provide one or more biomedical reports to an end-user as generated by the methods described herein.

In some cases, the computer system 301 includes an input device to receive information from a user. In some examples, the input device is a keyboard. In some examples, the input device is a pointing device including, by way of non-limiting examples, a mouse, trackball, track pad, joystick, game controller, or stylus. In some cases, the input device is a touch screen or a multi-touch screen. In other cases, the input device is a microphone to capture voice or other sound input. In other cases, the input device is a video camera to capture motion or visual input. In still further examples, the input device is a combination of devices such as those disclosed herein.

The computer system 301 can include or be operably coupled to one or more databases. The databases can comprise genomic, proteomic, pharmacogenomic, biomedical, and scientific databases. The databases can be publicly available databases. Alternatively, or additionally, the databases can comprise proprietary databases. The databases can be commercially available databases. The databases include, but are not limited to, MendelDB, PharmGKB, Varimed, Regulome, curated BreakSeq junctions, Online Mendelian Inheritance in Man (OMIM), Human Genome Mutation Database (HGMD), NCBI dbSNP, NCBI RefSeq, GENCODE, GO (gene ontology), and Kyoto Encyclopedia of Genes and Genomes (KEGG).

Data can be produced and/or transmitted in a geographic location that comprises the same country as the user of the data. Data can be, for example, produced and/or transmitted from a geographic location in one country and a user of the data can be present in a different country. In some cases, the data accessed by a system of the disclosure can be transmitted from one of a plurality of geographic locations to a user. Data can be transmitted back and forth among a plurality of geographic locations, for example, by a network, a secure network, an insecure network, an internet, or an intranet.

The total system can be designed in a variety of ways that can use three main components each with individual modules. The components can include a user interface, a hardware platform and a consumable. In one example, the user interface can be incorporated into the hardware allowing direct interaction with the system and the consumable component can include the reagents necessary for performing the methods of the disclosure. More complex architectures could be designed using a remote, wirelessly-connected user interface that contains all or none of the system intelligence, one or more multiple hardware components connected via automation or human interaction, and a consumable that is fully contained, including all reagents and all or part of the detection system required to convert the biological information present in the assay to digital or analog information that can be transferred to a computer for processing and reporting. The system can contain multiple additional modules including, without limitation, scheduling modules that control a multitude of samples as they are serially or in parallel processed by the system, and quality assurance modules that ensure the system is operating properly through internal function checks or tests using biological control.

Figure 9A:
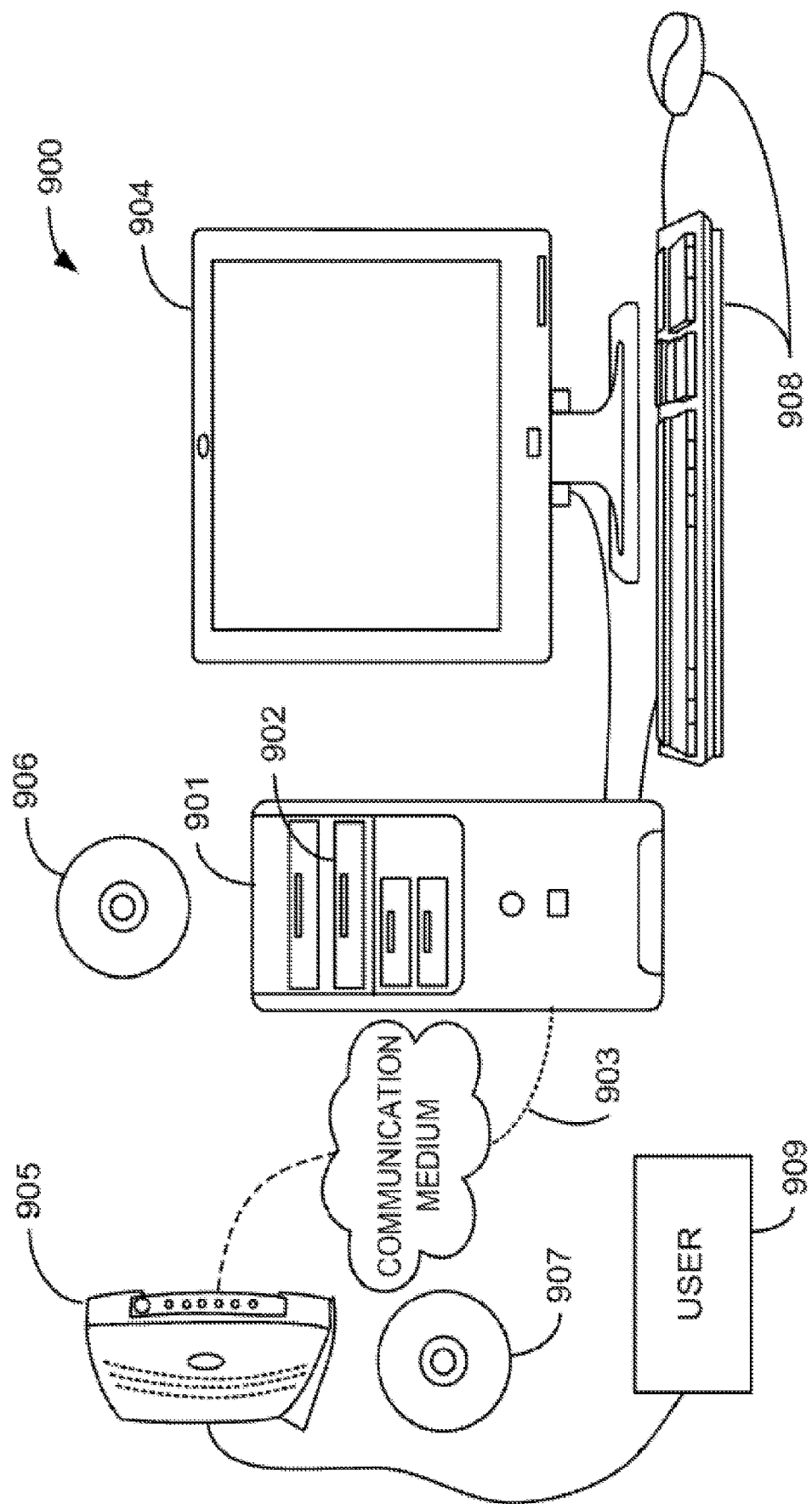
FIG. 9A depicts an exemplary computer system.

The computer system 900 illustrated in FIG. 9A may be understood as a logical apparatus that can read instructions from media 906 and/or a network port 903, which can optionally be connected to server 905 having fixed media 907. The system, such as shown in FIG. 9A can include a CPU 901, disk drives 902, optional input devices 908 such as keyboard and/or mouse, and optional monitor 904. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 909 as illustrated in FIG. 9A.

Figure 9B:
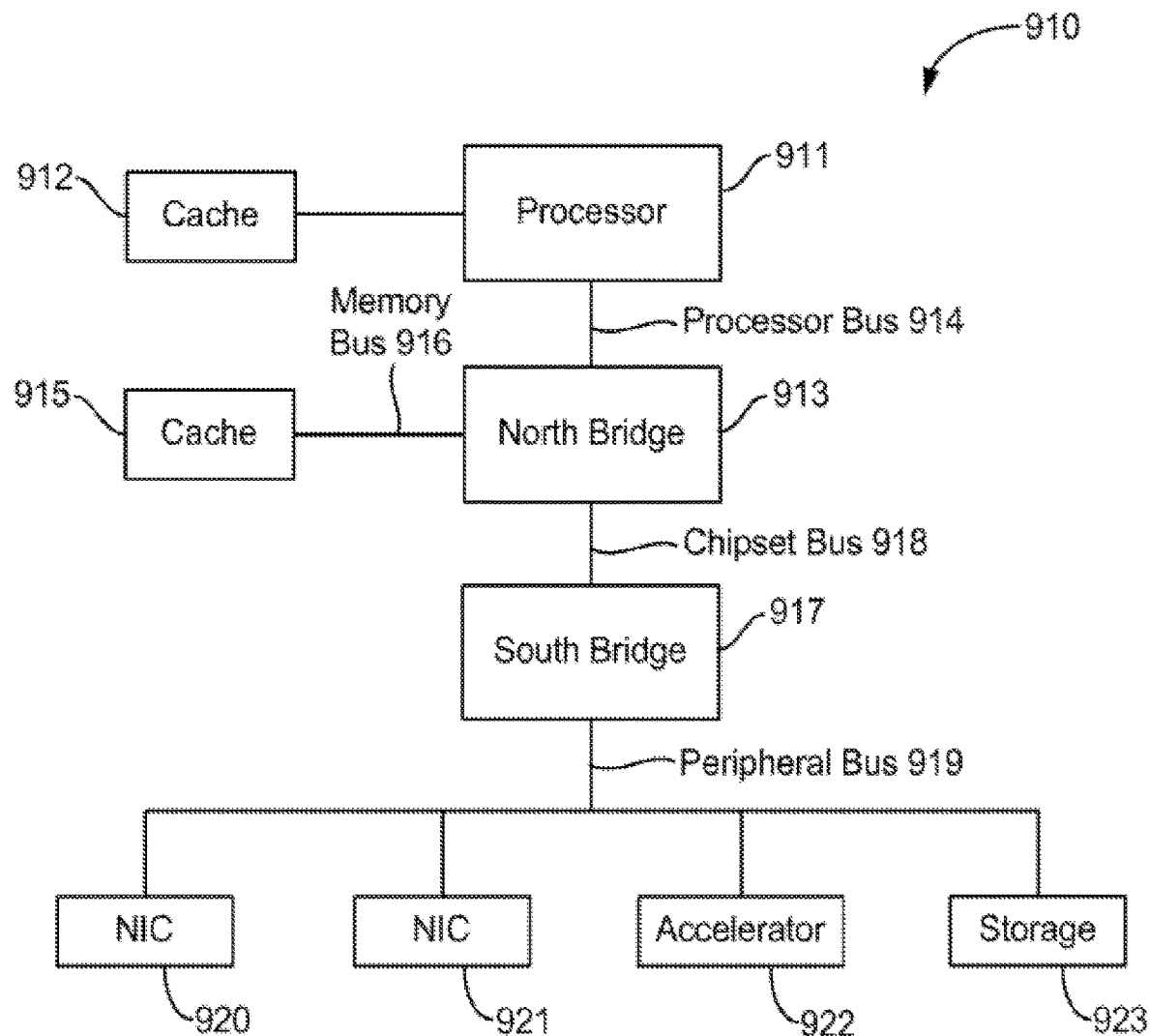
FIG. 9B depicts an exemplary architecture of a computer system.

FIG. 9B is a block diagram illustrating a first example architecture of a computer system 910 that can be used in connection with example embodiments of the present disclosure. As depicted in FIG. 9B, the example computer system can include a processor 911 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices. As illustrated in FIG. 9B, a high speed cache 912 can be connected to, or incorporated in, the processor 911 to provide a high speed memory for instructions or data that have been recently, or are frequently, used by processor 911. The processor 911 is connected to a north bridge 913 by a processor bus 914. The north bridge 913 is connected to random access memory (RAM) 915 by a memory bus 916 and manages access to the RAM 915 by the processor 911. The north bridge 913 is also connected to a south bridge 917 by a chipset bus 918. The south bridge 917 is, in turn, connected to a peripheral bus 919. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 919. In some alternative architectures, the functionality of the north bridge can be incorporated into the processor instead of using a separate north bridge chip. In some embodiments, system 910 can include an accelerator card 922 attached to the peripheral bus 919. The accelerator can include field programmable gate arrays (FPGAs) or other hardware for accelerating certain processing. For example, an accelerator can be used for adaptive data restructuring or to evaluate algebraic expressions used in extended set processing. Software and data are stored in external storage 923 and can be loaded into RAM 915 and/or cache 912 for use by the processor. The system 910 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure. In this example, system 910 can also include network interface cards (NICs) 920 and 921 connected to the peripheral bus for providing network interfaces to external storage, such as Network Attached Storage (NAS) and other computer systems that can be used for distributed parallel processing.

Figure 9C:
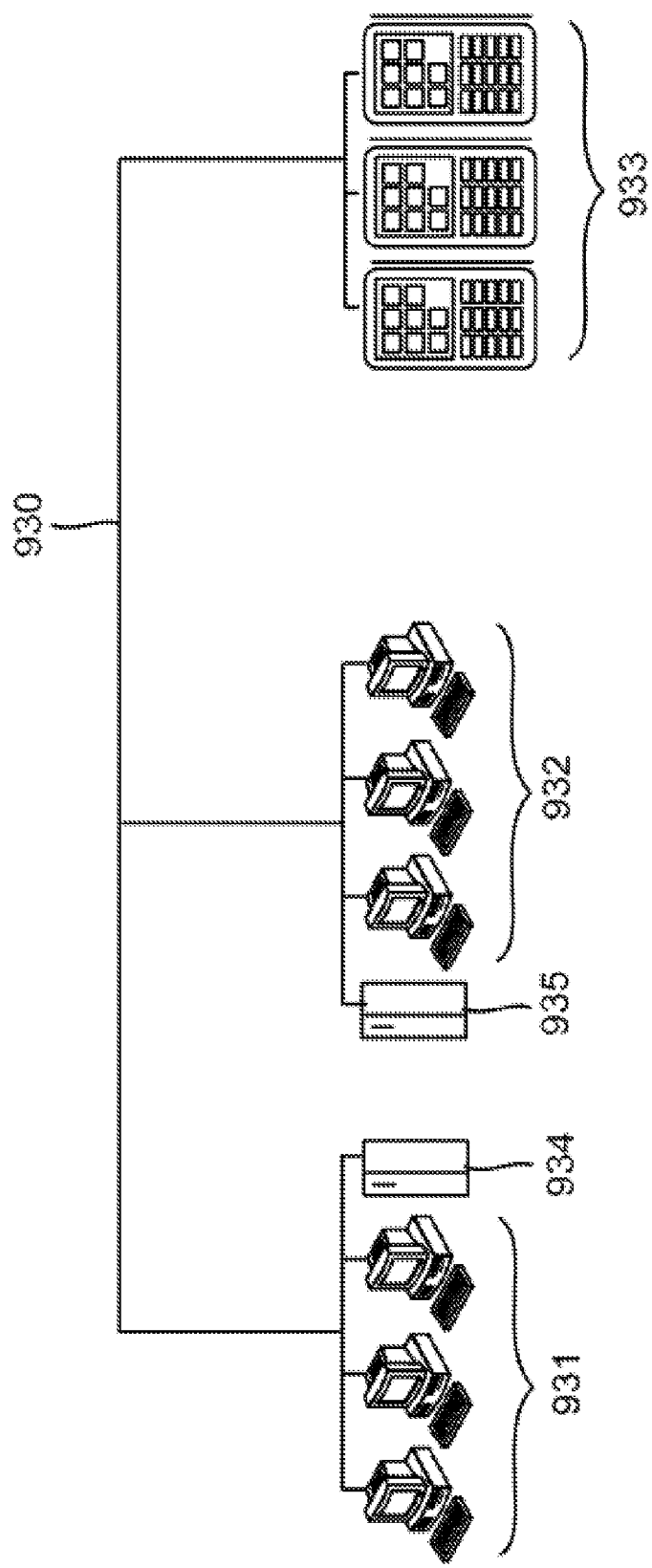
FIG. 9C depicts an exemplary network of computer systems.

FIG. 9C is a diagram showing a network 930 with a plurality of computer systems 931, and 932, a plurality of cell phones and personal data assistants 933, and Network Attached Storage (NAS) 934, and 935. In example embodiments, systems 931, 932, and 933 can manage data storage and optimize data access for data stored in Network Attached Storage (NAS) 934 and 935. A mathematical model can be used for the data and be evaluated using distributed parallel processing across computer systems 931, and 932, and cell phone and personal data assistant systems 933. Computer systems 931, and 932, and cell phone and personal data assistant systems 933 can also provide parallel processing for adaptive data restructuring of the data stored in Network Attached Storage (NAS) 934 and 935. FIG. 9C illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as Network Attached Storage (NAS) through a separate network interface. In some example embodiments, processors can maintain separate memory spaces and transmit data through network interfaces, back plane or other connectors for parallel processing by other processors. In other embodiments, some or all of the processors can use a shared virtual address memory space.

Figure 9D:
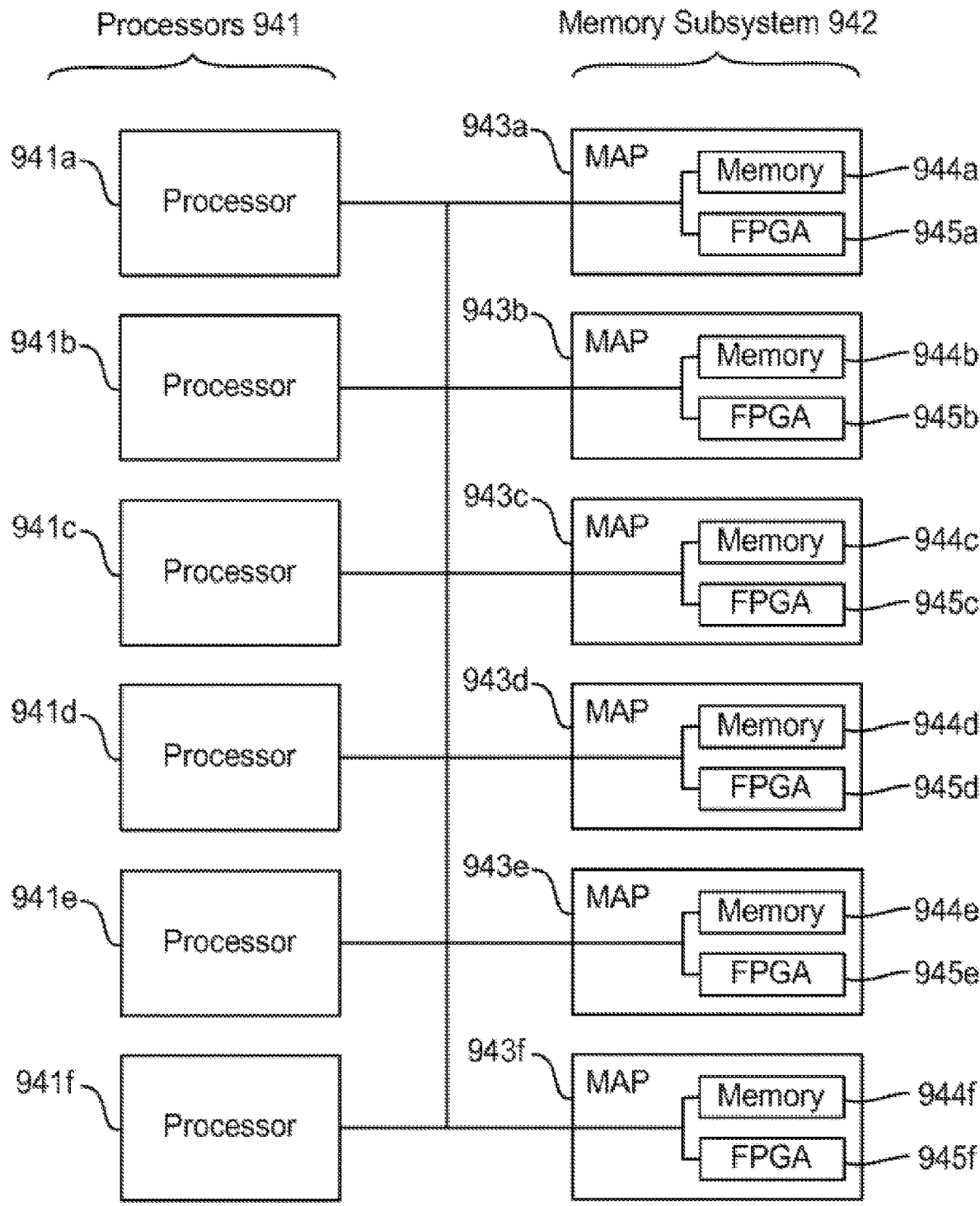
FIG. 9D depicts an exemplary multiprocessor computer system.

FIG. 9D is a block diagram of a multiprocessor computer system 940 using a shared virtual address memory space in accordance with an example embodiment. The system includes a plurality of processors 941a-f that can access a shared memory subsystem 942. The system incorporates a plurality of programmable hardware memory algorithm processors (MAPs) 943a-f in the memory subsystem 942. Each MAP 943a-f can comprise a memory 944a-f and one or more field programmable gate arrays (FPGAs) 945a-f. The MAP provides a configurable functional unit and particular algorithms or portions of algorithms can be provided to the FPGAs 945a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 944a-f, allowing it to execute tasks independently of, and asynchronously from, the respective microprocessor 941a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 9D, system on chips (SOCs), application specific integrated circuits (ASICs), or other processing and logic elements. For example, the Set Processor and Optimizer can be implemented with hardware acceleration through the use of a hardware accelerator card, such as accelerator card 922 illustrated in FIG. 9B.

Reports

The methods and systems further provide for generating a report wherein the report can identify the one or more subjects present in a complex sample. Alternatively, the report can provide detailed information on the readout of all features contained in the detection device. A report can be any technique by which the results of the methods described herein are relayed to an end-user. The report can be displayed on a screen or electronic display or can be printed on e.g., a sheet of paper. In some cases, the report is transmitted over a network. In some cases, the network is the Internet. In some cases, the report can be generated manually. In other cases, the report can be generated automatically. In some cases, the report can be generated in real-time. In some cases, the report can be provided to a mobile device, smartphone, tablet or another network enabled device.

EXAMPLES

Example 1. Generating Subject Specific Probes

A sample is obtained. The sample comprises multiple subjects. The genomes of each subject to be identified are obtained. Non-overlapping regions of the subjects' genomes are identified. Probes specific to the non-overlapping regions are designed.

Example 2. Constructing Subject Specific Features

A biochip is constructed comprising subject specific features. Each feature comprises a plurality of probes specific to an individual subject.

Example 3. Assaying for the Presence of a Subject Using the Biochip

A test sample containing of many types subjects is obtained. DNA from the sample is obtained en masse. With no amplification the DNA is hybridized to the biochip. Multiple targets bind to probes on the surface of the biochip. When a sufficient number of probes are bound within a feature a signal is detectable and a subject specific feature is called positive. Positive features are indicative of the presence of a subject in the sample. In some cases, a positive signal indicates the presence of a specific organism or species. In another case, a positive signal indicates the presence of a specific gene or trait of interest.

Example 4. Improvement of Probe Immobilization Using a Two-Step EDC Protocol

A two-step EDC (1-ethyl-3-(3-dimethylaminopropyl)carbodiimide hydrochloride) protocol was utilized to improve probe immobilization to a silica bead. The silica beads were treated with a low concentration of EDC, washed, and subsequently treated with a higher concentration of EDC. Table 3 below demonstrates the effect of different EDC concentrations on probe immobilization efficiency.

TABLE 3

Two-step EDC protocol improves probe immobilization to silica beads.

| Name | EDC Conc. (mM) | # Beads in rxn | Cy5 added (nmole) | Cy5 conjugated (nmole) | Cy5 unconjugated (nmole) | Yield | # probes per bead | Probe Spacing (Å) |
|---|---|---|---|---|---|---|---|---|
| EDC-0 | 3.2/6.4 | 2.39 × 10$^9$ | 1.12 | 0.20 | 0.89 | 18% | 49,900 | 79.4 |
| EDC-1 | 32/64 | 1.19 × 10$^9$ | 0.56 | 0.43 | 0.62 | 41% | 107,900 | 54.0 |
| EDC-2 | 64/128 | 1.19 × 10$^9$ | 0.56 | 0.31 | 0.55 | 36% | 78,300 | 63.4 |
| EDC-3 | 96/192 | 1.19 × 10$^9$ | 0.56 | 0.22 | 0.53 | 29% | 55,200 | 75.4 |

Example 5. Probe Design to M13mp8 Sequence

Figure 4:
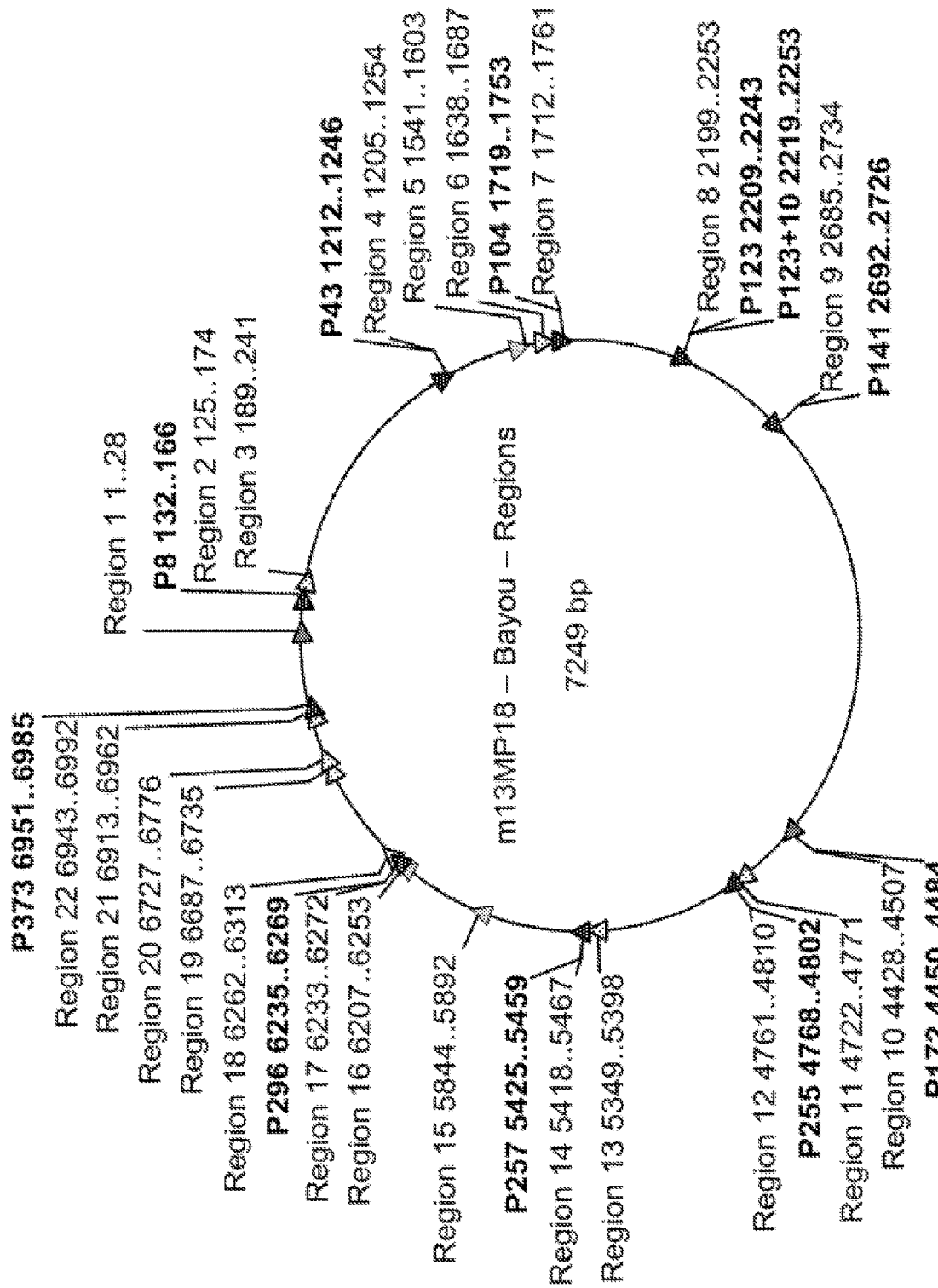
FIG. 4 depicts 22 unique regions identified on M13mp18 phage vector sequence.

Probes were designed to the M13mp8 phage vector derived from the M13 bacteriophage. Briefly, the M13mp8 sequence was queried against GenBank Viruses, Bacteria, and Human databases and the "natural" M13 bacteriophage sequence. It was determined that M13mp8 has 22 unique regions (see, e.g., FIG. 4) and 380 unique 35-mers. These sequences were used to generate 10 probes that are capable of distinguishing M13mp8 from a complex sample. Probes were designed to have a variety of GC content/T$_m$ and Hairpin T$_m$. In some cases, probes were modified to include: 1. No modification; 2. Amino-modification (5'); 3. Amino-modification (5')+Cy5 (3'). In some cases, target nucleic acids were generated either without a modification or a Cy3 (5') modification. FIG. 5 depicts examples of probes designed using the methods provided herein.

Example 6. Analysis of Tuberculosis Samples

Two categories of tuberculosis sample, viral (TBV) and non-viral (TBA), were assayed using bead-based probes. Probes were selected put in different pools, creating various multiplexes of probes. Probes were then placed on 1 micron beads. These beads were then hybridized using a specific target of TB strain (TBV) and a non-specific target (TBA) to which probes should not bind.

The assays were conducted according to the following protocol. Hybridization Buffer and Wash Buffer are described in Table 4. 4 μL of 10 mg/mL beads were diluted into 200 μL total volume with 1× Hybridization Buffer. The bead solution was then sonicated (1 minute in Branson 2510 sonicator) and 10 μL of the bead solution was added to final hybridization solution for a final concentration of 0.1 mg/mL. Final hybridization solution comprised 20 μL of labeled DNA and beads in 1× Hybridization Buffer. 10 μL DNA was added at desired cell equivalent in 1X Hybridization Buffer to final hybridization solution. Samples were mixed and spun down. The temperature was then ramped up to 95° C. for 5 minutes, and then down to 42° C. at a rate of 2° C. per minute. Samples were then spun down again, covered with foil, and nutate reaction was conducted overnight (about 16 hours) at 42° C. Samples were then washed twice in 100 μL 1× Hybridization Buffer, removing 80 μL at each wash step, and vortexed after each resuspension. The final 20 μL remaining after washes was then vortexed and sonicated, and the entire volume was added to a flow cell. Samples in the flow cell were incubated for 10 to 15 minutes. Each lane was then washed with 150 μL (3×50 μL) 1× Wash Buffer. Results were then collected through observation via microscope. Average signal and average background were measured for at least 30 beads per hybridization reaction.

TABLE 4

Hybridization and Wash Buffers.

1× Hybridization Buffer - make fresh daily

| | Stock | 1× Hybridization Buffer | 1× Volume (μL) |
|---|---|---|---|
| SSC Buffer (x) | 20 | 5 | 500 |
| SDS (%) | 10 | 0.1 | 20 |
| Formamide, deionized (%) | 100 | 50 | 1000 |
| H$_2$O | | | 480 |
| Total | | | 2000 |

1× Wash Buffer - keep at room temperature and re-use

| | Stock | 1× Wash Buffer | 1× Volume (μL) |
|---|---|---|---|
| SSC Buffer (x) | 20 | 0.1 | 100 |
| SDS (%) | 10 | 0.1 | 200 |
| H$_2$O | | | 19700 |
| Total | | | 20000 |

Figure 10:
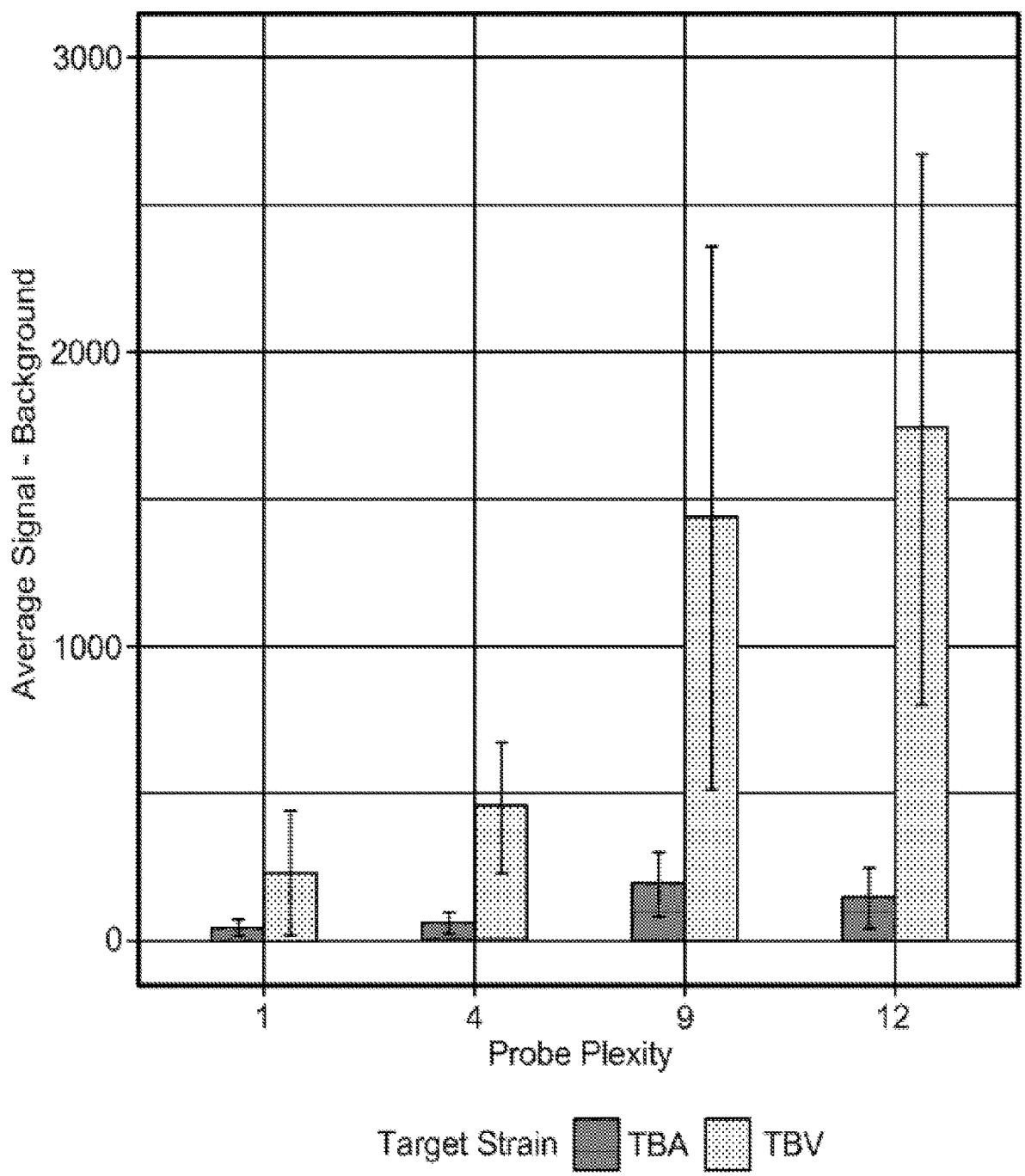
FIG. 10 shows results from an assay for viral versus non-viral tuberculosis.

FIG. 10 shows results from the experiment. The x-axis shows probe plexity (1, 4, 9, and 12), which represents the number of unique probes, and the y axis shows the average signal above background. The specific target signal (TBV, right) increases for each increase of plex factor for the specific target. Additionally, the non-specific signal (TBA, left) is flat with plex factor increase.

The present invention has been described in terms of one or more preferred embodiments, and it should be appreciated that many equivalents, alternatives, variations, and modifications, aside from those expressly stated, are possible and within the scope of the invention.

Example 7. Constructing a Microwell Detection Device

A detection device comprising a microwell plate with 384 sample wells is constructed, with each well corresponding to a unique subject specific feature. Each feature comprises a plurality of unbound, pooled probes specific to an individual subject.

Example 8. Assaying for the Presence of a Subject Using the Microwell Detection System A test sample containing of many types subjects is obtained. DNA from the sample is obtained en masse. With no amplification the DNA is applied to each well of the microwell plate, where it is able to hybridize to any complementary probes in the well, each probe comprising a reporter and a quencher, and subsequent PCT of the microwell plate results in a detectable fluorescence signal produced by FRET in wells where the target nucleic acid hybridizes to its complementary probes. Detection of this signal is indicative of the presence of a subject in the sample. In some cases, a positive signal indicates the presence of a specific organism or species. In another case, a positive signal indicates the presence of a specific gene or trait of interest.

Example 9. Constructing an Electrode Detection Device

A detection device comprising chip with a microfluidic channel in which five gold electrodes have been placed is constructed. Immobilized to each electrode are secondary (capture) probes corresponding to a sequence within 30 bp of a unique subject specific feature. Each electrode detects a different subject specific feature.

Example 10. Assaying for the Presence of a Subject Using the Electrode Detection System A test sample containing of many types subjects is obtained. DNA from the sample is obtained en masse. With no amplification the DNA is applied to the microfluidic channel in combination with a plurality of pooled probes complementary to target nucleic acid representing five subject specific features. Each probe comprises a ferrocene label, and hybridization of the labeled probe with its target generates a target nucleic acid: ferrocene labeled probe complex. Following application to the microfluidic channel hybridization of the target nucleic acid: ferrocene labeled probe complex to complementary secondary probes on the electrodes results in generation of an electrochemical signal by the electrode following application of a voltage. Detection of this signal is indicative of the presence of a subject in the sample. In some cases, a positive signal indicates the presence of a specific organism or species. In another case, a positive signal indicates the presence of a specific gene or trait of interest.

Example 11. Constructing a Nanopore Detection Device

A detection device comprising a microfluidic channel further comprising two pores is constructed. The first pore comprises a first electrode emitting a first voltage and the second pore comprises a second electrode emitting a second voltage. Detection using this dual pore based system can be done for a plurality of pooled probes.

Example 12. Assaying for the Presence of a Subject Using the Nanopore Detection System A test sample containing of many types subjects is obtained. DNA from the sample is obtained en masse. With no amplification the DNA is applied to the microfluidic channel in combination with a plurality of pooled probes complementary to target nucleic acid representing five subject specific features. Each probe comprises a different number of PEG molecules depending on which of the five subject specific features it corresponds to. For instance, probes to the first subject specific feature comprise one PEG molecule, probes to the second subject specific feature comprise two PEG molecules, and so forth. Passage of the target nucleic acid bound to its complementary probe through the pores results in a unique current impedance signal. Detection of this signal is indicative of the presence of a subject in the sample. In some cases, a positive signal indicates the presence of a specific organism or species. In another case, a positive signal indicates the presence of a specific gene or trait of interest.

Example 13. Detection of and Differentiation Between Strains of *Staphylococcus*

A partially assembled flow cell was created by attaching a three lane (20 µl/lane) pressure sensitive adhesive (PSA) cutout to an amino silane slide. Probes were generated for each strain, wherein the probes contained nucleic acid sequences unique to their respective strains. The probes were used to distinguish between two different strains of Staphylococcus, methicillin sensitive *S. aureus* (MSSA) and methicillin-resistant *S. epidermidis* (MRSE). The probes were conjugated to COOH silica beads. The targets were hybridized in separate reactions for this experiment, to many thousands of identical beads to evaluate the specificity of the probes. The beads were sonicated and diluted in 1× TE for about 1 minute. The beads were then deposited onto the amino silane surface and incubated for at least ten minutes. This deposition process was carried out a maximum of three times for single lane plexity and/or for the discrimination study. The flow cell was completed by attaching a flow cell top to the PSA. TE was applied through the flow cell to wash out any unbound beads.

A target mixture was created with the desired target (the two strains of Staphylococcus) and Affymetrix hybridization buffer. The target mixture was heated to 95° C. and held for 5 minutes, after which it was moved to ice, incubated, added to the flow cell, and incubated overnight (about 16 hours). The flow cell lanes were washed first with Affymetrix buffer A, and then with Affymetrix wash buffer B.

Figure 12:
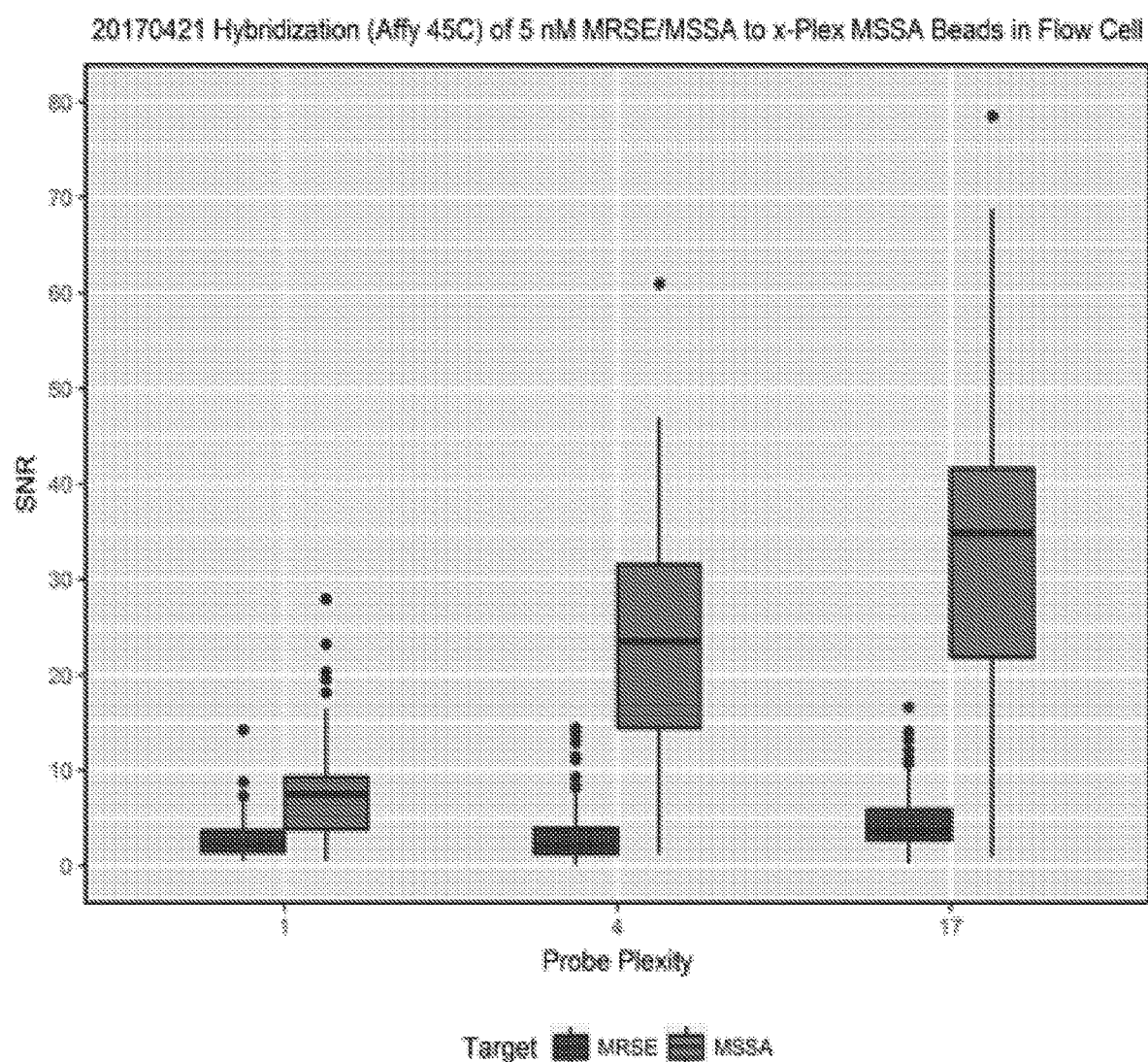
FIG. 12 illustrates the signal increase when detecting either the MRSE or MSSA strains of Staph. The Y-axis shows the signal to noise ratio (SNR), defined as "signal divided by standard deviation of the background." In this example, a strain is defined as being detected when it has an SNR>3, since the probability of a signal with an SNR>3 being background is <0.3% (null hypothesis testing).
Figure 13:
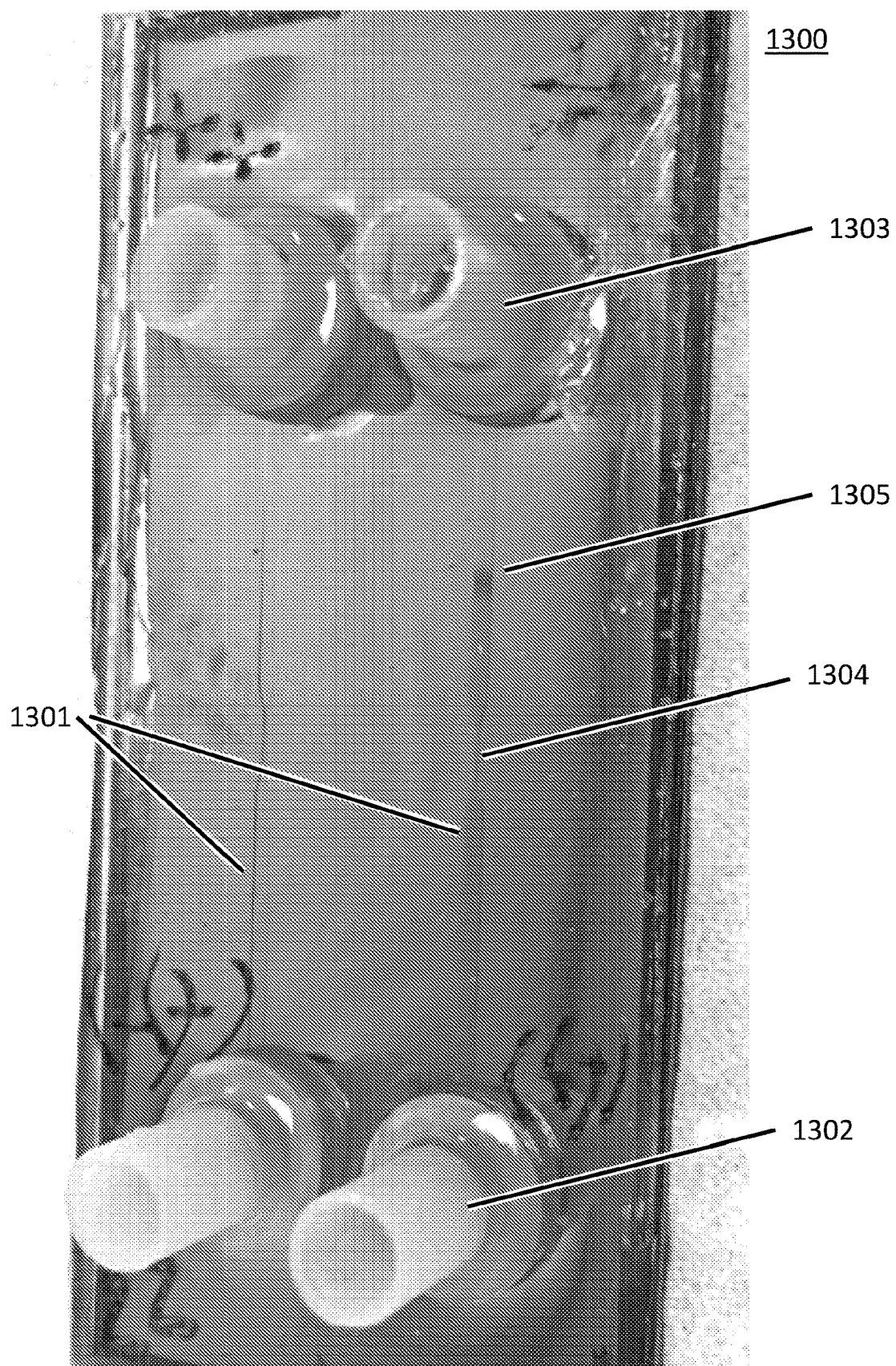
FIG. 13 shows an image of a DNA band migrating through a flow cell under ITP.

A fluorescence signal was recorded from multiple identical beads using a confocal microscope. FIG. 12 showed an increase in the signal to noise ratio (SNR) when detecting the MRSE and MSSA strains of Staph, as well as the ability to differentiate between strains at three different levels of probe plexity (i.e. 1 probe per strain per bead, 4 probes per strain per bead, 17 probes per strain per bead). Different lanes were used to distinguish between the different probes.

Figure 14A:
FIGS. 14A-14H show close-up images of a DNA band migrating through a flow cell under ITP.
Figure 14B:
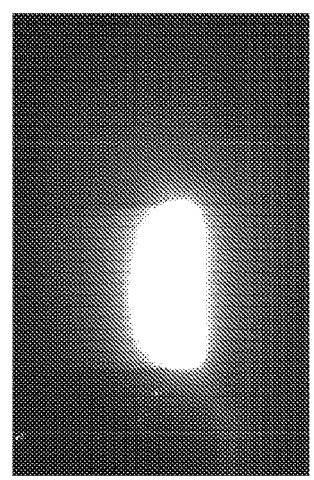
Figure 14C:
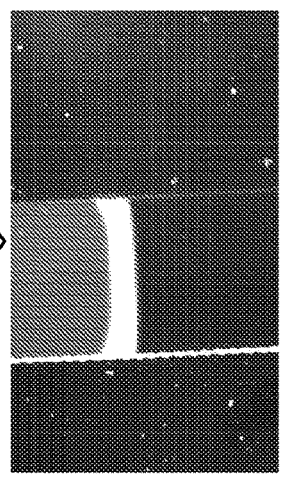
Figure 14D:
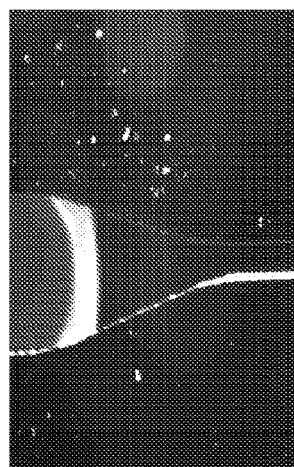
Figure 14E:
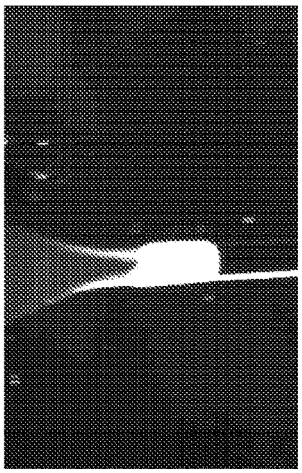
Figure 14F:
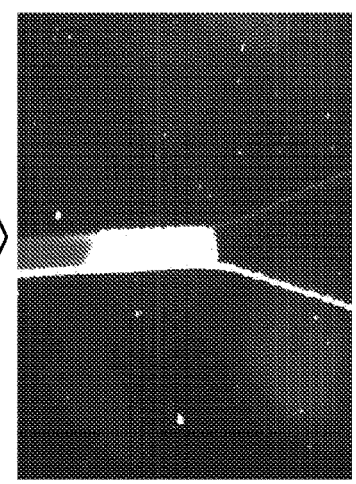
Figure 14G:
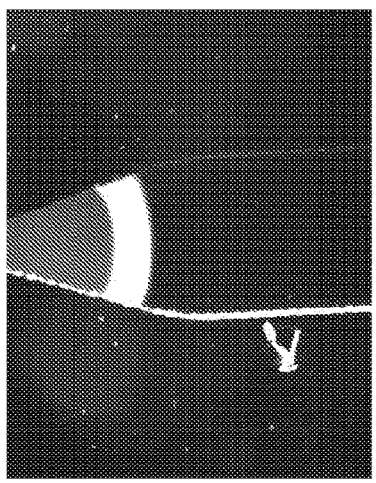
Figure 14H:
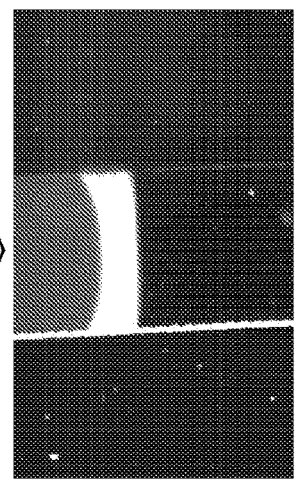

Example 14. Concentrating and Moving DNA in a Flow Cell on a Silicon Substrate ITP was conducted on a silicon substrate (see, e.g., FIG. 13 and FIG. 14A-14H). Chemical vapor deposition was used to create a silicon oxide layer on the bead array surface, with a thickness of about 500 nanometers (nm). A flow cell 1301 with inlet 1302 and outlet 1303 was fabricated in PDMS with dimensions of about 4 cm in length, 800 µm in width, and 75 µm in height, with a tapered section 1304 in the middle of the flow cell length narrowing to about 200 µm width before expanding again. The lower surface of the PDMS flow cell was activated using an electric discharge wand, to enable bonding of the PDMS to the silicon oxide surface. Platinum wires at two ports at the inlet and outlet ends of the flow cell were set to a voltage of 200 V, with a resulting current of about 100 µA. Sample was loaded and a concentrated band of DNA 1305, fluorescently labeled with Cy3, formed and migrated down the channel. Total time for loading, concentration, hybridization, and detection of DNA was about 25 minutes. Concentration of Cy3 and target DNA was 25 nM, and the process was successfully repeated at a concentration of 0.25 nM. FIG. 14A shows fluorescently labeled sample DNA exiting the inlet port. FIG. 14B shows the DNA band beginning to focus in the flow cell channel. FIG. 14C shows a focused DNA band formed in the flow cell channel. FIG. 14D shows the DNA band entering the "throat" of the tapered section of the flow cell channel. FIG. 14E shows the DNA band moving through the throat. FIG. 14F shows the DNA band approaching the end of the throat. FIG. 14G shows the DNA band entering the array hybridization region of the flow cell channel. FIG. 14H shows the DNA band in the hybridization region of the flow cell channel.

What is claimed is:

1. A method, comprising:
   a. providing a sample comprising one or more analytes;
   b. concentrating or transporting said one or more analytes by isotachophoresis (ITP) in a channel; wherein a surface of said channel comprises a silicon substrate, wherein said silicon substrate comprises an insulating layer over a surface of said silicon substrate, wherein said channel comprises probes arranged in an array, and wherein probes in a single feature of said array comprise at least two species of probes; and
   c. detecting signals associated with binding of at least a subset of the one or more analytes to the probes, such that signals associated with said single feature of said array are integrated into a single resolution element.

2. The method of claim 1, wherein said insulating layer comprises silicon oxide.

3. The method of claim 1, wherein said insulating layer is at least about 250 nanometers thick.

4. The method of claim 1, wherein said surface comprises at least one well.

5. The method of claim 4, wherein said at least one well is a microwell.

6. The method of claim 4, wherein said at least one well comprises an array of wells.

7. The method of claim 1, wherein said probes arranged in said array are coupled to said surface.

8. The method of claim 1, wherein said at least two species of probes are each specific to a same subject.

9. The method of claim 8, wherein said subject is selected from the group consisting of: a species of organism, a strain of organism, a clade of organism, a genetic variant, a trait of pathogenicity, a trait of resistance, and an individual member of a species of organism.

10. The method of claim 1, wherein said ITP is conducted at a voltage of equal to or less than about 800 volts.

11. The method of claim 1, wherein said channel has a height of equal or less than 100 micrometers.

12. The method of claim 1, wherein said channel does not comprise a constriction or a tapered section.

13. The method of claim 1, wherein said channel has a width of equal to or less than 2000 micrometers.

14. The method of claim 1, wherein said one or more analytes comprises nucleic acid.

15. The method of claim 1, further comprising binding said one or more analytes to one or more probes on said surface.

16. The method of claim 1, wherein said method is conducted in equal to or less than about 60 minutes.

17. The method of claim 1, wherein said ITP is conducted at a field strength of about 10 V/cm to about 1000 V/cm.

* * * * *